United States Patent
Brister et al.

(10) Patent No.: US 11,819,433 B2
(45) Date of Patent: *Nov. 21, 2023

(54) PRESSURE CONTROL SYSTEM FOR INTRAGASTRIC DEVICE

(71) Applicant: Reshape Lifesciences Inc., San Clemente, CA (US)

(72) Inventors: Mark C. Brister, San Diego, CA (US); Neil R. Drake, Carlsbad, CA (US); Daniel J. Proctor, Carlsbad, CA (US); Madeline Campbell, Poway, CA (US)

(73) Assignee: RESHAPE LIFESCIENCES INC., Irvine, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/993,110

(22) Filed: Aug. 13, 2020

(65) Prior Publication Data
US 2021/0196496 A1    Jul. 1, 2021

Related U.S. Application Data

(63) Continuation of application No. 15/792,638, filed on Oct. 24, 2017, now Pat. No. 10,772,752.

(60) Provisional application No. 62/559,949, filed on Sep. 18, 2017, provisional application No. 62/418,058, filed on Nov. 4, 2016.

(51) Int. Cl.
*A61F 5/00* (2006.01)
*A61M 25/10* (2013.01)

(52) U.S. Cl.
CPC ............ *A61F 5/0036* (2013.01); *A61F 5/003* (2013.01); *A61F 5/004* (2013.01); *A61F 5/0043* (2013.01); *A61F 5/0089* (2013.01); *A61M 25/10181* (2013.11); *A61F 5/0076* (2013.01); *A61M 25/10185* (2013.11); *A61M 25/10187* (2013.11)

(58) Field of Classification Search
CPC ........ A61F 5/0036; A61F 5/003; A61F 5/004; A61F 5/0042; A61F 5/0089; A61F 5/0079; A61M 25/10181; A61M 25/10185; A61M 25/10187; A61M 25/10184
See application file for complete search history.

(56) References Cited

U.S. PATENT DOCUMENTS

| | | | |
|---|---|---|---|
| 2,183,900 | A | 12/1939 | Voit et al. |
| 3,788,322 | A | 1/1974 | Michaels |
| 3,797,492 | A | 3/1974 | Place |
| 4,133,315 | A | 1/1979 | Berman et al. |
| 4,234,454 | A | 11/1980 | Strope |

(Continued)

FOREIGN PATENT DOCUMENTS

| | | |
|---|---|---|
| CN | 1714759 | 1/2006 |
| CN | 101249006 | 8/2008 |

(Continued)

OTHER PUBLICATIONS

Al Kahtani et al., Aug. 28, 2008, Bio-Enteric Intragastric Balloon In Obese Patients: A Retrospective Analysis Of King Faisal Specialist Hospital Experience; Obesity Surgery, 8 pp.

(Continued)

*Primary Examiner* — Sarah A Long
(74) *Attorney, Agent, or Firm* — Knobbe, Martens, Olson & Bear LLP

(57) ABSTRACT

Devices and methods for treating obesity are provided. More particularly, intragastric devices and devices for inflating and methods of fabricating, deploying, inflating, monitoring, and retrieving the same are provided.

19 Claims, 36 Drawing Sheets

(56) References Cited

U.S. PATENT DOCUMENTS

| | | |
|---|---|---|
| 4,236,521 A | 12/1980 | Lauterjung |
| 4,246,893 A | 1/1981 | Berson |
| 4,340,626 A | 7/1982 | Rudy |
| 4,416,267 A | 11/1983 | Garren et al. |
| 4,485,805 A | 12/1984 | Foster, Jr. |
| 4,489,440 A | 12/1984 | Chaoui |
| 4,517,979 A | 5/1985 | Pecenka |
| 4,545,367 A | 10/1985 | Tucci |
| 4,560,392 A | 12/1985 | Basevi |
| 4,607,618 A | 8/1986 | Angelchik |
| 4,694,827 A | 9/1987 | Weiner et al. |
| 4,718,639 A | 1/1988 | Sherwood et al. |
| 4,723,547 A | 2/1988 | Kullas et al. |
| 4,739,758 A | 4/1988 | Lai et al. |
| 4,812,315 A | 3/1989 | Tarabishi |
| 4,813,934 A | 3/1989 | Engelson et al. |
| 4,857,029 A | 8/1989 | Dierick et al. |
| 4,899,747 A | 2/1990 | Garren et al. |
| 4,917,885 A | 4/1990 | Chiba et al. |
| 4,925,446 A | 5/1990 | Garay et al. |
| 4,929,214 A | 5/1990 | Lieberman |
| 5,049,106 A | 9/1991 | Kim et al. |
| 5,084,061 A | 1/1992 | Gau et al. |
| 5,129,915 A | 7/1992 | Cantenys et al. |
| 5,135,488 A | 8/1992 | Foote et al. |
| 5,234,454 A | 8/1993 | Bangs |
| 5,259,399 A | 11/1993 | Brown |
| 5,308,326 A | 5/1994 | Zimmon |
| 5,431,917 A | 7/1995 | Yamamoto et al. |
| 5,603,698 A | 2/1997 | Roberts |
| 5,674,239 A | 10/1997 | Zadini |
| 5,713,141 A | 2/1998 | Mitchell et al. |
| 5,728,119 A | 3/1998 | Smith et al. |
| 5,852,889 A | 12/1998 | Rinaldi |
| 5,868,141 A | 2/1999 | Ellias |
| 5,897,205 A | 4/1999 | Sinsteden |
| 5,910,128 A | 6/1999 | Quinn |
| 5,938,669 A | 8/1999 | Klaiber |
| 6,427,089 B1 | 7/2002 | Knowlton |
| 6,454,785 B2 | 9/2002 | De Hoyos Garza |
| 6,579,301 B1 | 6/2003 | Bales et al. |
| 6,682,473 B1 | 1/2004 | Matsuura et al. |
| 6,689,141 B2 | 2/2004 | Ferrera |
| 6,733,512 B2 | 5/2004 | McGhan et al. |
| 6,981,980 B2 | 1/2006 | Sampson et al. |
| 6,988,983 B2 | 1/2006 | Connors et al. |
| 7,192,397 B2 | 3/2007 | Lewkowicz et al. |
| 7,682,306 B2 | 3/2010 | Shah |
| 7,699,863 B2 | 4/2010 | Marco et al. |
| 7,854,745 B2 | 12/2010 | Brister et al. |
| 8,066,780 B2 | 11/2011 | Chen |
| 8,162,969 B2 | 4/2012 | Brister et al. |
| 8,202,291 B1 * | 6/2012 | Brister ............ A61M 25/10185 623/23.65 |
| 8,282,666 B2 | 10/2012 | Birk |
| 8,292,911 B2 | 10/2012 | Brister |
| 8,562,589 B2 | 10/2013 | Imran |
| 8,647,358 B2 | 2/2014 | Brister et al. |
| 8,721,620 B2 | 5/2014 | Imran |
| 8,734,429 B2 | 5/2014 | Imran et al. |
| 8,740,911 B2 | 6/2014 | Brister et al. |
| 8,740,927 B2 | 6/2014 | Brister et al. |
| 8,764,733 B2 | 7/2014 | Imran |
| 8,809,269 B2 | 8/2014 | Imran |
| 8,809,271 B2 | 8/2014 | Imran |
| 8,845,674 B2 | 9/2014 | Brister et al. |
| 8,870,966 B2 | 10/2014 | Schwab et al. |
| 8,992,561 B2 | 3/2015 | Brister et al. |
| 9,011,477 B2 | 4/2015 | Brister et al. |
| 9,072,583 B2 | 7/2015 | Brister et al. |
| 9,173,758 B2 | 11/2015 | Brister et al. |
| 9,351,862 B2 | 5/2016 | Brister et al. |
| 9,468,550 B2 | 10/2016 | Brister et al. |
| 9,539,132 B2 | 1/2017 | Brister et al. |
| 9,662,239 B2 | 5/2017 | Brister et al. |
| 9,827,128 B2 | 11/2017 | Brister et al. |
| 9,895,248 B2 | 2/2018 | Brister et al. |
| 10,085,865 B2 | 10/2018 | Brister et al. |
| 10,264,995 B2 | 4/2019 | Brister et al. |
| 10,327,936 B2 | 6/2019 | Brister et al. |
| 10,335,303 B2 | 7/2019 | Brister et al. |
| 10,350,100 B2 | 7/2019 | Nelson et al. |
| 10,463,520 B2 | 11/2019 | Brister et al. |
| 10,537,453 B2 | 1/2020 | Brister et al. |
| 10,610,396 B2 | 4/2020 | Brister et al. |
| 10,617,545 B2 | 4/2020 | Brister et al. |
| 10,660,778 B2 | 5/2020 | McCarthey et al. |
| 10,675,165 B2 | 6/2020 | Brister et al. |
| 10,709,592 B2 | 7/2020 | Brister et al. |
| 10,772,752 B2 | 9/2020 | Brister et al. |
| 10,773,061 B2 | 9/2020 | Brister et al. |
| 10,874,537 B2 | 12/2020 | Brister et al. |
| 11,219,543 B2 | 1/2022 | Brister |
| 11,730,619 B2 | 8/2023 | Brister et al. |
| 2002/0091405 A1 | 7/2002 | Kieturakis |
| 2003/0021822 A1 | 1/2003 | Lloyd |
| 2003/0171768 A1 | 9/2003 | McGhan |
| 2004/0044351 A1 | 3/2004 | Searle |
| 2004/0044357 A1 | 3/2004 | Gannoe |
| 2004/0102677 A1 | 5/2004 | Frering |
| 2005/0055013 A1 | 3/2005 | Chalmers |
| 2005/0192614 A1 | 9/2005 | Binmoeller |
| 2005/0222329 A1 | 10/2005 | Shah et al. |
| 2005/0266109 A1 | 12/2005 | Chin et al. |
| 2005/0267405 A1 | 12/2005 | Shah |
| 2005/0267595 A1 | 12/2005 | Chen et al. |
| 2006/0058829 A1 | 3/2006 | Sampson et al. |
| 2006/0178691 A1 | 8/2006 | Binmoeller |
| 2006/0224145 A1 | 10/2006 | Gillis et al. |
| 2007/0078476 A1 | 4/2007 | Hull et al. |
| 2007/0178476 A1 | 4/2007 | Hull et al. |
| 2007/0100208 A1 | 5/2007 | Lewkowicz et al. |
| 2007/0100369 A1 | 5/2007 | Cragg et al. |
| 2007/0104754 A1 | 5/2007 | Sterling et al. |
| 2007/0104755 A1 | 5/2007 | Sterling et al. |
| 2007/0110934 A1 | 5/2007 | Goldman |
| 2007/0118168 A1 | 5/2007 | Lointier |
| 2007/0149994 A1 | 6/2007 | Sosnowski et al. |
| 2007/0156248 A1 | 7/2007 | Marco et al. |
| 2007/0173881 A1 | 7/2007 | Birk et al. |
| 2007/0207199 A1 | 9/2007 | Sogin et al. |
| 2007/0212559 A1 | 9/2007 | Shah |
| 2007/0250087 A1 | 10/2007 | Makower |
| 2007/0250101 A1 | 10/2007 | Horn et al. |
| 2007/0288033 A1 | 12/2007 | Murature et al. |
| 2007/0293885 A1 | 12/2007 | Binmoeller |
| 2008/0051866 A1 | 2/2008 | Chen et al. |
| 2008/0172079 A1 | 7/2008 | Birk |
| 2008/0215003 A1 | 9/2008 | Kornerup |
| 2008/0255601 A1 | 10/2008 | Birk |
| 2008/0306506 A1 | 12/2008 | Leatherman et al. |
| 2009/0082644 A1 | 3/2009 | Li |
| 2009/0118756 A1 | 5/2009 | Valencon et al. |
| 2009/0131968 A1 | 5/2009 | Birk |
| 2009/0182368 A1 | 7/2009 | Lunsford et al. |
| 2009/0182424 A1 | 7/2009 | Marco et al. |
| 2009/0187206 A1 | 7/2009 | Binmoelier et al. |
| 2009/0192535 A1 | 7/2009 | Kasic, II et al. |
| 2009/0222065 A1 | 9/2009 | Dlugos et al. |
| 2009/0259246 A1 | 10/2009 | Eskaros et al. |
| 2009/0312740 A1 | 12/2009 | Kim et al. |
| 2010/0063530 A1 | 3/2010 | Valencon |
| 2010/0100115 A1 | 4/2010 | Soetermans et al. |
| 2010/0168782 A1 | 7/2010 | Hancock |
| 2010/0174307 A1 | 7/2010 | Birk |
| 2010/0185049 A1 | 7/2010 | Birk |
| 2010/0198249 A1 | 8/2010 | Sabliere |
| 2010/0222802 A1 | 9/2010 | Gillespie et al. |
| 2011/0202127 A1 | 8/2011 | Mauch et al. |
| 2011/0208229 A1 | 8/2011 | Snow et al. |
| 2011/0295300 A1 | 12/2011 | Verd et al. |
| 2012/0010590 A1 | 1/2012 | Imran |
| 2012/0035642 A1 * | 2/2012 | O'dea ............ A61B 5/42 606/194 |

(56) References Cited

U.S. PATENT DOCUMENTS

| | | | |
|---|---|---|---|
| 2012/0123194 A1 | 5/2012 | Beckman et al. | |
| 2012/0259217 A1* | 10/2012 | Gerrans | A61M 25/10181 604/514 |
| 2012/0269365 A1 | 10/2012 | Ochiai et al. | |
| 2012/0296365 A1 | 11/2012 | Nguyen | |
| 2013/0165859 A1 | 6/2013 | Imran | |
| 2013/0226219 A1* | 8/2013 | Brister | A61F 5/0043 606/192 |
| 2013/0267983 A1 | 10/2013 | Pavlovic et al. | |
| 2014/0066968 A1 | 3/2014 | Pavlovic et al. | |
| 2014/0221912 A1 | 8/2014 | Imran | |
| 2014/0221927 A1 | 8/2014 | Imran et al. | |
| 2014/0288535 A1 | 9/2014 | Raven et al. | |
| 2015/0374525 A1 | 12/2015 | Brister et al. | |
| 2016/0029998 A1 | 2/2016 | Brister et al. | |
| 2016/0058322 A1 | 3/2016 | Brister et al. | |
| 2016/0193064 A1 | 7/2016 | Brister et al. | |
| 2016/0310306 A1 | 10/2016 | Brister et al. | |
| 2017/0027728 A1 | 2/2017 | Brister et al. | |
| 2017/0156909 A1 | 6/2017 | Brister et al. | |
| 2017/0290694 A1 | 10/2017 | Abad Belando | |
| 2018/0116849 A1 | 5/2018 | Brister et al. | |
| 2018/0221633 A1 | 8/2018 | Brister et al. | |
| 2019/0021629 A1 | 1/2019 | Calzi et al. | |
| 2019/0298561 A1 | 10/2019 | Brister et al. | |
| 2019/0365277 A1 | 12/2019 | Brister et al. | |
| 2020/0100925 A1 | 4/2020 | Brister | |
| 2020/0100926 A1 | 4/2020 | Brister et al. | |
| 2020/0179147 A1 | 6/2020 | Brister | |
| 2020/0237543 A1 | 7/2020 | McCarthy | |
| 2020/0253767 A1 | 8/2020 | Brister | |
| 2021/0196496 A1 | 7/2021 | Brister et al. | |
| 2021/0401321 A1 | 12/2021 | Calzi et al. | |
| 2022/0031489 A1 | 2/2022 | Calzi et al. | |
| 2022/0105323 A1 | 4/2022 | Brister | |
| 2022/0218505 A1 | 7/2022 | Brister et al. | |
| 2022/0273479 A1 | 9/2022 | Brister | |

FOREIGN PATENT DOCUMENTS

| | | |
|---|---|---|
| DE | 3540936 | 10/1986 |
| EP | 0 103 481 | 3/1984 |
| EP | 0 213 748 | 3/1987 |
| EP | 0 246 999 | 11/1987 |
| WO | WO 87/00034 | 1/1987 |
| WO | WO 90/11040 | 10/1990 |
| WO | WO 99/25418 | 5/1999 |
| WO | WO 01/68007 | 9/2001 |
| WO | WO 02/16001 | 2/2002 |
| WO | WO 02/40081 | 5/2002 |
| WO | WO 02/091961 | 11/2002 |
| WO | WO 03/055420 | 7/2003 |
| WO | WO 04/084763 | 10/2004 |
| WO | WO 05/094257 | 10/2005 |
| WO | WO 06/020929 | 2/2006 |
| WO | WO 07/136735 | 11/2007 |
| WO | WO 08/127941 | 10/2008 |
| WO | WO 09/055386 | 4/2009 |
| WO | WO 09/059802 | 5/2009 |
| WO | WO 09/059803 | 5/2009 |
| WO | WO 09/086119 | 7/2009 |
| WO | WO 11/041864 | 4/2011 |
| WO | WO 11/063479 | 6/2011 |
| WO | WO 14/036648 | 3/2014 |
| WO | WO 2016/171763 | 10/2016 |

OTHER PUBLICATIONS

Al-Momen et al., 2005, Intragastric Balloon For Obesity: A Retrospective Evaluation Of Tolerance And Efficacy, Obesity Surgery, 15(1):101-105.

Benjamin et al., Sep. 1988, Double-Blind Controlled Trial of the Garren-Edwards Gastric Bubble: An Adjunctive Treatment for Exogenous Obesity, Gastroenterology, 95(3):581-588.

Carvalho et al., 2008, An Improved Intragastric Balloon Procedure Using A New Balloon: Preliminary Analysis Of Safety And Efficacy, Obesity Surgery, 6 pp.

Coskun et al., Sep. 2008, Bioenterics Intragastric Balloon: Clinical Outcomes Of The First 100 Patients-A Turkish Experience, Obesity Surgery, 18(9): 1154-1156.

Dastis et al., Jul. 2008, Intragastric Balloon For Weight Loss: Results In 100 Individuals Followed For At Least 2.5 Years; Endoscopy, 41(7):575-580.

De Waele et al., Apr. 2001, Endoscopic vol. Adjustment Of Intragastric Balloons For Intolerance, Obesity Surgery, 11(2):223-224.

Doldi et al., 2002, Treatment Of Morbid Obesity With Intragastric Balloon In Association With Diet; Obesity Surgery, 12(4):583-587.

Dumonceau, Dec. 2008, Evidence-Based Review Of The Bioenterics Intragastric Balloon For Weight Loss, Obesity Surgery, 18(12):1611-1617.

Durrans et al., 1989, Comparison Of Weight Loss With Short Term Dietary And Intragastric Balloon Treatment; Gut, 30:565-568.

Eckhauser et al., 1984, Hydrostatic Balloon Dilation for Stomal Stenosis after Gastric Partitioning, Surgical Gastroenterology, 3(1):43-50.

Evans et al., 2001, Intragastric Balloon In The Treatment Of Patients With Morbid Obesity, British Journal of Surgery, 88:1245-1248.

Fernandes et al., Jan. 24, 2007, Intragastric Balloon For Obesity (Review), The Cochrane Collaboration, John Wiley & Sons, Ltd., Issue 1, 57 pp.

Forestieri et al., May 2006, Heliosphere Bag In The Treatment Of Severe Obesity: Preliminary Experience, Obesity Surgery, 16(5):635-637.

Gaggiotti et al., 2007, Adjustable Totally Implanted Intragastric Prosthesis (ATIIP). Endogast For Treatment Of Morbid Obesity: One Year Follow-Up Of A Multicenter Prospective Clinical Survey; Obesity Surgery, 17:949-956.

Geliebter et al., 1990, Gastric balloon to treat obesity: a double-blind study in nondieting subjects, The American Journal of Clinical Nutrition, 51:584-588.

Genco et al., 2005, Bioenterics Intragastric Balloon: The Italian Experience With 2,515 Patients; Obesity Surgery, 15(8):1161-1164.

Genco et al., 2008, Intragastric Balloon Or Diet Alone? A Retrospective Evaluation, Obesity Surgery, 18(8):989-992.

Genco et al., 2009, Laparoscopic Sleeve Gastrectomy Versus Intragastric Balloon: A Case-Control Study, Surg Endosc. Springer Science & Business Media, 4 pp.

Genco et al., Jan. 2006, Bioenterics Intragastric Balloon (BIB): A Short-Term, Double-Blind, Randomized, Controlled, Crossover Study On Weight Reduction In Morbidly Obese Patients, International Journal of Obesity, 30(1):129-133.

Gottig et al., Jun. 2009, Analysis Of Safety And Efficacy Of Intragastric Balloon In Extremely Obese Patients, Obesity Surgery, 19(6):677-683.

Imaz et al., Jul. 2008, Safety And Effectiveness Of The Intragastric Balloon For Obesity. A Meta-Analysis; Obesity Surgery; 18(7):841-846.

Langer, Apr. 30, 1998, Drug delivery and targeting, Nature, 392 Supp(6679):5-10.

Malik, 2006, Endoluminal And Transluminal Surgery: Current Status And Future Possibilities; Surgical Endoscopy, 20(8):1179-1192.

Martin et al., Jul. 2007, Safety of the Ullorex Oral Intragastric Balloon for the Treatment of Obesity, Journal of Diabetic Science and Technology, 1(4):574-581.

Mathus-Vliegen et al., Aug. 1990, Intragastric Ballon in the Treatment of Super-morbid Obesity—Double-Blind, Sham-Controlled, Crossover Evaluation of 500-Milliliter Balloon, Gastroenterology, 99(2):362-369.

Melissas et al., 2006, The Intragastric Balloon—Smoothing The Path To Bariatric Surgery, Obesity Surgery, 16:897-902.

(56) References Cited

OTHER PUBLICATIONS

Mion et al., Jul. 2007, Tolerance And Efficacy Of An Air-Filled Balloon In Non-Morbidly Obese Patients: Results Of A Prospective Multicenter Study; Obesity Surgery, 17(7):764-769.
Nieben et al., Jan. 1982, Intragastric Balloon as an Artificial Bezoar for Treatment of Obesity, The Lancet, 1(8265):198-199.
Ramhamadany et al., 1989, Effect Of The Gastric Balloon Versus Sham Procedure On Weight Loss In Obese Subjects; Gut, 30:1054-1057.
Rodriguez-Hermosa et al., 2009, Gastric Necrosis: A Possible Complication Of The Use Of The Intragastric Balloon In A Patient Previously Submitted To Nissen Fundoplication; Obesity Surgery, 19:1456-1459.
Roman et al., Apr. 2004, Intragastric Balloon For "Non-Morbid" Obesity: A Retrospective Evaluation Of Tolerance And Efficacy; Obesity Surgery, 14(4):539-544.
Sallet et al., Aug. 2004, Brazilian Multicenter Study of the Intragastric Balloon, Obesity Surgery, 14(7):991-998.
Totte et al., Aug. 2001, Weight Reduction By Means Of Intragastric Device: Experience With The Bioenterics Intragastric Balloon, Obesity Surgery, 11(4):519-523.
Trande et al., Dec. 2008, Efficacy, Tolerance And Safety Of New Intragastric Air-Filled Balloon (Heliosphere BAG) For Obesity: The Experience Of 17 Cases; Obesity Surgery, 4 pp.
vanSonnenberg et al., Aug. 1984, Percutaneous Gastrostomy: Use of Intragastric Ballon Support, Radiology, 152(2):531-532.
Wahlen et al., 2001, The Bioenterics Intragastric Balloon (BIB): How To Use It; Obesity Surgery, 11(4):524-527.

\* cited by examiner

PRESSURE CONTROL SYSTEM FOR INTRAGASTRIC DEVICE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/792,638, filed Oct. 24, 2017, which claims priority to U.S. Provisional Application No. 62/418,058, filed Nov. 4, 2016, and to U.S. Provisional Application No. 62/559,949, filed Sep. 18, 2017. Each of the aforementioned applications is incorporated by reference herein in its entirety, and each is hereby expressly made a part of this specification.

FIELD OF THE INVENTION

Devices and methods for treating obesity are provided. More particularly, intragastric devices and methods of fabricating, deploying, inflating, monitoring, and retrieving the same are provided.

BACKGROUND OF THE INVENTION

Obesity is a major health problem in developed countries. Obesity puts you at greater risk of developing high blood pressure, diabetes and many other serious health problems. In the United States, the complications of being overweight or obese are estimated to affect nearly one in three American adults, with an annual medical cost of over $80 billion and, including indirect costs such as lost wages, a total annual economic cost of over $120 billion. Except for rare pathological conditions, weight gain is directly correlated to overeating.

Noninvasive methods for reducing weight include increasing metabolic activity to burn calories and/or reducing caloric intake, either by modifying behavior or with pharmacological intervention to reduce the desire to eat. Other methods include surgery to reduce the stomach's volume, banding to limit the size of the stoma, and intragastric devices that reduce the desire to eat by occupying space in the stomach.

Intragastric volume-occupying devices provide the patient a feeling of satiety after having eaten only small amounts of food. Thus, the caloric intake is diminished while the person is satisfied with a feeling of fullness. Currently available volume-occupying devices have many shortcomings. For example, complex gastric procedures are required to insert some devices.

U.S. Pat. No. 4,133,315, the contents of which are incorporated herein by reference in their entirety, discloses an apparatus for reducing obesity comprising an inflatable, elastomeric bag and tube combination. The bag can be inserted into the patient's stomach 20 by swallowing. The end of the attached tube distal to the bag remains in the patient's mouth. A second tube is snaked through the nasal cavity and into the patient's mouth. The tube ends located in the patient's mouth are connected to form a continuous tube for fluid communication through the patient's nose to the bag. Alternatively, the bag can be implanted by a gastric procedure. The bag is inflated through the tube to a desired degree before the patient eats so that the desire for food is reduced. After the patient has eaten, the bag is deflated. The tube extends out of the patient's nose or abdominal cavity throughout the course of treatment.

U.S. Pat. Nos. 5,259,399, 5,234,454 and 6,454,785, the contents of which are incorporated herein by reference in their entirety, disclose intragastric volume-occupying devices for weight control that must be implanted surgically.

U.S. Pat. Nos. 4,416,267, 4,485,805, 4,607,618, 4,694,827, 4,723,547, 4,739,758, and 4,899,747 and European Patent No. 246,999, the contents of which are incorporated herein by reference in their entirety, relate to intragastric, volume-occupying devices for weight control that can be inserted endoscopically. Of these, U.S. Pat. Nos. 4,416,267, 4,694,827, 4,739,758 and 4,899,747, the contents of which are incorporated herein by reference in their entirety relate to balloons whose surface is contoured in a certain way to achieve a desired end. In U.S. Pat. Nos. 4,416,267 and 4,694,827, the contents of which are incorporated herein by reference in their entirety, the balloon is torus-shaped with a flared central opening to facilitate passage of solids and liquids through the stomach cavity. The balloon of U.S. Pat. No. 4,694,827, the contents of which are incorporated herein by reference in their entirety, has a plurality of smooth-surfaced convex protrusions. The protrusions reduce the amount of surface area which contacts the stomach wall, thereby reducing the deleterious effects resulting from excessive contact with the gastric mucosa. The protrusions also define channels between the balloon and stomach wall through which solids and liquids may pass. The balloon of U.S. Pat. No. 4,739,758, the contents of which are incorporated herein by reference in their entirety, has blisters on its periphery that prevent it from seating tightly against the cardia or pylorus.

The balloons of U.S. Pat. Nos. 4,899,747 and 4,694,827, the contents of which are incorporated herein by reference in their entirety, are inserted by pushing the deflated balloon and releasably attached tubing down a gastric tube. U.S. Pat. No. 4,723,547, the contents of which are incorporated herein by reference in their entirety discloses a specially adapted insertion catheter for positioning its balloon. In U.S. Pat. No. 4,739,758, the contents of which are incorporated herein by reference in their entirety, the filler tube effects insertion of the balloon. In U.S. Pat. No. 4,485,805, the contents of which are incorporated herein by reference in their entirety, the balloon is inserted into a finger cot that is attached by string to the end of a conventional gastric tube that is inserted down the patient's throat. The balloon of European Patent No. 246,999 is inserted using a gastroscope with integral forceps.

In U.S. Pat. Nos. 4,416,267, 4,485,805, 4,694,827, 4,739,758, and 4,899,747 and European Patent No. 246,999, the contents of which are incorporated herein by reference in their entirety, the balloon is inflated with a fluid from a tube extending down from the patient's mouth. In these patents, the balloon also is provided with a self-sealing hole (U.S. Pat. No. 4,694,827, the contents of which are incorporated herein by reference in their entirety), injection site (U.S. Pat. Nos. 4,416,267 and 4,899,747, the contents of which are incorporated herein by reference in their entirety), self-sealing fill valve (U.S. Pat. No. 4,485,805, the contents of which are incorporated herein by reference in their entirety), self-closing valve (European Patent No. 246,999, the contents of which are incorporated herein by reference in their entirety) or duck-billed valve (U.S. Pat. No. 4,739,758, the contents of which are incorporated herein by reference in their entirety). U.S. Pat. No. 4,723,547, the contents of which are incorporated herein by reference in their entirety, uses an elongated thick plug and the balloon is filled by inserting a needle attached to an air source through the plug.

U.S. Pat. No. 4,607,618, the contents of which are incorporated herein by reference in their entirety, describes a collapsible appliance formed of semi-rigid skeleton members joined to form a collapsible hollow structure. The appliance is not inflatable. It is endoscopically inserted into the stomach 20 using an especially adapted bougie having an ejector rod to release the collapsed appliance. Once released, the appliance returns to its greater relaxed size and shape.

U.S. Pat. No. 5,129,915, the contents of which are incorporated herein by reference in their entirety, the contents of which are incorporated herein by reference, relates to an intragastric balloon that is intended to be swallowed and that inflates automatically under the effect of temperature. Three ways that an intragastric balloon might be inflated by a change in temperature are discussed. A composition comprising a solid acid and non-toxic carbonate or bicarbonate is separated from water by a coating of chocolate, cocoa paste or cocoa butter that melts at body temperature. Alternatively, citric acid and an alkaline bicarbonate coated with non-toxic vegetable or animal fat melting at body temperature and which placed in the presence of water, can produce the same result. Lastly, the solid acid and non-toxic carbonate or bicarbonate are isolated from water by an isolation pouch of low-strength synthetic material which it will suffice to break immediately before swallowing the bladder. Breaking the isolation pouches causes the acid, carbonate or bicarbonate and water to mix and the balloon to begin to expand immediately. A drawback of thermal triggering of inflation is that it does not afford the degree of control and reproducibility of the timing of inflation that is desirable and necessary in a safe self-inflating intragastric balloon.

SUMMARY OF THE INVENTION

A free-floating, intragastric, volume-occupying device that can be inserted into the stomach by the patient swallowing it and letting peristalsis deliver it into the stomach in the same manner that food is delivered, or by positioning it with a catheter, is desirable.

Volume-occupying devices and methods for manufacturing, deploying, inflating, tracking, deflating and retrieving of such devices are provided. The devices and methods of the preferred embodiments may be employed for treating over weight and obese individuals. Methods employing the device of the preferred embodiments may be swallowed by a patient, with or without a catheter attached. Once in the stomach of the patient, the device is inflated with a preselected gas or mixture of gases, to a preselected volume. After a predetermined time period, the device can be removed using endoscopic tools or decreases in volume or deflate so as to pass through the remainder of the patient's digestive tract.

Inflation may be achieved by use of a removable catheter that initially remains in fluid contact with the device after it has been swallowed by the patient.

In a first aspect, a system for performing an inflation procedure to inflate an inflatable intragastric device or balloon is provided. The system includes an inflation fluid container comprising an inflation fluid; an inflatable intragastric balloon; a fluid pathway fluidly connecting the inflation fluid container and the balloon; at least one valve disposed along the fluid pathway and configured to control a volume of gas flowing through the fluid pathway into the balloon; a pressure gauge positioned along the fluid pathway so as to measure a balloon pressure within the balloon; and a computing device. The computing device is configured to provide instructions to the valve to dispense a volume of inflation fluid into the fluid pathway; to provide instructions to the valve to block the flow of the inflation fluid into the fluid pathway; to receive balloon pressure measurements from the pressure gauge; and to determine if the balloon is located within a constrained space, based upon the balloon pressure measurements.

In an embodiment of the first aspect, the constrained space is a first constrained space and the computing device is further configured to determine if the balloon is located within a second constrained space, based upon the balloon pressure measurements. In a further embodiment, the computing device is configured to distinguish between the first and second constrained spaces.

In another embodiment of the first aspect, the computing device is further configured to compare the balloon pressure measurement to a target balloon pressure; and to select instructions, wherein the instructions are selected from the group consisting of instructions to vent inflation fluid from the balloon, when the balloon pressure measurement is above the target balloon pressure, instructions to continue the inflation procedure; and instructions to terminate the inflation procedure. In a further embodiment, the computing device is further configured to provide fail-safe procedure instructions to a user.

In yet another embodiment of the first aspect, the volume of inflation fluid dispensed into the fluid pathway is a first volume of inflation fluid, and the computing device is further configured to compare the balloon pressure measurement to a target balloon pressure, and to provide instructions to the valve to dispense a second volume of inflation fluid into the fluid pathway, when the balloon pressure measurement is below the target balloon pressure.

In still another embodiment of the first aspect, the computing device is further configured to compare the balloon pressure measurement to a target balloon pressure, and to provide indicial that the balloon is filled.

In yet another embodiment of the first aspect, the pressure gauge is positioned between the valve and the balloon.

In yet another embodiment of the first aspect, the computing device is configured to compare receive balloon pressure measurements to safety criteria.

In yet another embodiment of the first aspect, the computing device is configured to determine if the balloon pressure measurement is within a second safety threshold.

In yet another embodiment of the first aspect, the constrained space has a volume less than or equal to 180 $cm^3$.

In yet another embodiment of the first aspect, the inflation fluid comprises $SF_6$ and nitrogen.

In a second aspect, a system for inflating an inflatable intragastric device is provide wherein the system includes a canister comprising an inflation fluid, an inflatable intragastric balloon, a fluid pathway fluidly joining inflation fluid container and the balloon. The fluid pathway includes a pressure sensor, a first pressure regulator that is configured to reduce the pressure of inflation fluid received from the canister to a pressure less than a constrained space-damaging pressure, first valve that controls the flow of the inflation fluid through the fluid pathway, an exhaust that vents inflation fluid from the balloon, and a processing unit. The processing unit receives pressure measurements from the pressure sensor, determines the location of the balloon, based on the received pressure measurements. When the balloon location is determined to be an unconstrained space, the processing unite determines an amount or volume of inflation fluid to dispense from the canister so as to achieve a target pressure within the balloon. This determination is based on the pressure measurements. Once the volume of inflation fluid to be dispensed is determined, the processing unit provides instructions to dispense inflation fluid into the fluid pathway, based on the determined amount of inflation fluid to dispense from the canister. When the balloon location is determined to be a constrained space, the processing unit provides instructions, such as to the user, to perform a fail-safe procedure.

In an embodiment of the second aspect, the processing unit is configured to vent inflation fluid from the balloon when balloon pressure is greater than about 17.2 kPa.

In another embodiment of the second aspect, the processing unit is configured to provide an alert when the balloon is located in a constrained space.

In another embodiment of the second aspect, the constrained space has a volume of less than or equal to about 180 cm$^3$.

In another embodiment of the second aspect, the target pressure is between about 9.5 kPa to about 13 kPa.

In another embodiment of the second aspect, the target pressure is between about 8.3 kPa to about 17.2 kPa.

In another embodiment of the second aspect, the inflation fluid comprises $SF_6$ and nitrogen.

In a third aspect, a method of inflating an intragastric balloon is provided, including iteratively detecting a pressure within an intragastric balloon in vivo and comparing the detected pressure to a safety threshold. When the detected pressure exceeds the safety threshold, venting an amount of inflation fluid from the balloon, and when the detected pressure is within the safety threshold, iteratively providing an additional volume of inflation fluid to the balloon, detecting an additional balloon pressure associated with the additional volume of inflation fluid and comparing the detected additional pressure to a target pressure, until the additional pressure equals the target pressure.

In an embodiment of the third aspect, instructions to perform a fail-safe procedure are provided when the detected pressure exceeds the safety threshold. In a further embodiment of the third aspect, the safety threshold is between about 0.2 kPa and about 7.0 kPa. In another further embodiment of the third aspect, the safety threshold is between about 17.2 kPa and about 75.0 kPa, while the balloon is being filled with the inflation fluid.

In another embodiment of the third aspect, the target pressure is between about 9.5 kPa and about 13 kPa. In a further embodiment of the third aspect, the target pressure is between about 8.3 kPa and about 17.2 kPa.

In yet another embodiment of the third aspect, the inflation fluid comprises $SF_6$ and nitrogen.

In a fourth aspect, a device for detecting the placement of an inflatable intragastric balloon within an anatomical constrained space, comprising: a pressure sensor for detecting a balloon pressure within an inflatable intragastric balloon in vivo.

In an embodiment of the fourth aspect, the device includes a computing device that is configured to control delivery of an inflation fluid into the inflatable intragastric balloon, receive a balloon pressure value from the pressure sensor during a balloon administration procedure, and compare the received balloon pressure value to a predetermined pressure range during balloon administration procedure, wherein a received balloon pressure above the predetermined pressure range is indicative of placement of the balloon in the anatomical constrained space. In a further embodiment of the fourth aspect, the anatomical constrained space is a hiatal hernia. In another further embodiment of the fourth aspect, the anatomical constrained space is the esophagus.

In a fifth aspect, a method of detecting the placement of an inflatable intragastric balloon within an anatomical constrained space is provided. The method includes iteratively delivering an inflation fluid into the balloon in vivo, so as to partially inflate the balloon, measuring a balloon pressure of the balloon while iteratively delivering the inflation fluid into the balloon, and comparing the balloon pressure to a predetermined pressure, wherein the predetermined pressure indicated the balloon is located within an anatomically constrained space. In a further embodiment of the fifth aspect, the anatomical constrained space is a hiatal hernia. In another further embodiment of the fifth aspect, the anatomical constrained space is the esophagus.

BRIEF DESCRIPTION OF THE DRAWINGS

FIG. 9A depicts the single lumen catheter 50, 1110 with bell-shaped needle sleeve 1000 protecting the hollow needle 1100. FIG. 9B shows a perspective cross-sectional view of the single lumen catheter 50, 1110 showing detail of the needle 1100, bell-shaped needle sleeve 1000, and tensile cord 1120 as a structural member providing increased tensile strength. FIG. 9C shows a perspective cross-sectional view of the single lumen catheter 50, 1110 showing additional detail of the needle 1100 and bell-shaped needle sleeve 1000 when seated in the head unit 110 of the self-sealing valve system 100 of FIGS. 3A-D.

DETAILED DESCRIPTION OF THE PREFERRED EMBODIMENT

Figure 1:
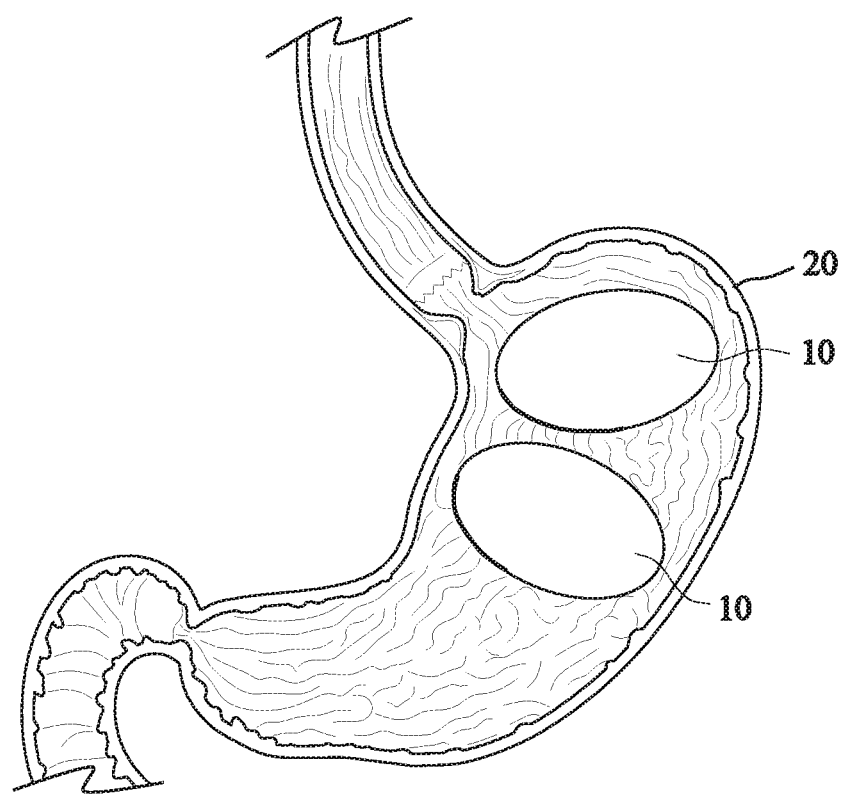
FIG. 1 depicts two intragastric balloons 10 placed within a patient's stomach.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The term "constrained space-damaging pressure" as used herein is a broad term, and is to be given its ordinary and customary meaning to a person of ordinary skill in the art (and is not to be limited to a special or customized meaning), and refers without limitation to a balloon pressure that is sufficient to damage the tissue when the balloon is in a constrained space. In some embodiments, a balloon pressure sufficient to damage the esophagus, when the balloon is constrained in the esophagus, is a pressure above about 70 kPa. In some embodiments, the pressure is above 60 kPa. In still another embodiment, the pressure is above 50 kPa. In a preferred embodiment, the pressure is above 50.3 kPa. In some embodiments, the pressure may be a pressure above 40 kPa.

The term "constrained space" as used herein is a broad term, and is to be given its ordinary and customary meaning to a person of ordinary skill in the art (and is not to be limited to a special or customized meaning), and refers without limitation to an anatomical space, especially associated with the esophagus or the stomach, that is smaller than the fully inflated balloon. Constrained spaces may be damaged by the balloon, if the balloon is inflated therein to a balloon pressure above 50.3 kPa. An exemplary constrained space has a volume of about 180 cm$^3$ or less. In another example, a constrained space is the esophagus or a hiatal hernia.

The term "degradable" as used herein is a broad term, and is to be given its ordinary and customary meaning to a person of ordinary skill in the art (and is not to be limited to a special or customized meaning), and refers without limitation to a process by which structural integrity of the balloon is compromised (e.g., by chemical, mechanical, or other means (e.g., light, radiation, heat, etc.) such that deflation occurs. The degradation process can include erosion, dissolution, separation, digestion, disintegration, delamination, comminution, and other such processes.

The term "swallowable" as used herein is a broad term, and is to be given its ordinary and customary meaning to a person of ordinary skill in the art (and is not to be limited to a special or customized meaning), and refers without limitation to ingestion of a balloon by a patient such that the outer capsule and its constituents are delivered to the stomach 20 via normal peristalsis movement. While the systems of preferred embodiments are swallowable, they are also configured for ingestion by methods other than swallowing. The swallowability of the system is derived, at least in part, by the outer container size for the self-inflating system and the catheter and outer container size for the manual inflation system. For the self-inflating system, the outer capsule is sufficient to contain the inner container and its constituents, an amount of activation agent injected prior to administration, the balloon size and the balloon material thickness. The system is preferably of a size less than the average normal esophagus diameter.

Described herein is an orally ingestible device. In preferred embodiments, the device is able to traverse the alimentary canal. The device may be useful, for example, as an intragastric volume-occupying device. The device overcomes one or more of the above-described problems and shortcomings found in current intragastric volume-occupying devices.

In order to more clearly describe the subject matter of the preferred embodiments, different embodiments of the same subcomponent will be described under a single relevantly-titled subheading. This organization is not intended to limit the manner in which embodiments of different subcomponents may be combined in accordance with the present invention.

Swallowable Intragastric Balloon System

A swallowable, inflatable intragastric balloon system according to selected preferred embodiments includes the following components: self-sealing valve system for addition of fluid to the lumen of the balloon ("valve system"), an intragastric balloon in a deflated and compacted state ("balloon" or "volume-occupying subcomponent") and an outer capsule, container, or coating ("outer container") that contains the balloon. An inflation assembly, described in greater detail in the section entitled "Inflation Assembly," is provided for inflating the balloon after ingestion or placement in the stomach. The inflation assembly includes, but is not limited to, an inflation fluid source and a catheter and/or tubing. In some embodiments, the inflation fluid source comprises an inflation fluid dispenser ("dispenser") and a container of inflation fluid ("can" or "canister") for use with the dispenser. A valve providing releasable attachment of the inflation assembly catheter or tubing to the balloon is provided. Preferably, the self-sealing valve system attached to the balloon (e.g., on its inside surface) is "universal" or compatible with a swallowable catheter or a physician-assisted catheter. The valve system serves to allow for balloon inflation using a miniature catheter that includes a needle assembly, while the balloon is in the patient's stomach, and provides a mechanism for detachment of the catheter after balloon inflation has been completed.

The outer container preferably incorporates the balloon in a compacted state (e.g., folded and rolled).

Selected components of a swallowable intragastric balloon system of a preferred embodiment can include a silicone head with radioopacity ring, trimmed 30 D silicone septum, Nylon 6 inoculation spacer, compacted balloon, and outer container as constituents of the system in unassembled form. A fully assembled outer container can include a vent hole aligned with a septum or a port for connection of tubing. As discussed further below, the components of particularly preferred systems possess the attributes described herein; however, in certain embodiments systems can be employed which utilize components having other attributes and/or values.

Devices according to the preferred embodiments are intended for ingestion by a patient and deployment without the need to resort to invasive methods. It is therefore desirable that the device of the preferred embodiments be operable to conform to a compact delivery state which can be swallowed by a patient using normal peristaltic motions and with minimal discomfort. Once in the stomach, it is desirable for the device to assume a substantially larger deployed state. In order to achieve the transition from a delivery state to a deployed state the device is subjected to inflation.

In order to treat obesity or assist individuals with their weight loss goals, various embodiments of the intragastric devices 10 (e.g., 'intragastric balloon' or 'balloon') described herein are preferably delivered to a patient's stomach 20 and maintained in the patient's stomach 20 in an inflated state, preferably for at least thirty days (see FIG. 1). In some embodiments, the inflated intragastric devices 10 are maintained in a patient's stomach 20 for a treatment duration of one to three months, and in some embodiments, the devices 10 are maintained in a patient's stomach 20 up to six months, up to 9 months, up to 12 months, or more. A plurality of intragastric devices 10 may be delivered to a patient's stomach 20 during a treatment duration. For example, in some embodiments, up to two or three or more inflated intragastric devices 10 (of the same size or of two or more different sizes) may be present in a patient's stomach 20 at a point in time. At the end of treatment, the devices 10 may be removed endoscopically. In other embodiments, the devices 10 may deflate and pass through the lower gastrointestinal tract. In preferred embodiments, this deflation of the devices 10 occurs at the end of a predetermined treatment time period, such as but not limited to a treatment period of about 3 months, about 6 months, about 9 months, about 12 months or longer. In order to maintain a proper degree of inflation and reduce discomfort and/or side effects for a patient, the patient may be prescribed one or more prescription drugs to take regularly while the inflated intragastric device 10 is in the patient's stomach 20. For example, in some embodiments, a proton pump inhibitor, an antiemetic, and/or a spasmolytic agent may be prescribed.

Outer Container

Figure 2:
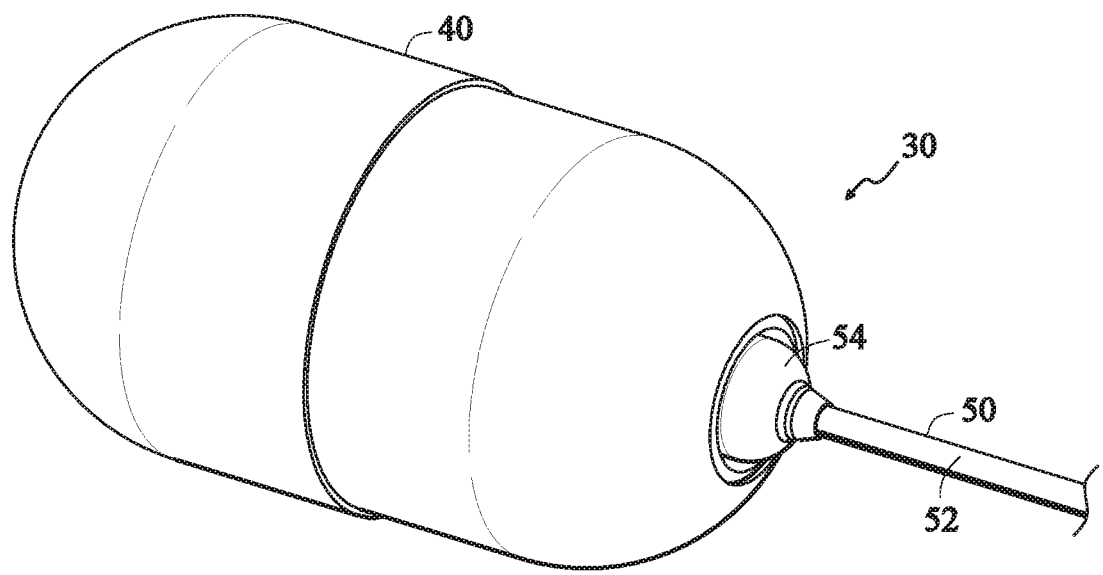
FIG. 2 depicts an Obalon Gastric Balloon Assembly 30, including a balloon outer container 40 ("capsule") containing an intragastric balloon (not shown) and an inflation catheter 50 coupled to the balloon within the capsule 40. The inflation catheter 50 includes tubing 52 and a bell-shaped needle sleeve 54.
Figure 3A:
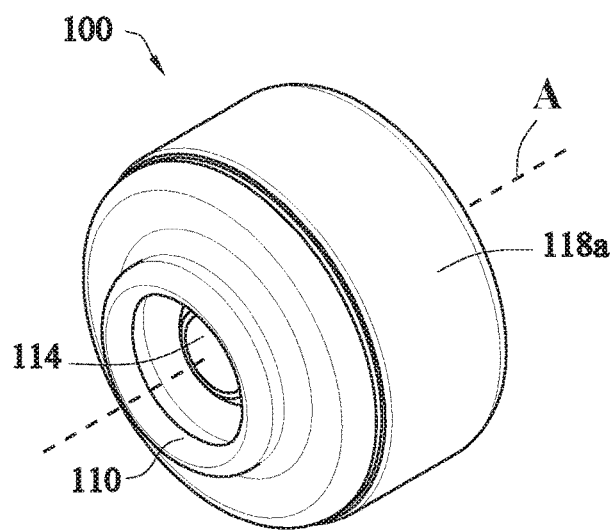
FIGS. 3A-D depict a perspective view (FIG. 3A), a side view (FIG. 3B), a top view (FIG. 3C) and a cross-sectional view (FIG. 3D) of a head assembly of a self-sealing balloon valve system 100 which contains a self-sealing septum (plug) 114 housed within a metallic concentric cylinder. The self-sealing balloon valve system 100 includes retaining rings 112, a ring stop 116, and a tube septum 118. The retaining structure includes tube septum 118, which includes a portion that is a larger outer cylinder 118a and a portion that is a smaller inner cylinder 118b, the inner cylinder 118b housing the septum 114 and the larger outer cylinder 118a housing the head unit 110, which is made of a material configured to provide compressive forces against a bell-shaped needle sleeve (not depicted). The inner cylinder 118b of the tube septum 118 includes a lip 118c configured for an interference lip with a bell-shaped needle sleeve (not depicted). The entire outer cylinder 118a is filled with a material forming the head unit 110, and a small circular lip 111 of this same material is provided, which is slightly larger than the diameter of the inner cylinder 118b and extends to the outside surface of the balloon (not depicted).
Figure 3B:
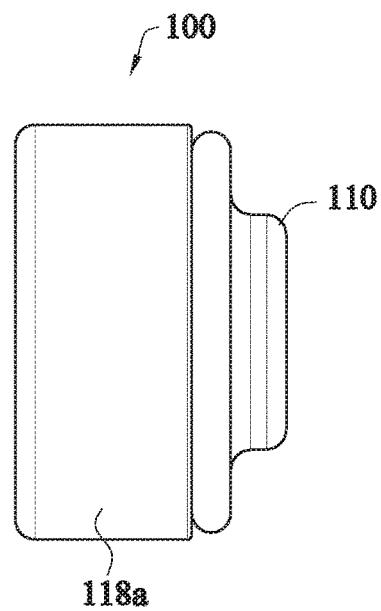
Figure 3C:
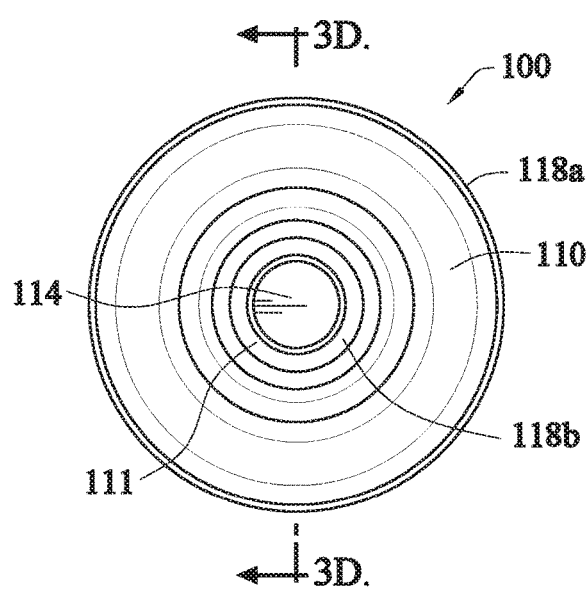
Figure 3D:
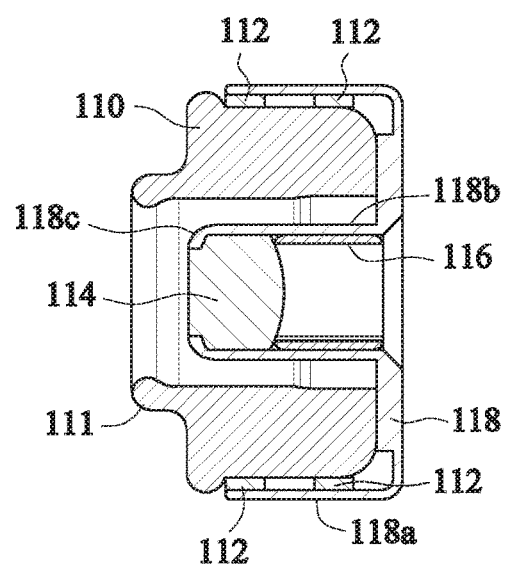
Figure 4A:
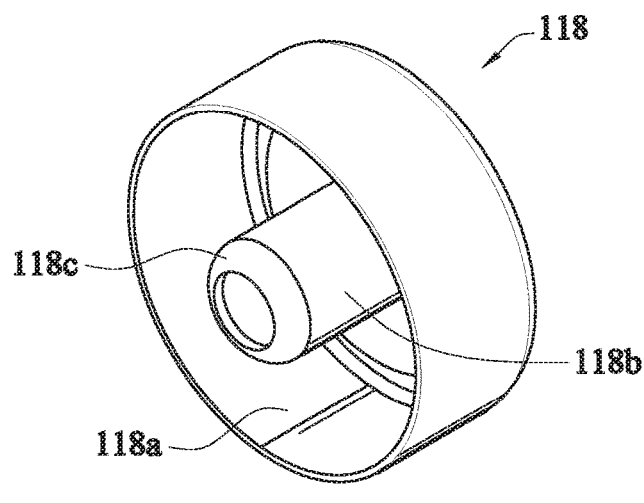
FIGS. 4A-D depict a perspective view (FIG. 4A), a side view (FIG. 4B), a cross-sectional view (FIG. 4D), and a top view (FIG. 4C) of tube septum 118. It includes a smaller inner cylinder 118b of a concentric metallic retaining structure into which a septum 114 can be inserted or otherwise fabricated into, as in the self-sealing valve system 100 of FIGS. 3A-D.
Figure 4B:
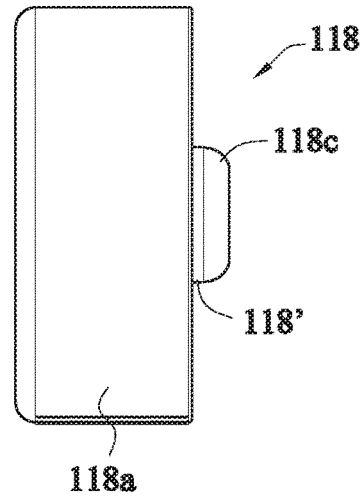
Figure 4C:
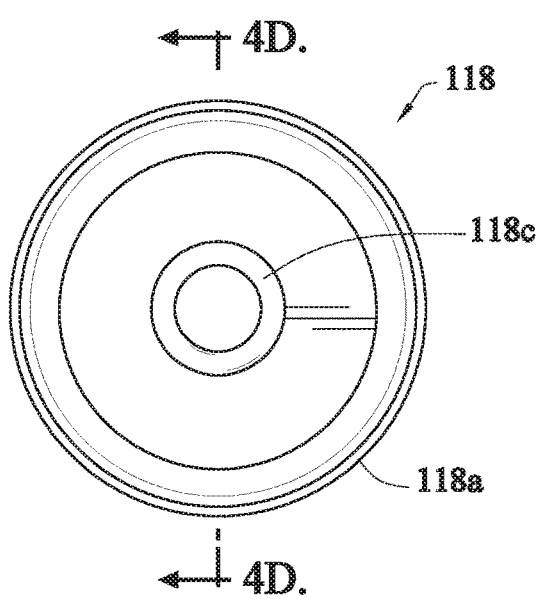
Figure 4D:
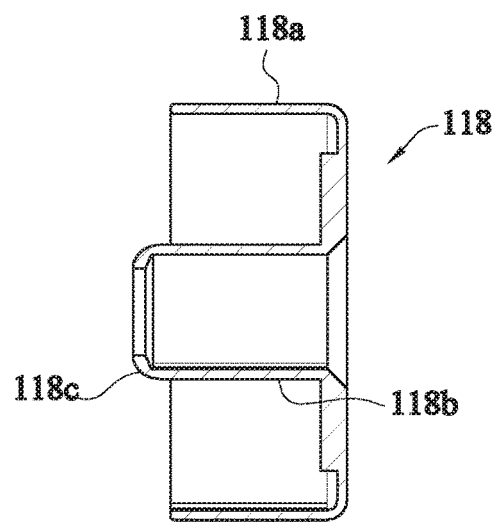
Figure 5A:
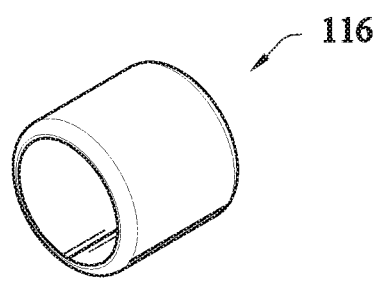
FIGS. 5A-C depict a perspective view (FIG. 5A), a side view (FIG. 5B), and a top view (FIG. 5C) of a ring stop 116—an additional ring placed at the distal end of an inner cylinder 118b to provide additional compression to ensure the septum material 114 is dense enough to re-seal itself, as in the self-sealing valve system 100 of FIGS. 3A-D.
Figure 5B:
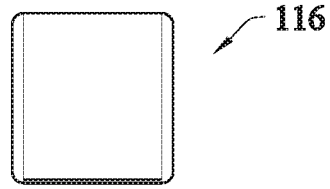
Figure 5C:
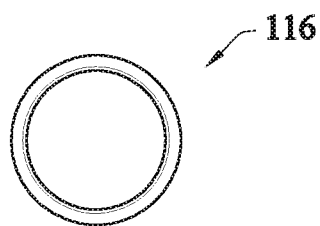
Figure 6A:
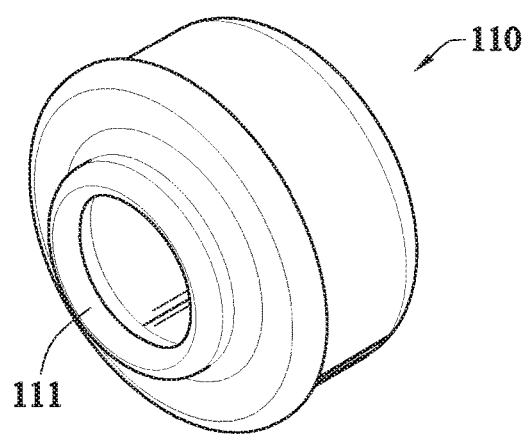
FIGS. 6A-D depict a perspective view (FIG. 6A), a side view (FIG. 6B), a cross-sectional view (FIG. 6C) and a top view (FIG. 6D) of a head unit 110 comprising an outer cylinder of a concentric valve housing comprising a higher durometer material than the inner cylinder, as in the self-sealing valve system 100 of FIGS. 3A-D.
Figure 6B:
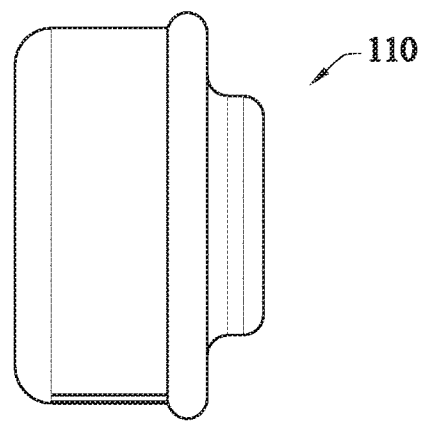
Figure 6C:
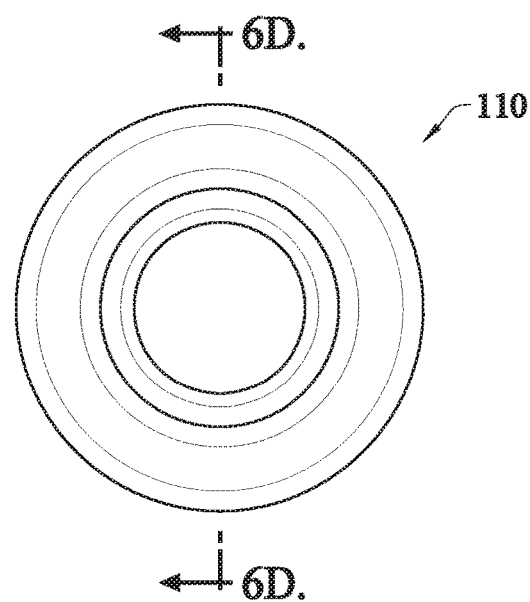
Figure 6D:
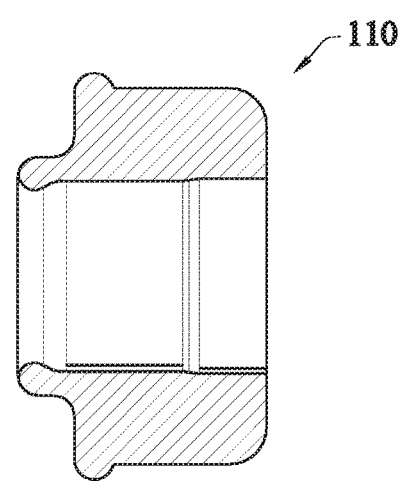
Figure 7A:
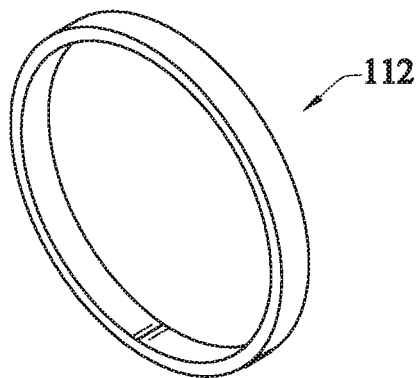
FIGS. 7A-C depict a perspective view (FIG. 7A), a side view (FIG. 7B), and a top view (FIG. 7C) a ring retainer 112—an additional retaining ring 112 to further enhance the seal between the metal and the valve silicone, as in the self-sealing valve system 100 of FIGS. 3A-D.
Figure 7B:
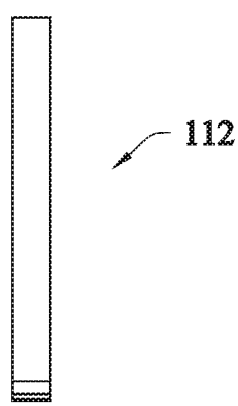
Figure 7C:
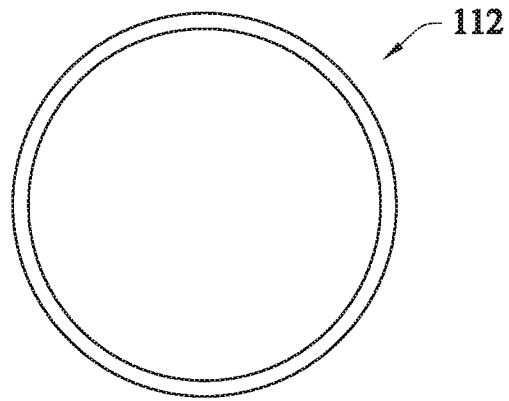

FIG. 2 illustrates an Obalon Gastric Balloon Assembly 30. The intragastric balloon 10 of the Assembly 30 is preferably provided in a deflated and folded state in a capsule 40 or other retaining, containing or coating structure ("outer container"). The outer container 40 is preferably in the form of a standard push-fit gelatin capsule, with the push-fit relied upon for containing the deflated/folded balloon; however, a gelatin wrap can advantageously be employed in certain embodiments. Gelatin is particularly preferred for use as the outer container 40; however other materials can also be suitable for use, e.g., cellulose, collagen, and the like.

Preferably, the outer container 40 has a length (longest dimension) of from about 0.95 inches (2.4 cm) to 2.5 inches (6.3 cm) and a diameter or width of from about 0.35 inches (0.9 cm) to about 0.9 inches (2.4 cm). The outer container 40 may be configured with one or more holes, slits, passageways or other egresses, preferably on each end. The process of the outer capsule 40 degrading (e.g., separates, dissolves, or otherwise opens) is expedited by pressure build up caused by inflation (inflation via catheter 50) of the balloon 10. The outer capsule 40 can be dipped in water for a brief time to soften the materials but not release the balloon 10 prior to swallowing to minimize the time lapse between swallowing and balloon inflation. The outer container is provided with a hole to house the inflation tube needle assembly (e.g., the bell-shaped needle sleeve 1000, 1200, such as is shown in FIGS. 8A-D and 10A-D), wherein the diameter of the catheter needle housing is mechanically compatible with the diameter of the outer container hole such that the needle 1100 can be inserted into the self-sealing valve 100 (see FIGS. 3A through 8D) while maintaining therein the housed balloon 10 to facilitate pushing or swallowing of the balloon assembly. In a preferred embodiment, the outer container 40 is a capsule 40. The distal half of the capsule 40 may be flared to prevent abrasion of the balloon 10 materials by the leading edge of the capsule 40 as the compacted balloon 10 is inserted into the capsule 40. The capsule 40 can also comprise two parts held together with a gel band and encompassing the folded balloon 10 that allows for quicker separation of the capsule 40 so that inflation can take place more expeditiously. The outer capsule 40 degrades (e.g., separates, dissolves, or otherwise opens) due to contact with ingested fluid ingestion (e.g., water intake) and preferably degrades within 5 minutes or less, more preferably within 2 minutes or less, so as not to cause discomfort to the patient while the balloon/catheter tube is in place.

In a preferred embodiment, the device (e.g., intragastric balloon 10) is fitted into a standard sized gelatin capsule 40. The capsule 40 may be formed of a material that has a known rate of degradation such that the balloon 10 will not be released from the capsule 40 or otherwise deployed prior to entry into the stomach 20 (see FIG. 1). For example, the capsule 40 materials may include one or more polysaccharide and/or one or more polyhydric alcohols.

Alternatively, the device, in its delivery state (e.g., the balloon 10 folded and compacted inside the capsule 40), may be coated in a substance that confines the balloon 10 in its delivery state while also facilitating swallowing. The coating may be applied by a dipping, sputtering, vapor deposition, or spraying process which may be conducted at an ambient or positive pressure. The balloon 10 may also be encapsulated by wrapping gelatin tape around the balloon 10 and then placing the wrapped balloon 10 in a capsule 40, if so desired.

In certain preferred embodiments, the encapsulated or coated device Obalon Gastric Balloon Assembly 30 is lubricated or otherwise treated so as to facilitate swallowing. For example, the encapsulated or coated device 30 may be wetted, heated, or cooled, prior to swallowing by the patient. Alternatively, the encapsulated or coated device 30 may be dipped in a viscous substance that will serve to lubricate the device's 30 passage through the esophagus. Examples of possible coatings can be any substances with lubricious and/or hydrophilic properties and include glycerin, polyvinylpyrrolidone (PVP), petroleum jelly, aloe vera, silicon-based materials (e.g. Dow 360) and tetrafluoroethylene (TFE). The coating may also be applied by a sputtering, vapor deposition or spraying process.

In additional embodiments, the coating or capsule 40 is impregnated or treated with one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

In certain embodiments, the capsule 40 may be weighted at a certain end in order for it to be oriented appropriately when it is administered, as it travels down the esophagus, and/or when it is in the stomach 20. The weighting components may include polymer materials or inflation reactants.

Intragastric Balloon

The intragastric balloon 10 of the preferred embodiments, also referred to herein as a volume-occupying subcomponent, is generally formed of a flexible material forming a wall which defines an exterior surface and an interior cavity or lumen with an inner surface. The volume-occupying subcomponent 10 can vary in size and shape according to the patient's internal dimensions and the desired outcome. The volume-occupying subcomponent 10 may be engineered to be semi-compliant, allowing the volume-occupying subcomponent 10 to stretch or expand with increases in pressure and/or temperature. Alternatively, in some embodiments, a compliant wall offering little resistance to increases in volume may be desirable.

Spherical or ellipsoidal volume-occupying subcomponents 10 are preferred in certain embodiments. Delivery, inflation and deflation of the volume-occupying subcomponent 10 may be accomplished by any of the methods described in U.S. Pat. No. 8,647,358, issued Feb. 11, 2014, or U.S. Patent Publication No. 2013/0226219, published Aug. 29, 2013, each of which is incorporated herein in its entirety.

It is advantageous in certain embodiments for the volume-occupying subcomponent 10 wall to be both high in strength and thin, so as to minimize the compacted volume of the device as it travels the esophagus of the patient. In certain embodiments, the volume-occupying subcomponent 10 wall materials are manufactured with a biaxial orientation that imparts a high modulus value to the volume-occupying subcomponent 10.

In one embodiment, the volume-occupying subcomponent 10 is constructed of a polymeric substance such as polyurethane, polyethylene terephthalate, polyethylene naphthalate, polyvinyl chloride (PVC), Nylon 6, Nylon 12, or polyether block amide (PEBA). The volume-occupying subcomponent 10 may be coated with one or more layers of substances that modify (increase, reduce, or change over time) gas-barrier characteristics, such as a thermoplastic substance.

Preferably, the gas-barrier materials have a low permeability to carbon dioxide or other fluids that may be used to inflate the volume-occupying subcomponent 10. The barrier layers should have good adherence to the base material. Preferred barrier coating materials include biocompatible poly(hydroxyamino ethers), polyethylene naphthalate, polyvinylidene chloride (PVDC), saran, ethylene vinyl alcohol copolymers, polyvinyl acetate, silicon oxide (SiOx), acrylonitrile copolymers or copolymers of terephthalic acid and isophthalic acid with ethylene glycol and at least one diol. Alternative gas-barrier materials may include polyamine-polyepoxides. These materials are commonly acquired as a solvent or aqueous based thermosetting composition and are generally spray-coated onto a preform and then heat-cured to form the finished barrier coating. Alternative gas-barrier materials which may be applied as coatings to the volume-occupying subcomponent 10 include metals such as silver or aluminum. Other materials that may be used to improve the gas impermeability of the volume-occupying subcomponent 10 include, but are not limited to, gold or any noble metal, PET coated with saran, conformal coatings and the like, as listed, for example, in Tables 1a-b, below.

In certain preferred embodiments, the volume-occupying subcomponent 10 is injection, blow or rotational molded. Either immediately following such molding, or after a period of curing, the gas-barrier coating may be applied if not already applied within the composite wall.

In another embodiment, the intragastric volume-occupying subcomponent 10 is formed using a Mylar polyester film coating silver, aluminum or kelvalite as a metallicized surface, to improve the gas impermeability of the volume-occupying subcomponent 10.

In the event that the volume-occupying subcomponent's wall is composed of multiple layers of materials, it may be necessary to use certain substances or methods to connect, attach or hold together such multiple layers. Such substances can include a solvent or an ether-based adhesive. Such multiple layers may also be heat-bonded together. Once such layers are attached together to form (for example) a sheet of material to be made into a volume-occupying subcomponent, it may also be necessary to apply additional treatment steps to such material to allow it to seal together (for example, by application of a certain degree of heat and pressure) in order to be made into a volume-occupying subcomponent 10. Accordingly, it may be advantageous to include as an additional layer in the volume-occupying subcomponent 10 certain materials that seal. For example, a volume-occupying subcomponent 10 comprised of a combination of PET and SiOx layers, which impart favorable mechanical and gas impermeability characteristics to the volume-occupying subcomponent, may be sealed by including a layer of sealable polyethylene in such volume-occupying subcomponent 10.

According to another embodiment of the preferred embodiments, the functionality of the volume-occupying subcomponent 10 and the deflation component is combined either in part or in whole. For example, the volume-occupying subcomponent 10 may be formed of a substance that is degraded within the stomach 20 over a desired period of time. Once the degradation process has formed a breach in the wall of the volume-occupying subcomponent, the volume-occupying subcomponent 10 deflates, continues to degrade and passes through the remainder of the digestive tract.

Preferably, an automated process is employed that takes a fully constructed volume-occupying subcomponent, evacuates all of the air within the interior cavity and folds or compresses the volume-occupying subcomponent 10 into the desired delivery state. For example, the evacuation of air from the volume-occupying subcomponent 10 may be actuated by vacuum or mechanical pressure (e.g. rolling the volume-occupying subcomponent). In certain embodiments, it is desirable to minimize the number of creases produced in the volume-occupying subcomponent 10 when in the delivery state.

In another embodiment, deflation of the volume-occupying subcomponent 10 may be achieved through one or more injection sites within the wall of the volume-occupying subcomponent 10. For example, two self-sealing injection sites can be incorporated at opposite sides of the volume-occupying subcomponent 10. The volume-occupying subcomponent 10 may be positioned within a fixture that employs two small-gauge needles to evacuate the air from the volume-occupying subcomponent 10.

In one embodiment, the self-sealing injection sites may further be used to insert chemical elements of the inflation subcomponent into the interior of the volume-occupying subcomponent 10. After injection of the chemical elements into the volume-occupying subcomponent, the same needles may be used to perform evacuation of the volume-occupying subcomponent 10.

It may be desirable that the volume-occupying subcomponent 10 is packed into the delivery state under, for example, a negative vacuum pressure or under a positive external pressure.

The volume-occupying subcomponent wall materials may also be engineered to, once they are initially punctured or torn, tear relatively easily from the point of such puncture or tear. Such properties can, for example, be advantageous if deflation of the volume-occupying subcomponent 10 were initiated by a tearing or puncturing of the volume-occupying subcomponent 10 wall, since such initial tear or puncture may then increase in scope, hastening and/or maximizing the deflation process.

The volume-occupying subcomponent 10 may also be coated by a lubricious substance that facilitates its passage out of the body following its deflation. Examples of possible coatings can be any substances with lubricious and/or hydrophilic properties and include glycerin, polyvinylpyrrolidone (PVP), petroleum jelly, aloe vera, silicon-based materials (e.g. Dow 360) and tetrafluoroethylene (TFE). The coating may be applied by a dipping, sputtering, vapor deposition or spraying process which may be conducted at an ambient or positive pressure.

The balloon composite wall materials can be of similar construction and composition as those described in U.S. Patent Publication No. 2010-0100116-A1, the contents of which is hereby incorporated by reference in its entirety. The materials are able to contain a fluid, preferably in compressed or non-compressed gas form, such as, e.g., $N_2$, Ar, $O_2$, $CO_2$, $SF_6$ or mixture(s) thereof, or atmospheric air (composed of a mixture of $N_2$, $O_2$, Ar, $CO_2$, Ne, $CH_4$, He, Kr, $H_2$, and Xe) that simulate gastric space concentrations. In certain embodiments, the balloon is able to hold the fluid (gas) and maintain an acceptable volume for up to 6 months, preferably for at least 1 to 3 months after inflation. Particularly preferred fill gases include non-polar, large molecule gases that can be compressed for delivery.

Prior to placement in the outer container, the balloon 10 is deflated and folded. In the inverted configuration in a deflated state, the balloon 10 is flat, with the inverted seam extending around the perimeter of the balloon 10. A self-sealing valve system 100 is affixed to the inner wall of the lumen close to the center of the deflated balloon 10. The walls of the balloon 10 are then folded. As part of the balloon 10 design, the self-sealing valve system 100 is manufactured in a manner such that it can be and is preferably placed "off center" to minimize the number of folds upon themselves (e.g., doubling or tripling up) required to fit the balloon in the outer container. For example, the self-sealing valve system 100 can advantageously be placed ½ r±¼ r from the center of the balloon, wherein r is the radius of the balloon along a line extending from the center of the balloon through the septum.

Additional description of intragastric balloons 10 and the fabrication of such, for use with the present embodiments, can be found in U.S. Pat. No. 8,162,969, issued Apr. 24, 2012, U.S. Pat. No. 9,072,583, issued Jul. 7, 2015, U.S. Pat. No. 8,647,358, issued Feb. 11, 2014, U.S. Pat. No. 8,292,911, issued Oct. 23, 2012, U.S. Pat. No. 8,202,291, issued Jun. 19, 2012, U.S. Publication No. 2013/0226219, published Aug. 29, 2013, U.S. Publication No. 2016/0310306, published Oct. 27, 2016, International Publication WO 2016/200612, published Dec. 15, 2016, U.S. Publication No. 2017/0156909, published Jun. 8, 2017, and U.S. patent application Ser. No. 15/623,175, filed Jun. 14, 2017, each of which is incorporated herein by reference in its entirety.

Tracking and Visualization Subcomponent

It may also be beneficial to implement tracking and visualization functionality into devices according to the present embodiments. Due to the non-invasive nature of the present device, physicians may desire to determine, or confirm, the location and orientation of the device prior to inflation or during the course of treatment.

A radiographic marker may be applied to the volume-occupying subcomponent 10 when the volume-occupying subcomponent 10 is in a creased or folded state such that when the volume-occupying subcomponent 10 is in its deflated state the marker appears concentrated when viewed on visualization equipment, and when the volume-occupying subcomponent 10 is inflated the marker appears less concentrated when viewed on visualization equipment. Alternatively, a marker may be applied or incorporated into the volume-occupying subcomponent 10 at multiple positions so as to facilitate identification and location of the various subcomponents of the device, such as a valve, head, or weight. The marker may be printed or painted onto a surface of the volume-occupying subcomponent 10 or between layers of the material forming the volume-occupying subcomponent 10. Alternatively, a metal coating as described below may be used as a marker to identify and/or locate the volume-occupying subcomponent 10. Metal coatings for visualizing the volume-occupying subcomponent 10 may include silver, gold, tantalum or any noble metal. Alternatively, the marker may be applied to an elastomeric sleeve that covers all or part of the volume-occupying subcomponent 10.

In another embodiment, the volume-occupying subcomponent 10 incorporates a subcomponent that changes mechanically upon inflation of the volume-occupying subcomponent, which mechanical change can be visualized using x-ray or other visualization equipment. For example, a mechanical portion of the volume-occupying subcomponent 10 containing a visualization marker may elongate upon an increase in pressure in the volume-occupying subcomponent 10.

Alternatively, a marker may be formed using a metallized mesh located between layers of the material from which the volume-occupying subcomponent 10 is constructed. The pattern or patterns formed by the imbedded marker will appear when the volume-occupying subcomponent 10 is in an inflated, deployed state.

It is envisioned that marker materials may be incorporated into the volume-occupying subcomponent 10 to facilitate various visualization techniques such as, for example, MRI, CT and ultrasound.

The volume-occupying subcomponent 10 may also contain a dye or marker that is released upon deflation to indicate that the volume-occupying subcomponent 10 cavity has been breached. Such dye or marker may, for example, be apparent in the patient's urine as an indication that the volume-occupying subcomponent 10 has begun to deflate.

In yet further embodiments, microchips and other components employing electronic modalities may be used to locate and identify a device. Microchips analogous to those utilized for the identification of pets may be used to communicate device specific information and its approximate location. For example, a Wheatstone or other bridge circuit may be incorporated into the device and, together with RF "ping and listen" technology may be used as part of a system to determine the device's approximate location and measure and communicate device specific information. Such device specific information can include internal volume-occupying subcomponent 10 pressure, which can indicate the degree of inflation of the volume-occupying subcomponent 10.

In yet further embodiments, mechanical, chemical, visual and other sensors may be included as part of the device to measure, record and/or transmit information relating to the device and/or the patient's internal environment. For example, the device may contain a camera or any of the other imaging and transmission components of a Pillcam device. As an additional example, the device may contain sensors that measure, record and/or transmit information relating to stomach pH, stomach pressure, hormone levels, organ health, and organ safety.

Self-Sealing Valve System

In preferred embodiments, a self-sealing valve system 100 is attached to the balloon (e.g., on its inside surface) that is "universal" or compatible with the swallowable catheter and a physician-assisted catheter, such as is described elsewhere herein. The valve system 100 serves to allow for balloon inflation using a miniature catheter that includes a needle assembly and also provides a mechanism for detachment of the catheter after inflation has been completed.

Figure 8A:
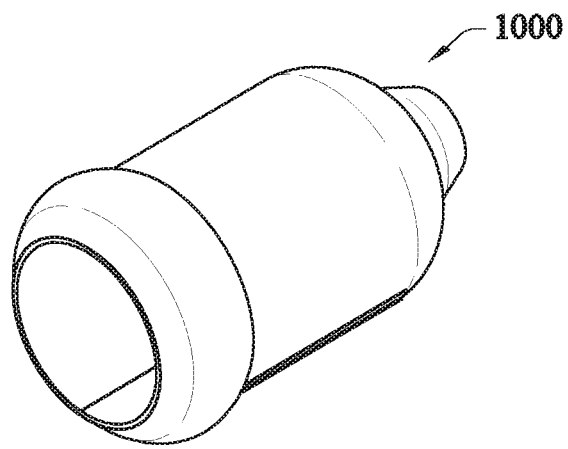
FIGS. 8A-D depict a perspective view (FIG. 8A), a side view (FIG. 8B), a top view (FIG. 8C), and a cross-sectional view (FIG. 8D) of a bell-shaped needle sleeve 1000.
Figure 8B:
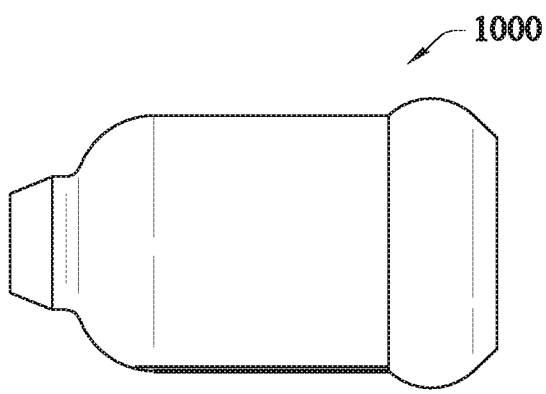
Figure 8C:
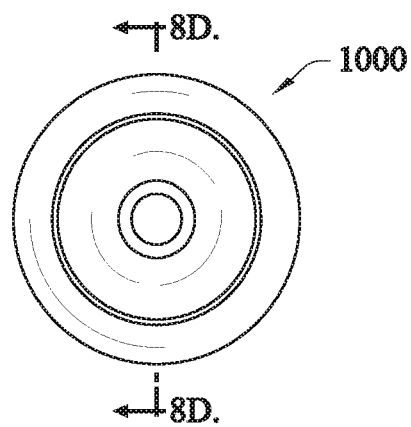
Figure 8D:
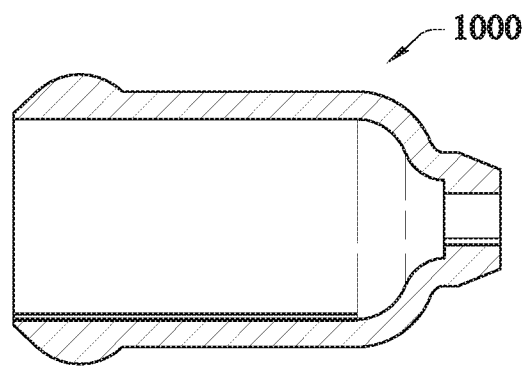

FIGS. 3A-7C and 9C depict views representing a design of a self-sealing valve system 100 which contains a self-sealing septum 114 housed within a metallic concentric cylinder or tube septum 118 along longitudinal axis A. The self-sealing valve system 100 is preferably adhered to the underside (e.g., inner surface) of the balloon material such that only a portion of the valve 100 protrudes slightly outside of the balloon surface to ensure a smooth outer surface. The septum 114 preferably consists of a material possessing a durometer of 20 Shore A to 60 Shore D. The septum 114 is inserted or otherwise fabricated into the smaller cylinder 118b of the concentric metallic retaining structure or tube septum 118 (FIGS. 3A-D) that is preferably cylindrical in shape. As shown in FIG. 8C, the smaller cylinder 118b within the larger cylinder 118a controls alignment of the catheter needle sleeve/needle assembly 54/56 with the septum 114, provides a hard barrier so that the catheter needle 56 does not pierce the balloon material (needle stop mechanism), and provides compression such that the valve/septum 100/114 re-seals after inflation and subsequent needle 56 withdrawal.

The concentric valve system 100 can also provide radio opacity during implantation and is preferably titanium, gold, stainless steel, MP35N (nonmagnetic, nickel-cobalt-chromium-molybdenum alloy) or the like. Non-metallic polymeric materials can also be used, e.g., an acrylic, epoxy, polycarbonate, nylon, polyethylene, PEEK, ABS, or PVC or any thermoplastic elastomer or thermoplastic polyurethane that is fabricated to be visible under x-ray (e.g., embedded with barium).

The septum 114 can be cone shaped, so that the compressive forces are maximized for self-sealing after inflation. The self-sealing septum 114 allows air to be evacuated from the balloon 10 for processing/compacting and insertion into the outer container 40, and allows for piercing by an inflation catheter needle 56, and then subsequent detachment of the inflation catheter 50 and withdrawal of the catheter needle 56 significantly limiting gas leakage outside of the balloon 10 during the inflation process and needle withdrawal/catheter detachment. The septum 114 is inserted into the tube septum inner cylinder 118b using a mechanical fit mechanism to provide compression. An additional ring 116 (FIG. 3D) can be placed at the distal end of the inner cylinder 118b to provide additional compression to ensure the septum material is pre-loaded so as to re-seal itself. The ring 116 ("ring stop") is preferably metallic in nature, but can also be a non-metallic polymeric material such as an acrylic, epoxy, or thermoplastic elastomer or thermoplastic polyurethane. The ring material is preferably the same material as the inner cylinder 118b, titanium, but can also be gold, stainless steel, MP35N or the like.

The larger, outer cylinder 118a (FIGS. 4A-D) of the concentric valve housing 118 ("tube septum") contains a slightly harder durometer material 110 than the inner cylinder 118b (50 Shore A or greater), but is also preferably silicone. The purpose of using a harder durometer material is to ensure sealing when connected to the needle sleeve 56 for inflation. The silicone located in the outer ring 118b of the concentric valve 118 is adhered to the balloon 10 from the inside surface. The entire outer cylinder 118a is filled and a small circular lip 111 (see FIGS. 6A-6D) of this same material is provided that is slightly larger than the diameter of the inner cylinder and extends to the outside surface of the balloon. The lip 111 is compatible with the bell-shaped needle sleeve 54 (see FIG. 9C) and provides sealing to enhance connection of the valve 100 to the catheter 50 to withstand the inflation pressures applied and also increases the ejection distance or attachment force of the catheter 50. This silicone lip 111 preferably does not protrude past the balloon surface more than 2 mm to ensure that the balloon surface remains relatively smooth and does not cause abrasion or ulcerations of the mucosa. It is designed to provide compressive forces against the needle sleeve 54 of the catheter 50 for inflation and detachment whereby when connected to the needle sleeve 54 of the inflation catheter 50, the connection coupling can preferably withstand a pressure of 35 PSI during inflation. This seal is then broken during detachment using hydraulic pressure that is preferably more than 40 PSI but less than 200 PSI to separate the coupling. An additional retaining ring 112 (FIGS. 7A-C) preferably made of the same material as concentric valve 118, can be included in the valve system 100 to further enhance the seal between the metal and the valve silicone and provide additional mechanical support to ensure proper mechanical fit and are intended to disrupt slippage of the silicone material from the hard (metallic) valve system (causing an increase in tensile force).

The valve structure uses a mechanical fit mechanism to provide the functions of the self-sealable valve 100 for inflation by the catheter 50 and subsequent catheter 50 detachment; however, primer and/or adhesive may be used to provide additional support in construction of the assembly 100. The configuration can be modified by modifying the surfaces of the metal components, making them more sticky or slippery e.g. more or less conducive to adhesion, to provide the desired mechanical/interference fit. The interference fit between the valve 100 and the catheter 50 can be modified to change the pressure requirements for inflation and/or detachment. Additional assemblies can include overmolding the metallic portions or the concentric system in silicone such that additional support rings to ensure the mechanical fit and the tensile strength and forces required to sustain the assembly during catheter inflation and detachment can be omitted.

Figure 9A:
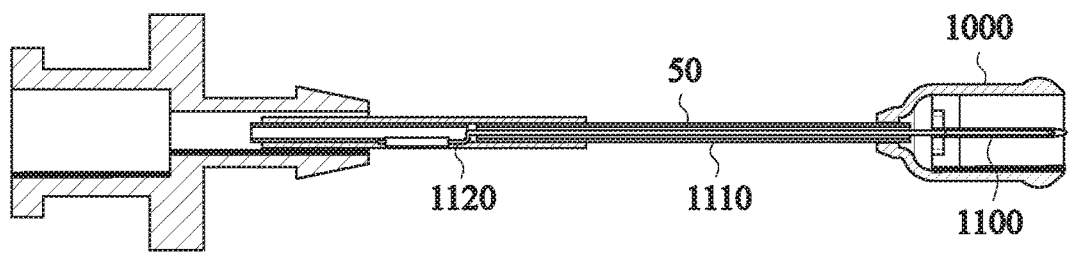
FIGS. 9A-C depict various embodiments of a single lumen catheter.
Figure 9B:
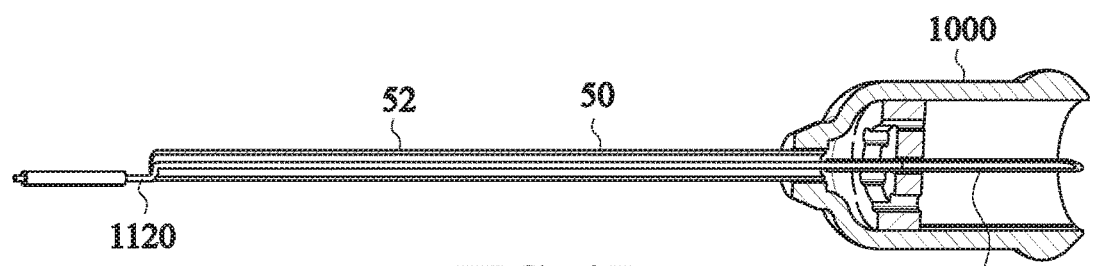
Figure 9C:
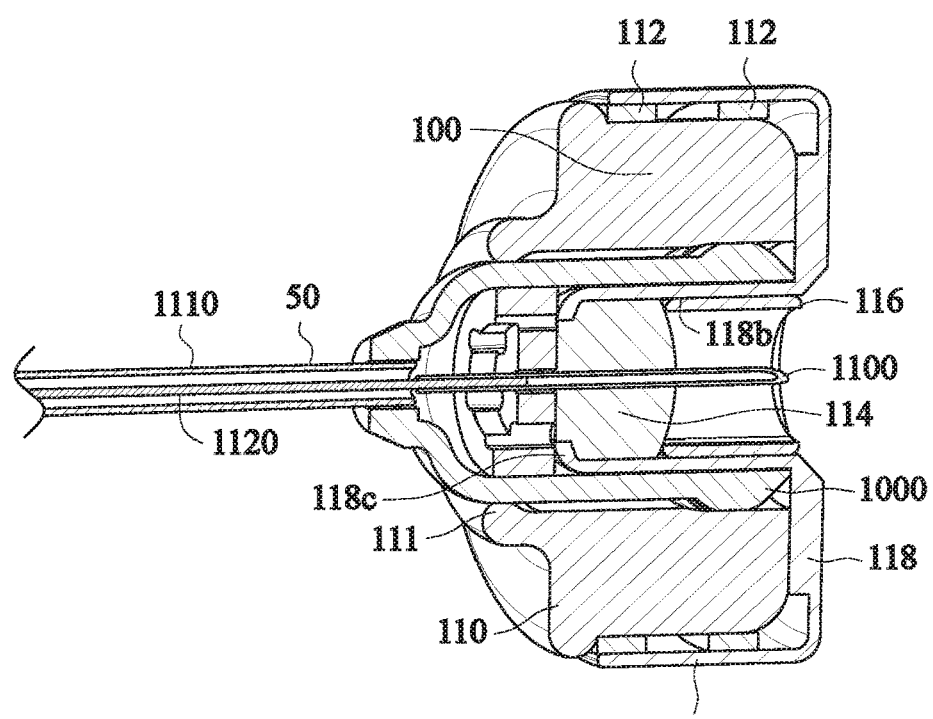
Figure 10A:
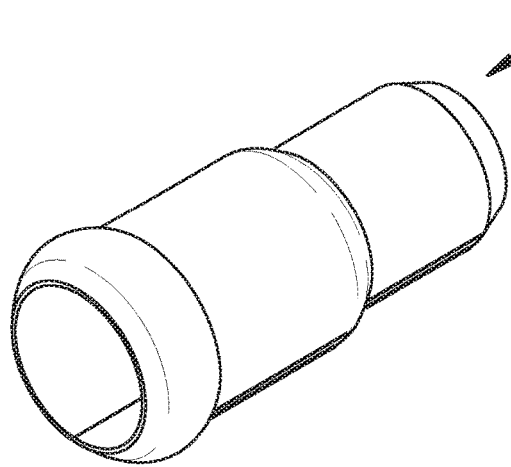
FIGS. 10A-D depict a perspective view (FIG. 10A), a side view (FIG. 10B), a top view (FIG. 10C), and a cross-sectional view (FIG. 10D) of a needle sleeve 1200 configured to accommodate a larger diameter tube.
Figure 10B:
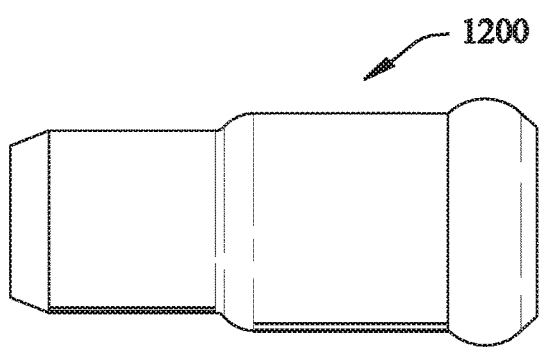
Figure 10C:
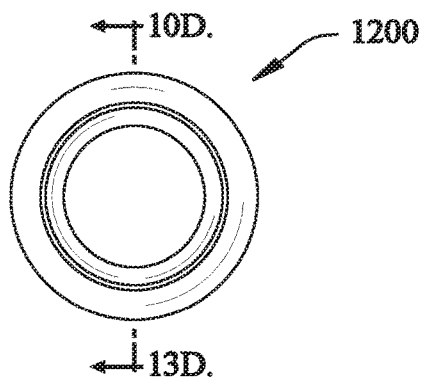
Figure 10D:
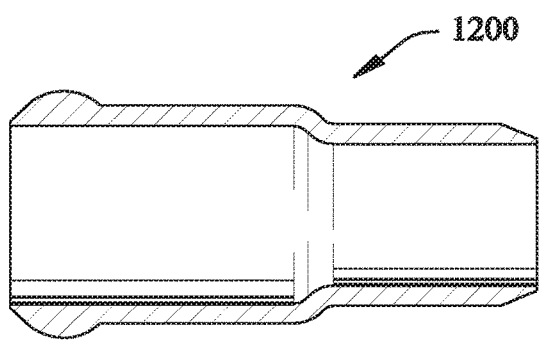

The total valve diameter is designed to fit a miniature catheter system (e.g., FIGS. 9A-9C) that does not exceed 8

French (2.7 mm, 0.105 inches) in diameter. The total diameter does not exceed 1 inch (2.54 cm) and is preferably less than 0.5 inches (1.27 cm), to facilitate swallowing. Additional valves can be added, if desired; however, it is generally preferred to employ a single valve 100 so as to maintain the volume of the deflated/folded balloon 10 (and thus the outer container 40 dimensions) as small as possible. The valve system 100 is preferably attached to the balloon 10 and bonded such that a shear force greater than 9 lbs (40 N) is required to dislodge the valve system 100.

Balloon Composite Wall

The materials selected for the composite wall of the balloon 10 may be optimized to maintain the original inflation gas without significant diffusion, or may also allow for diffusion of the gases located in the gastric environment, e.g., $CO_2$, $O_2$, argon, or $N_2$ to diffuse through the wall of the balloon 10 to inflate, partially or wholly, once the balloon 10 is placed in the stomach. A fluid (a liquid or gas) can also be added inside of the balloon 10 using the inflation catheter(s) described herein to change diffusion direction of the balloon 10 composite wall and when it reaches stasis based on the internal and external environment.

A gastric balloon 10 inflated by nitrogen, $CO_2$ gas, $SF_6$, a single fluid (gas) or a mixture of gasses employs a composite wall that provides barrier properties (fluid retention), properties imparting resistance to pH and moisture conditions in the gastric environment or the environment within the central lumen of the balloon 10, and structural properties to resist gastric motility forces, abrasion of the balloon 10 wall in vivo, and damage during manufacturing and folding of the balloon 10. Certain materials employed in the balloon 10 materials are able to withstand a hostile gastric environment designed to break down foreign objects (e.g., food particles). Some of the variables that the gastric environment encompasses are as follows: gastric liquid pH of from 1.5-5; temperature of approx. 37° C.; a relative humidity of 90-100%; ingress of gastric space gas content; and constant gastric motility external pressures of from 0-4 psi at variable frequencies and cycle times based on the fed state of the stomach. The external pressure imparted by gastric motility can also cause abrasions on the surface of the balloon 10. The inside of the balloon lumen may contain moisture from a solution injected in the balloon 10 for timing of auto-deflation or any moisture that has transferred across the membrane due to the external humid environment. In addition to these environmental stresses the wall materials meet biocompatibility requirements and are constructed such that the total thickness of the wall (barrier material) is thin enough to be compacted and placed inside of a swallowable-sized container ("outer container") without considerable damage or lodging. The outer container is small enough to transcend the esophagus (which has a diameter of approximately 2.5 cm). The wall or barrier material is also heat formable and sealable for balloon 10 construct and maintains a bond strength that can contain internal gas pressures of up to 10 psi generated by the initial inflation pressure as well as pressure due to the ingress of gas molecules from the stomach cavity until the system's gas environment reaches stasis. The film properties that are evaluated to determine suitability for use in the composite wall of the balloon 10 include pH resistance, water vapor transmission rate, gas barrier properties, mechanical strength/abrasion properties, temperature resistance, formability, flex-crack (Gelbo) resistance, surface energy (wettability) compliance, and heat bond potential.

The various layers in the composite wall can impart one or more desirable properties to the balloon 10 (e.g., fluid retention, resistance to moisture, resistance to acidic environment, wettability for processing, and structural strength). A list of polymer resins and coatings that can be combined into a multi-layer preformed system ("composite wall") is provided in Tables 1a-b. These films can be adhesively bonded together, co-extruded, or adhered via tie layers or a combination thereof to obtain the desired combination of properties for the composite wall, as discussed below. The materials identified as film coatings in Tables 1a-b are provided as coatings applied to a base polymer film, e.g., PET, Nylon, or another structural layer.

TABLE 1a

Film Resins

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM RESINS | | | |
| Polyethylene Terephthalate (PET) | X | X | |
| Polytrimethylene Terephthalate (PTT) | | | |
| Liquid Crystal Polymer (LCP) | X | X | |
| Polytrimethylene naphthalate (PTN) | X | X | |
| Polyethylene naphthalate (PEN) | X | X | |
| Polyimide (PI) | X | X | |
| Linear Low Density Polyethylene (LLDPE) | | | X |
| Ethylene Vinyl Alcohol (EVOH) | | X | |
| Polyamide: Nylon (PA) and Nylon-6 (PAG)/Nylon 12 | | X | X |
| High Density Polyethylene (HDPE) | | | X |
| Polypropylene (PP) | | | X |
| Polyurethane | | | X |
| PVDC (Saran) | | X | X |
| Polyether Block Amide (Pebax) | | | X |
| Polyvinyl Alcohol (PVOH) | | X | |
| Silicone | X | | X |

TABLE 1b

Film Coatings

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| FILM COATINGS | | | |
| Silicone Dioxide (SiO2) | | X | |
| Aluminum Oxide ($Al_2O_3$) | | X | |

TABLE 1b-continued

Film Coatings

| | Characteristics | | |
|---|---|---|---|
| | Good Structural/ Behavior/ Mechanical Strength/ Compliance | Good Fluid Retention Barrier Properties | Good Manufacturability/ Surface Energy Properties |
| Nanopolymers (Nano/Clay) | | X | |
| External Organic Coatings (e.g., epoxy amine) | | X | |
| Inorganic Coatings (e.g., Amorphous Carbon) | | X | |
| Oxygen Scavengers | | X | |
| Parylene C | | X | |

Fluid Retention Layers

In preferred embodiments, a blended polymer resin using multiple layers is employed to maintain the inflated balloon's shape and volume by retaining the inflation fluid for the duration of the intended use. Certain barrier films, widely used in the food packaging and plastic bottling industries, can advantageously be employed for this purpose in the composite wall of the balloon 10. Preferably, the barrier materials have a low permeability to carbon dioxide (or other gases, liquids, or fluids that are alternatively or additionally used to inflate the volume-occupying subcomponent). These barrier layers preferably have good adherence to the base material. Preferred barrier coating materials and films include polyethylene terephthalate (PET), linear low density polyethylene (LLDPE), ethylene vinyl alcohol (EVOH), polyamides such as Nylon (PA) and Nylon-6 (PA-6), polyimide (PI), liquid crystal polymer (LCP), high density polyethylene (HDPE), polypropylene (PP), biocompatible poly(hydroxyamino ethers), polyethylene naphthalate, polyvinylidene chloride (PVDC), saran, ethylene vinyl alcohol copolymers, polyvinyl acetate, silicon oxide (SiOx), silicon dioxide ($SiO_2$), aluminum oxide ($Al_2O_3$), polyvinyl alcohol (PVOH), nanopolymers (e.g., nanoclay), polyimide thermoset film, EVALCA EVAL EF-XL, Hostaphan GN, Hostaphan RHBY, RHB MI, Techbarrier HX (SiOx-coated PET), Triad Silver (silver metallized PET), Oxyshield 2454, Bicor 84 AOH, acrylonitrile copolymers, and copolymers of terephthalic acid and isophthalic acid with ethylene glycol and at least one diol. Alternative gas-barrier materials include polyamine-polyepoxides. These materials are typically provided as a solvent-based or aqueous-based thermosetting composition and are typically spray-coated onto a preform and then heat-cured to form the finished barrier coating. Alternative gas barrier materials that can be applied as coatings to the volume-occupying subcomponent include metals such as silver or aluminum. Other materials that may be used to improve the gas impermeability of the volume occupying subcomponent include, but are not limited to, gold or any noble metal, PET coated with saran, and conformal coatings.

One method that is used in the packaging industry to delay diffusion of the inflation fluid is to thicken the material. Thickening the material is generally not preferred, as the total composite wall thickness preferably does not exceed 0.004 inches (0.010 cm) in order for the balloon 10 to be foldable into the desired delivery container size for swallowing by a patient.

A multilayer polymer film that is able to withstand the gastric environment over the course of the usable life of the balloon 10 includes linear low-density polyethylene (LLDPE) adhesively bonded to a Nylon 12 film. Alternatively, an additional film layer with barrier properties, such as PVDC can be added to the composite wall.

The layers providing gas barrier properties are preferably situated as inner layers in the composite wall as they are less mechanically robust than resins that are considered "structural" such as Nylon and the like.

Structural Layers

Layers such as polyurethane, Nylon, or polyethylene terephthalate (PET) can be added to the composite wall for structural purposes, and are preferably placed as outermost (proximal to the gastric environment or proximal to the central lumen of the balloon 10) layers, provided that the pH resistance of such layers can withstand the acidic environment of the stomach 20 or the central lumen of the balloon 10.

Fabrication of the Composite Wall

The various layers of the composite wall, including the gas barrier layers, need not be situated in any particular order, but those of superior resistance to acidity, temperature, mechanical abrasion, and superior biocompatibility profile are preferably employed as layers contacting the gastric environment. Those with superior resistance to, e.g., acidity and temperature, are preferably employed as layers contacting the central lumen of the balloon 10.

The various layers of the wall can include a single layer or up to 10 or more different monolayers; however, a film thickness of from 0.001 inches (0.0254 cm) to 0.004 inches (0.010 cm) thick is desirable such that the resulting balloon 10 compacted to fit into a swallowable capsule. The resulting composite wall preferably has good performance specifications with respect to each category listed in Tables 1a-b.

Films that are co-extruded are advantageously employed, as some adhesives may contain leachables that are undesirable from a biocompatibility perspective. In addition, coextrusion allows for better blending such that the materials maintain their original properties when combined in this fashion and are less likely to be subject to delamination when exposed to gastric motility forces.

Combining films with similar properties, e.g., two film layers with excellent gas barrier properties, in a composite wall is advantageous for use in a gastric balloon 10 containing nitrogen, oxygen, $CO_2$ or a mixture thereof as the inflation gas or where the external environment the product is to be placed in, contains a mixture of gases including $CO_2$, e.g., the stomach. A primary advantage of such composite films is that restrictions on film thickness can be observed without sacrifice of gas barrier properties. Such a configuration also contributes to reducing the effects of processing damage (e.g., manufacturing and compacting) and damage due to exposure to in vivo conditions (e.g., gastric motility forces).

In a particularly preferred embodiment, the composite wall includes a plurality of layers. The first layer is an outer protective layer that is configured for exposure to the gastric environment. This layer is resistant to mechanical forces, exposure to water (vapor), abrasion, and high acidity levels. Nylon or more specifically, Nylon 12 is particularly preferred for the layer exposed to the gastric environment, and is especially resistant to mechanical forces.

In an alternative embodiment, polyurethane is RF welded to saran to yield a 6-7 mil thick composite wall. In another embodiment, a five-layer system is provided comprising a layer of saran sandwiched between two polyurethane layers.

Between the saran layer and each of the polyurethane layers is a tie layer. The layers can be welded together, co-extruded or adhered using an adhesive. This tri-layer is then co-extruded to Nylon on each side, and then a final sealing layer (polyethylene or the like) is added to one of the nylon layers for the total composite wall. A representative example of material combinations that are commercially available or manufacturable is provided in Table 2. The orientation of the layers (innermost—in contact with the central balloon 10 lumen, or outermost—in contact with the gastric environment) is also indicated if more than two layers are described to support a suggested composite wall.

Most of the film resins listed in Table 2 provide some degree of gas barrier properties. Therefore, many can be used solely to form the balloon 10 wall as a monolayer film; however, they can also be used in conjunction with other film resins to meet the desired gas retention and mechanical specifications for the useful life of the balloon 10 based on the inflation gas and external environment the balloon 10 is to be placed in. These film resins can also be coated with gas barrier coatings listed in Tables 1a-b. Additional film layers can be added to form the total composite wall. While such additional layers may not impart substantial barrier properties, they can provide structural and/or mechanical properties, protection for the other layers of the composite wall that are susceptible to water vapor, humidity, pH, or the like, or other desirable properties. The film layers can be assembled using various adhesives, via co-extrusion, via lamination, and/or using tie layers and such to create a composite wall that meets the requirements of an intragastric balloon 10 suitable for use for at least 25 days, or up to 90 days or more, with the specified gas retention properties. Table 2 provides a list of layers and layer combinations suitable for use in composite walls for an intragastric balloon 10. The composite description, resin abbreviation, configuration (single layer, bilayer, trilayer, or the like) and trade name of commercially available combinations are listed. The number of layers indicated does not include any adhesive layers or tie layers used to fabricate the composite wall, such that a 6-layer composite wall may, for example, have two or three adhesive layers and/or tie layers that make up the total composite wall, and therefore the total number of layers can be eight or nine in final form. The term "layer" as used herein is a broad term, and is to be given its ordinary and customary meaning to a person of ordinary skill in the art (and is not to be limited to a special or customized meaning), and refers without limitation to a single thickness of a homogenous substance (e.g., a coating such as SiOx, or a layer such as PET), as well as to a supporting layer having a coating thereon (wherein a "coating" is, e.g., a material typically employed in conjunction with substrate that provides structural support to the coating layer). For example, a PET-SiOx "layer" is referred to herein, wherein a layer of Si-Ox is provided on a supporting PET layer.

TABLE 2

| Example Film Composite Walls* | Abbreviation | Trade name |
| --- | --- | --- |
| polyethylene terephthalate | PET | Mylar |
| metallized oriented polyethylene terephthalate | metallized OPET | Custom |
| polyvinyl alcohol coated oriented polypropylene | PVOH coated OPP | Bicor |
| metallized biaxially oriented nylon 6 | metallized OPA6 | Custom |
| Biaxally oriented Nylon/ethylene vinyl alcohol/biaxally oriented Nylon | OPA/EVOH/OPA | Honeywell Oxyshield Plus |
| Nylon/ethylene vinyl alcohol/Low Density Polyethylene | Nylon/EVOH/LDPE | Custom |
| polyvinylidene chloride coated oriented polyethylene terephthalate | PVDC/OPET | Mylar |
| polyvinylidene chloride coated oriented polypropylene | PVCD/OPP | Custom |
| polyvinylidene chloride coated biaxally oriented Nylon 6 | PVCD/OPA6 | Honeywell Oxyshield |
| high density polyethylene/ethylene vinyl alcohol | HDPE/EVOH | Custom |
| polypropylene/ethylene vinyl alcohol laminate | PP/EVOH | Custom |
| polyethylene terephthalate/ethylene vinyl alcohol | PET/EVOH | Custom |
| metallized oriented polypropylene | metallized OPP | Custom |
| sealable PVDC coated oriented polypropylene | PVDC coated PP | Custom |
| polyvinylidene fluoride | PVDF | Custom |
| Polyvinyl chloride | PVC | Custom |
| polyvinyl fluoride | PVF | Tedlar |
| polychlorofluoroethylene | PCTFE | ACLAR UltRx, SupRx, Rx |
| amine-based epoxy coated Nylon | epoxy coated PA6 | Bairocade |
| polyvinyl chloride-polyvinylidene chloride copolymer | PVC-PVDC | Custom |
| medium density polyethylene | MDPE | Custom |
| Nylon/Polypropylene | Nylon/PP laminate | Custom |
| Nylon-High Density Polyethylene | Nylon-HDPE laminate | Custom |

TABLE 2-continued

| Example Film Composite Walls* | Abbreviation | Trade name |
|---|---|---|
| Nylon 12/Ethyl Methyl Acrylate/Polyvinylidene Chloride/Ethyl Methyl Acrylate/Nylon 12/Linear Low Density Polyethylene+Low Density Polyethylene | Co-extruded Nylon 12-encapsulated PVDC-Nylon 12-LLDPE+LDPE | Custom Co-extruded blend |
| Multi-layer Nylon 12/Linear Low Density Polyethylene+Low Density Polyethylene | Co-extruded multi-layer Nylon 12-LLDPE+LDPE | Custom Co-Extruded Blend |
| acetylene plasma coating on polyester | PET/A | Custom |
| difluoroethylene coating on polyethylene terephthalate | PET/DA | Custom |
| oriented polypropylene | OPP | Custom |
| cast propylene | CPP | Custom |
| high density polyethylene | HDPE | Custom |
| cyclic olefin copolymer | COC | Custom |
| oriented polystyrene | OPS | Custom |
| Fluorinated Ethylene Propylene | FEP | Custom |
| difluoroethylene coating on low density polyethylene | LDPE/D | Custom |
| difluoroethylene coating on polypropylene | PP/D | Custom |
| acetylene plasma coating on polypropylene | PP/A | Custom |
| acetylene plasma coating on low density polyethylene | LDPE/A | Custom |
| polybutylene terephthalate polyether glycol copolymer | TPC-ET | Hytrel |
| polyether block amide TPE | PEBA | Pebax |
| oxide coated biaxally oriented Nylon | oxide coated PA | Honeywell Oxyshield Ultra |
| Nanoclay/nylon | MXD6/Nanoclay | Imperm/Aegis OXCE |
| Polyethylene Terephthalate/Silicone Dioxide | PET/SiOx | BestPET/TechBarrier |
| Polyethylene Terephthalate/Oxygen scavengers | PET+O2 Scavengers | MonoxBar |
| Modified Polyethylene Terephthalate | Modified PET | DiamondClear |
| Polyethylene Terephthalate/Nylon 6 | PET/MXD6 | HP867 |
| Amorphous polyvinyl alcohol | Amorphous PVOH | Nichigo G-Polymer |
| Nylon 6/Ethyl vinyl alcohol/Linear Low Density Polyethylene | Nylon 6/EVOH/LLDPE | Custom |
| Ethyl vinyl alcohol/Poly-Propylene/Ethyl vinyl alcohol | EVOH/PP/EVOH | Custom |
| Ethyl vinyl alcohol/Nylon | EVOH/Nylon | Custom |
| Polyethylene/Ethyl vinyl alcohol/Polyethylene | PE/EVOH/PE | Custom |
| Polyethylene/Ethyl vinyl alcohol/Polyethylene Terephthalate | PE/EVOH/PET | Custom |
| Silicon dioxide-coated Polyethylene Terephthalate/Linear Low Density Polyethylene/Ethyl vinyl alcohol/Linear Low Density Polyethylene | PET-SiOx/LLDPE/EVOH/LLDPE | Custom |
| Aluminum Oxide-coated Polyethylene Terephthalate/Polyethylene | PET-AL$_2$O$_3$/LLDPE | Custom |
| Polyethylene/Ethyl vinyl alcohol/Linear Low Density Polyethylene | PE/EVOH/LLDPE | Custom |
| Polyethylene Terephthalate/Polyethylene/Polyethylene/Biaxially oriented Ethyl vinyl alcohol | PET/PE/OEVOH/PE | Custom |
| Polyethylene Terephthalate/Polyethylene/Ethyl vinyl alcohol/Ethyl vinyl alcohol/Ethyl vinyl alcohol/Polyethylene | PET/PE/EVOH/EVOH/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |

TABLE 2-continued

| Example Film Composite Walls* | Abbreviation | Trade name |
|---|---|---|
| Silicone dioxide-coated Polyethylene Terephthalate/Polyethylene/Ethyl vinyl alcohol/Polyethylene | PET-SiOx/PE/EVOH/PE | Custom |
| Polyethylene/Ethyl vinyl alcohol/polyvinylchloride | PE/EVOH/PVDC | Custom |
| Polyethylene Terephthalate/Linear Low Density Polyethylene/Ethyl vinyl alcohol/Linear Low Density Polyethylene | PET/LLDPE/EVOH/LLDPE | Custom |
| Kurrarister C-coated Polyethylene Terephthalate/Polyethylene/Ethyl vinyl alcohol/Polyethylene | PET-Kurrarister-C/PE/EVOH/PE | Custom |
| Polyethylene Terephthalate/Polyethylene/Nylon 6/Ethyl vinyl alcohol/Nylon 6/Polyethylene | PET/PE/Nylon 6/EVOH/Nylon 6/PE | Custom |
| Nylon 6/Ethyl vinyl alcohol/Polyvinylchloride/Low Density Polyethylene | Nylon 6/EVOH/PVDC/Nylon 6/LDPE | Custom |
| Polyimide | PI | Custom |
| Polyimide/Linear Low Density Polyethylene | PI/LLDPE | Custom |
| Polyimide/Polyvinylchloride | PI/PVdC | Custom |
| Polyimide/Polyvinylchloride/Linear Low Density Polyethylene | PI/PVdC/LLDPE | Custom |

In particularly preferred embodiments, the composite wall has a thickness of 0.005 inches or less (5.0 mil or less); however, in certain embodiments a thicker composite wall may be acceptable. Generally, it is preferred that the composite wall have a thickness of no more than 0.004 inches (4.0 mil).

Fabrication of the Balloon

To ensure good mechanical strength of the balloon 10, the balloon 10 is preferably formed and sealed such that the edges of the pieces used to form the balloon 10 are overlapping. This can be accomplished by any suitable method. For example, two flat sheets of material can be placed in a frame with magnetized edges to hold the two sheets in place. Slack can be added to the piece of film to orient the material such that it maintains its properties after the forming process. The frame can be placed over a mold that represents a hemisphere the balloon 10. The material, with slack put in it prior to pressure being applied, re-orients the material such that it is more evenly distributed around the hemisphere shape. The material is preferably thickest in the middle and is made thinner on the sides where it will be welded to a second piece to create a sphere or ellipsoid having a substantially uniform wall thickness. For example, starting with a 0.0295" film, the middle of the film or subsequent apex has an ending film thickness of 0.0045" and the edges have an ending thickness of 0.0265" for subsequent overlapping during the welding process.

The valve can be adhered to the (e.g., polyethylene, PE) side of one of the hemispheres and protrude out of the opposite (e.g., nylon) side. One hemisphere typically consists of Nylon as the outermost layer and the second hemisphere typically has polyethylene (sealing web) as the outermost layer. The edges of the two hemispheres are preferably aligned such that they overlap by at least 1 mm and no more than 5 mm. Alignment and overlay of the two hemispheres is done to compensate for the thinning at the edges during the thermoforming process, which in turn inhibits seam bursts in vivo. Each half of the spheroid is placed on a fixture and the excess from the forming process is trimmed. On a multi-layer film, the sealing layer, a PE or similar layer is bonded to the sealing layer of the second film half. To do this the film of the hemisphere that has the nylon exposed to the external environment is folded up along the edges of the sphere on one half such that it can be bonded to the hemisphere with the polyethylene on the outermost layer.

The two film pieces are then sealed using a roller bonder or a band heater. In the roller bonder, a pneumatic cylinder provides the compression, the heater provides the sealing heat, and a motor that moves the bonder around the area controls the time that is required to ensure proper sealing. In the band heater, there is a heating element, an expandable plug that provides the compression, and a timer. The band is a metal, preferably copper and a spool-like fixture provides the compression needed. Using film layers of different melt temperatures helps ensure integrity of the barrier layers of the final balloon 10 configuration. If two similar materials are welded, then an insulator can be employed. In a preferred embodiment, one sphere is provided with the Nylon layer facing out and the second sphere has a PE layer facing out.

Balloons with Resistance to Spontaneous Deflation

The largest percentage of intragastric balloon malfunctions is due to spontaneous deflations. Spontaneous deflations can occur due to (1) external puncture of the intragastric balloon 10 due to gastric motility forces, (2) over inflation of the balloon 10 due to increased internal pressure of the balloon 10 from uptake of the gastric environment of the gasses and water vapor and (3) under inflation of the balloon 10 that leads to fatiguing of the excess material and subsequent puncture of the balloon 10. By managing these two variables and tuning these variables to withstand the dynamic gastric environment, the balloon system can be tailored to ensure it remains inflated throughout its useful life. Instances of spontaneous deflation in this intragastric balloon 10 can be minimized by selection of the starting inflation gas in conjunction with selection of the composite wall materials and construction. Selection of the permeability characteristics with respect to water vapor transmission and gas permeability of the composite wall so as to take advantage of the properties of the gastric space contents can enable the rate of diffusion of gases into and out of the balloon 10 to be controlled. This method allows for a tunable method for prevention of under inflation and over inflation.

Another phenomenon seen with gastric balloons 10 and obesity in general is stomach accommodation. In the process of stomach accommodation, the stomach 20 grows to accommodate the space occupying device or excess food that is ingested. In the process of stomach accommodation, the volume of a stomach 20 containing an intragastric balloon 10 grows over time, such that the patient becomes hungrier. However, by controlling gas diffusion and water vapor transmission across the balloon wall over time, the balloon size can also be increased over time by selecting the starting inflation gas(es) and water and other in vivo gas permeability characteristics of the film so as to maintain weight loss. In addition to spontaneous deflations, selecting the permeability characteristics of the composite wall in conjunction with the starting gases and utilizing the transfer of gases and water inside of the balloon 10 from the gastric environment, the balloon 10 can be designed to grow over its useful life in response to stomach accommodation.

Experiments were performed wherein various starting inflation gases were selected in conjunction with varying external gas environments that mimic the stomach gas and water environment in vivo. The stomach environment consists of water, acid (hydrochloric acid), a mixture of gases, and chyme (the semifluid mass of partly digested food expelled by the stomach 20 into the duodenum). Stomach gas usually arises from swallowing air during eating. The composition of air is nitrogen ($N_2$) 78.084%; oxygen ($O_2$) 20.9476%; argon (Ar) 0.934%; carbon dioxide ($CO_2$) 0.0314%; neon (Ne) 0.001818%; methane ($CH_4$) 0.0002%; helium (He) 0.000524%; krypton (Kr) 0.000114%; hydrogen ($H_2$) 0.00005%; and xenon (Xe) 0.0000087%.

Five gases constitute greater than 99% of the gases in gastrointestinal system: $N_2$, $O_2$, $CO_2$, $H_2$ and methane, with nitrogen predominating. Gastric $pCO_2$ closely parallels local (splanchnic) arterial and draining venous blood $pCO_2$ values. Neutralization of stomach acid can also generate gas. For example, when the stomach acid reacts with bicarbonates (e.g., as are present in certain antacids) in the digestive juices, the chemical process creates $CO_2$, which is normally absorbed into the blood stream. Digestion of food in the intestines, mainly through fermentation by colonic bacteria, generates $CO_2$, $H_2$, and methane. Microbes appear to be the sole source of all of the hydrogen and methane produced in the intestine. These arise from fermentation and digestion of nutrients (polysaccharides from fruits and vegetables are not digested in the small intestines). Small quantities of a few other gases, including hydrogen sulfide, indoles, and ammonia can also be generated.

Controlled self-inflation of the intragastric balloon 10 in the in vivo environment can be achieved by using a semipermeable or permeable composite wall in the balloon 10 and initially filling the balloon 10 with a preselected single gas, such as $N_2$ or $O_2$. The balloon 10 utilizes differences in concentrations of gases and water concentration differences between the internal balloon 10 environment and the external environment in vivo (GI/stomach) to increase and/or decrease the volume and/or pressure over time. To achieve a controlled decrease in volume and/or pressure, a wall can be employed that has a relatively higher permeability to the single gas used to inflate the balloon 10 than to other gases present in the in vivo gastrointestinal environment. For example, if nitrogen gas is employed as the inflation gas, over time in the in vivo environment, the volume and/or pressure in the balloon 10 will decrease as nitrogen diffuses out into the in vivo environment through the oxygen permeable wall. Similarly, if oxygen gas is employed as the inflation gas, over time in the in vivo environment, the volume and/or pressure in the balloon 10 will decrease as oxygen diffuses out into the in vivo environment through the oxygen permeable wall. The differential in partial pressure of the single gas in the balloon 10 (higher) versus the in vivo environment (lower) will drive the process until equilibrium or homeostasis is reached. To achieve a controlled increase in volume and/or pressure, a wall can be employed that has a relatively lower permeability to the single gas used to inflate the balloon 10 than to other gases present in the in vivo gastrointestinal environment. For example, if nitrogen gas is employed as the inflation gas, over time in the in vivo environment, the volume and/or pressure in the balloon 10 will increase as $CO_2$, etc. diffuses into the balloon 10 through the $CO_2$ permeable wall. The differential in partial pressure of the permeable gas in the balloon 10 (lower) versus the in vivo environment (higher) will drive the process until equilibrium is reached.

In addition, maintaining and/or controlling inflation of the balloon 10 can also be done using the differences in concentrations between the internal balloon 10 environment and external gastric environment in which the balloon 10 volume/pressure can be increased or decreased as needed to extend the useful life of the product. One reason to decrease the pressure can be to first inflate the balloon 10 with a large, but highly diffusible/soluble gas molecule such as $CO_2$ in addition to a more inert gas like nitrogen to pre-stretch the balloon, with the soluble gas diffusing out of the balloon 10 and other gases not originally present in the balloon 10 migrating in to fill the balloon.

Inflation gases can be selected to start with the majority of the gas in the balloon 10 comprising a large, inert gas or a gas that has low diffusivity through the selected composite wall. An inert gas in conjunction with a less inert gas(es) that are more soluble in the gastric environment, can be combined to comprise the starting balloon 10 inflation gas composition. Patient diet and medications can also affect/control balloon 10 inflation status—primarily by $CO_2$ concentration effects produced in the gastric environment. In addition, gastric pH also affects $CO_2$ concentration. This particular method can also allow for a greater degree of tuning of the device's useful life based on the composite wall material, e.g., barrier/non-barrier and whether the gas that diffuses in is maintained longer in the balloon 10 if it has a barrier wall versus a non-barrier wall. This particular form of self-inflation can be employed using a self-inflating gastric balloon 10 (e.g., initially inflated by a gas generating reaction in the balloon 10 initiated after swallowing), or an inflatable gastric balloon 10 (e.g., inflated using a catheter, with or without endoscopic assistance, delivered nasogastrically or any other delivery method). The method can be used with any gastric balloon, including swallowable balloons and balloons placed in the stomach 20 by, e.g., endoscopic methods. The method is particularly preferred for use in connection with intragastric devices; however, it can also be applied to use in, e.g., pulmonary wedge catheters and urinary incontinence balloon 10 devices. The advantages to this technology include the ability to compensate for stomach accommodation, allowing the balloon 10 to adapt to a stomach 20 that may increase in volume over time, thereby maintaining patient satiety. It also permits starting with a smaller amount of inflation gas constituents for a self-inflating balloon. It can prevent spontaneous deflations by utilizing diffusion gradients between gastric balloon systems and the in vivo gastric environment.

In a particularly preferred embodiment, used in connection with $N_2$ (with or without $CO_2$) as the inflation agent, a multi-layer co-extruded blend for the wall layers is employed. A particularly preferred configuration is Nylon 12/Ethyl Methyl Acrylate/Polyvinylidene Chloride/Ethyl Methyl Acrylate/Nylon 12/Linear Low-Density Polyethylene+Low Density Polyethylene (also referred to as co-extruded Nylon 12-encapsulated PVDC-Nylon 12-LLDPE+LDPE multilayer). Another particularly preferred configuration is a co-extruded multi-layer Nylon 12/Linear Low-Density Polyethylene+Low Density Polyethylene. Selection of the resins for the composite wall construction (as well as selection of using a coextrusion method or adhesives) can be varied to control compliance (stretchiness), puncture resistance, thickness, adhesion, sealing bond strength, orientation, acid resistance, and permeability characteristics to gasses and water vapor to achieve a particular effect.

Intragastric Balloon Inflation Systems

An inflation system for inflating the inflatable intragastric balloon 10 is provided. The system includes inflation tubing, such as described with relation to FIGS. 2, 9A-C, 17, 24 and 26, a source of inflation fluid, such as is described with respect to FIGS. 11, 12, 11-11B and 19, and an inflation fluid dispenser, such as but not limited to as described with respect to FIGS. 16A-48. Additional description of intragastric balloon inflation systems can be found in U.S. Pat. No. 8,162,969, issued Apr. 24, 2012, U.S. Pat. No. 9,072,583, issued Jul. 7, 2015, U.S. Pat. No. 8,647,358, issued Feb. 11, 2014, U.S. Pat. No. 8,292,911, issued Oct. 23, 2012, U.S. Pat. No. 8,202,291, issued Jun. 19, 2012, U.S. Publication No. 2013/0226219, published Aug. 29, 2013, U.S. Publication No. 2016/0310306, published Oct. 27, 2016, International Publication WO 2016/200612, published Dec. 15, 2016, U.S. Publication No. 2017/0156909, published Jun. 8, 2017, and U.S. patent application Ser. No. 15/623,175, filed Jun. 14, 2017, each of which is incorporated herein in its entirety.

Inflation Assembly

In certain preferred embodiments, the volume-occupying subcomponent is filled or inflated with a fluid using tubing which is subsequently detached and pulled away from the volume-occupying subcomponent. One end of the volume-occupying subcomponent has a port connected to tubing of sufficient length that when unwound can span the entire length of the esophagus, from mouth to stomach. This tubing is connected to the volume-occupying subcomponent with a self-sealable valve or septum that can tear away from the volume-occupying subcomponent and self-seal once the volume-occupying subcomponent is inflated. A physician or other health care professional secures one end of the tubing as the patient swallows the device. Once the device is residing within the stomach, the physician uses the tube to transmit a fluid, such as air, nitrogen, other gas(es), saline solution, pure water, or the like, into the volume-occupying subcomponent and thereby inflate it. After the volume-occupying subcomponent is fully inflated, the tubing is released and can be pulled out from inside the patient.

The tube may be released in a number of manners. For example, the tubing may be detached by applying a gentle force, or tug, on the tubing. Alternatively, the tubing may be detached by actuating a remote release, such as a magnetic or electronic release. Additionally, the tubing may be released from the volume-occupying subcomponent by an automatic ejection mechanism. Such an ejection mechanism may be actuated by the internal pressure of the inflated volume-occupying subcomponent. For example, the ejection mechanism may be sensitive to a specific pressure beyond which it will open so as to release any excess pressure and simultaneously release the tube. This embodiment provides a desirable feature through combining release of the tubing with a safety valve that serves to avert accidental over inflation of the volume-occupying subcomponent in the patient's stomach.

In certain embodiments, it may also be advantageous for the volume-occupying subcomponent to inflate gradually or in several steps over time. For example, if gas escapes the volume-occupying subcomponent prior to the desired deflation time, it can be beneficial for the device to re-inflate in order to preserve it in its expanded state.

Inflation Tubing

Referring to FIGS. 2, 9A-9C and 24, an intragastric balloon system 1915, 30 that is manually inflated by a miniature catheter 50, 1110 can be employed in certain embodiments. The system preferably remains "swallowable." The balloon 10 for delivery is in a compacted state and is attached to a flexible, miniature catheter 50, 1110, preferably no larger than 4 French (1.35 mm) in diameter. The catheter 50, 1110 is designed such that a portion of the catheter 50, 1110 can be bundled or wrapped upon itself for delivery with the encapsulated balloon 10, allowing the patient to swallow both catheter 50, 1110 and balloon 10 for delivery to the stomach 20 (see FIG. 1). The balloon 10 can contain a self-sealable valve system 100 (see FIGS. 3A-3D) for attachment of the catheter 50, 1110 (see FIG. 9C) and inflation of the balloon 10 once it reaches the stomach cavity. The proximal end of the catheter 50, 1110 can be left just outside of the patient's mouth, permitting connection to an inflation fluid dispenser that can house the preferred inflation fluid (gas or liquid). After inflation, the catheter 50, 1110 can be detached from the balloon valve 100 and pulled back through the mouth. This method allows for the intragastric balloon 10 to maintain its swallowability but allow for inflation by a fluid source or a mixture of fluid sources via the catheter 50, 1110. Alternatively, a more rigid, pushable system can be employed wherein the balloon valve 100 is compatible with either the swallowable, flexible catheter 50, 1110 or the pushable, rigid catheter assembly.

The inflation catheters 50, 1110 (swallowable or administrator-assisted pushable) described herein are configured to deliver the balloon device 1915, 30 orally and without any additional tools. The administration procedure does not require conscious sedation or other similar sedation procedures or require endoscopy tools for delivery. However, other versions of the device 1915, 30 can be used in conjunction with endoscopy tools for visualization or can be adapted such that the balloon device 30 can be delivered nasogastrically as well.

In operation, the proximal end of the inflation catheter 50, 1110 is connected to a valve or connector that allows for connection to the inflation source or the inflation fluid dispenser. The connector materials may consist of polycarbonate or the like and can connect to a single or multi-lumen catheter tube 1100, such as is known in the art. The distal end of the inflation catheter 50, 1110 is connected to the self-sealing inflation valve system 100 of the balloon 10 that has been compacted and housed within a gelatin capsule 40 or compacted using gelatin bands (FIG. 2). The catheter tube 1100 is preferably from 1 French (0.33 mm) to 6 French (2 mm) in diameter. The catheter 50, 1110 is preferably long enough to extend out past the mouth (connected to the inflation connector or valve) and transverse the esophagus down to at least the middle of the stomach 20—approximately 50-60 cm. Measurement ticks can be added to the tubing or catheter 50, 1110 to aid in identifying where the end of the tube 50 is located. Timing for inflation can be initiated by having the tube 1100 contain a pH sensor that determines a location difference between the esophagus (pH 5-7) and the stomach 20 (pH 1-4) based on the different pH between the two anatomical sources, or can be derived or verified from the expected pressure in a contained (i.e., esophagus) versus a less-constrained space (i.e., stomach 20). The catheter 50, 1110 can also contain nitinol that has a tunable transmission to the body temperature, considering the timing for swallowing. The catheter 50, 1110 can also be connected to a series of encapsulated or compacted balloons 10 on a single catheter 50, 1110, each of which can be inflated and released separately. The number of balloons 10 released can be tune-able to the patient's needs and desired weight loss.

The catheter 50, 1110 may be coated to enhance swallowability or is impregnated or treated with a flavored version and/or one or more local anesthetics or analgesics to ease swallowing. Such anesthetics may include anesthetics in the amino amide group, such as articaine, lidocaine and trimecaine, and anesthetics in the amino ester group, such as benzocaine, procaine and tetracaine. Such analgesics may include chloraseptic.

Figure 34A:
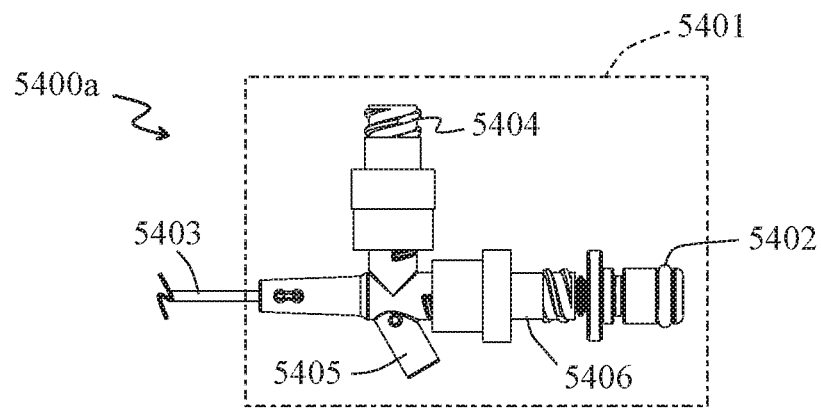
FIG. 34A is a side view of an exemplary catheter connection assembly 5400*a* for use with the dispenser 5200 of FIG. 29.
Figure 34B:
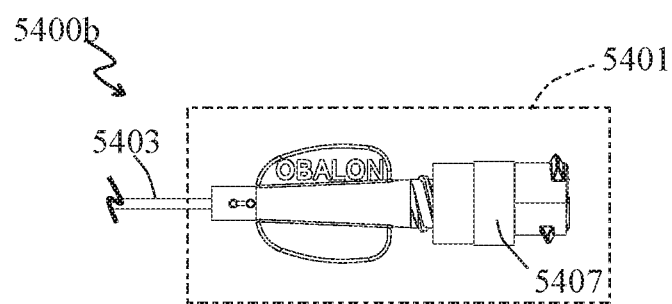
FIG. 34B is a side view of another exemplary catheter connection assembly 5400*b* for use with the dispenser 5200 of FIG. 29.

In another embodiment, a catheter 5400a or 5400b and tubing 5403 ("inflation assembly") are provided for inflating the balloon 10 after ingestion or placement in the stomach 20 (see FIGS. 34A and 34B). As shown in FIG. 34A, the catheter 5400a may comprise a two-way luer activated valve 5404 coupled to the dispenser connection assembly 5401 to allow for automatic pressure normalization between the intragastric device and pressure relative to the catheter 5400. Such a configuration makes the catheter 5400 safer for use on patients by automating the valve system as opposed to a manual configuration, and provides a "plug-n-play" functionality. Further illustrated in FIG. 34A, the dispenser connection assembly 5401 may also comprise an O-ring seal 5402 at the disconnect valve 5208 connection point. The O-ring 5402 can provide a seal to prevent pressure escape at the connection point, and may alternatively be constructed of any adhesive or molding sufficient to prevent release of pressure. The connection assembly 5401 may also comprise a one-way valve 5406 for back-flow prevention. For example, the valve 5406 may prevent backflow of ejection fluid. The valve 5406 may allow an operator to release the pressurized contents from the canister 410 into the intragastric device, but prevent the device from re-pressurizing the canister 410 or dispenser after emptying. It may further allow for the catheter 5400 to be removed from the dispenser and attached to another dispenser or other compatible device without releasing pressure from the intragastric device. The connection assembly 5401 may further comprise a sealed navigation port 5405 to allow the operator to navigate and control the catheter tube in areas that prevent the operator from directly handling it.

Additional description of catheters 50, 1110 for use with the intragastric balloon system 30, 1915, of FIG. 2 can be found in U.S. Pat. No. 8,647,358, issued Feb. 11, 2014, or U.S. Patent Publication No. 2013/0226219, published Aug. 29, 2013, each of which is incorporated herein in its entirety.

Inflation Fluid Container

The inflation fluid container or canister 1602 or 2003 is employed to control the amount or volume of fluid placed inside of the balloon. This can be in the form of a canister of, e.g., PVC, stainless steel, or other suitable material. The container can also be in syringe form. The materials employed are able to contain a fluid (e.g., a liquid, a gas, or a vapor), preferably in gas form, e.g., compressed or non-compressed $N_2$, $O_2$, Ar, $CO_2$, Ne, $CH_4$, He, Kr, $H_2$, and Xe, or mixture(s) thereof, or compressed or non-compressed atmospheric air (a mixture of $N_2$, $O_2$, Ar, $CO_2$, Ne, $CH_4$, He, Kr, $H_2$, and Xe), or inert gases including but are not limited to $SF_6$, $C_2F_6$, $C_3F_8$, $C_4F_{10}$, $C_4F_8$, $C_4F_8$, $C_3F_6$, $CF_4$, and $CClF_2$—$CF_3$, or combinations of one or more gases, e.g., a mixture of $N_2$ and $SF_6$. In selected embodiments, the following gases can be employed as inflation fluids, alone or in combination with other gases: hexafluoroethane, sulfur hexafluoride, perfluoropropane, perfluorobutane, perfluoropentane, perfluorohexane, perfluoroheptane, octafluorocyclobutane, perfluorocyclobutane, hexafluoropropylene, tetrafluoromethane, monochloropentafluoroethane, 1,2-dichlorotetrafluoroethane, Trichlorotrifluoroethane, trifluoroethane, chlorotrifluoroethylene, bromotrifluoromethane, monochlorotrifluoromethane, nitrogen, argon, air, xenon, and octafluoropropane.

The balloon composite wall materials and respective diffusion gradients and gas permeability characteristics are used to select a fluid for inflation of the intragastric balloon, so as to provide a desired volume profile over time for the inflated balloon. The inflation fluid container materials are selected to ensure no or minimal diffusion or leakage of the fluid before it is connected to the connector or valve of the inflation catheter. The inflation fluid container system includes a connector to the catheter and a pressure gauge. The inflation fluid container can be fabricated from any suitable material, e.g., stainless steel. It can also contain a smart chip that notifies the healthcare professional of whether inflation is successful or if the balloon 10 should be detached due to an error in the system.

In some embodiments, the inflation fluid container is in the form of a canister or container (flexible or stiff-bodied), squeezable bag, compliant balloon-like tube or the like. As with other embodiments described above, the canister or container has walls formed of stainless steel, pure aluminum, aluminum alloy, brass, or another suitable barrier material. The walls surround and define an inner reservoir or cavity. The canister may include an actuator which enables a delivery system to be activated to provide the gas, a valve cup configured to retain valve components in an arrangement, a spring, a stem connecting the actuator and the spring, a stem gasket that seals the opening around the valve stem, a tube or straw which extends from the valve to the bottom of the can, allowing the gas under pressure to flow out of the canister, and a housing which holds the spring and connects the tube or straw to the valve assembly. An aperture is typically disposed within one of the walls, providing an opening into the inner reservoir. Referring to GIS. 11A-11B, the canister includes a cap configured to seal the aperture to prevent fluid from escaping the inner reservoir during storage. When the cap is removed, a straw is visible. A portion of the straw protrudes externally from the canister; the remainder of the straw extends through the aperture and into the inner reservoir. The straw may be formed of polypropylene, polyethylene, nylon, or other suitable polymeric material. The canister of some embodiments is configured to release an inflation fluid from the inner reservoir via the straw when a low-pressure gradient fluid path is opened toward the balloon.

In some embodiments, it is desirable to inflate the intragastric balloon 10 using an inflation fluid container having a known internal pressure or quantity of gas. For example, in some embodiments, it is desirable to begin with an inflation fluid container configured to have a volume of, e.g., 50 $cm^3$ or less to 400 $cm^3$ or more, or from 100 $cm^3$ to 200 cm³ or 300 cm³, or from 125 cm³ to 175 cm³, or approximately 150 cm³. In other embodiments, other volumes of gas may be selected. In some embodiments, the inflation fluid container is filled at the site of the procedure, for example, by connecting the inflation fluid container to a tank of compressed gas prior to the procedure and filling the inflation fluid container until a desired volume or pressure is reached. The pressure can be monitored using a pressure gauge. In other embodiments, the inflation fluid container comes prefilled with the desired amount of fluid. In such embodiments, a location's altitude (and resultant atmospheric pressure) should be taken into account in order to provide an inflation fluid container having the desired volume of gas. Inflation fluid containers may be designed with different sizes, colors, or other distinctive marking indicating the altitude range for which each is tailored.

To maintain "swallowability" of the balloon 10 and to ensure comfort of the patient during the procedure, it is preferred to minimize the amount of time the catheter is placed in the mouth/esophagus. Timing of inflation can be selected so as to minimize time in place. The outer container-catheter assembly, once swallowed, takes approximately 3 to 120 seconds to reach the stomach. Once in the stomach, the inflation fluid container can be attached to a valve or port of the catheter system. Inflation timing can be controlled by selecting the length of catheter, diameter of the catheter tube, the starting temperature, and the starting pressure. Using the Ideal Gas Law for nitrogen and Boyle's Law ($P_1V_1=P_2V_2$) the amount of starting volume/pressure can be derived, where starting pressure takes into account the final target pressure at body temperature. It is desired to have an inflation time after swallow of less than 5 minutes, and preferably 2-3 minutes, before balloon 10 detachment and catheter withdrawal. The inputs use to derive inflation of the balloon 10 (preferably in less than 3 minutes) include inflation container volume, type of inflation fluid (preferably a compressed gas or compressed gas mixture), starting pressure, catheter length and diameter, and desired end volume and pressure of the balloon. Thus, due to differences in diameter, a smaller 1 French or 2 French diameter catheter system requires a lower starting pressure to achieve the same target balloon 10 volume and pressure in the same time frame as a larger diameter catheter (e.g., 4- or 5-French), assuming use of the same compressed gas formulation. In general, it is understood that starting with a lower pressure with the same flow rate/volume can increase the inflation time.

The inflation source container can provide feedback to the end user based on a pressure decay system. Where there is an expected starting pressure and expected ending pressure to indicate whether the balloon 10 is inflated properly, there is no need for endoscopic visualization. Each scenario of expected pressure outputs depicted in FIG. 12 can have its own tolerances around it to reduce possibilities of false positives, and the inflation fluid container can provide feedback based on these tolerances as to the status of balloon 10 inflation and detachment. The inflation container contains additional low volume bolus of pressure that is released to determine device location and then is followed by a second, larger bolus intended to inflate the balloon. The gas release could be done in 1, 2, 3 or a plurality of boluses based on the events intended to be detected. This is derived based on the Ideal Gas Law, where there is an expected end pressure based on the fixed volume of the balloon. If the pressure remains high and doesn't decay as expected, this can indicate a failure in the system (e.g., the balloon container 40 did not dissolve, the balloon 10 is expanding in the esophagus because there is, e.g., a kink in the tube or other failure in the catheter system). For example, for a successful decay using nitrogen only as the inflation fluid, the starting pressure is 22-30 PSI to inflate a balloon 10 to 250 cm³ and 1-2.5 psi (0.120 kg/cm²) for a nylon-based material. To indicate successful balloon 10 inflation, a math chip can be added to the inflation source container that provides at least one of a visual, audible, or tactile notification, or otherwise transmits a notification to a healthcare professional or administrator of whether inflation is successful or if there is an error in the system based on the pressure curve and a set of predetermined pressure tolerances and expected timing of inflation.

Figure 13:
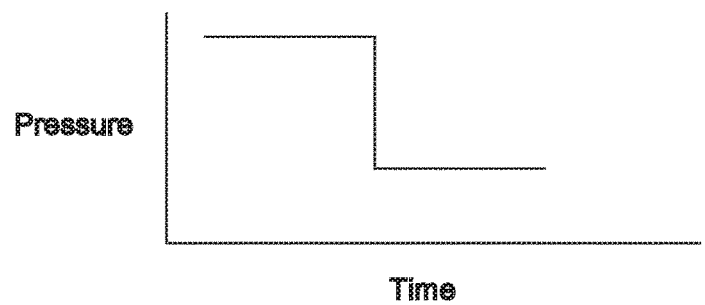
FIG. 13 depicts the expected decay curve for pressure sources using a spring mechanism or a balloon-within-balloon mechanism.
Figure 14A:
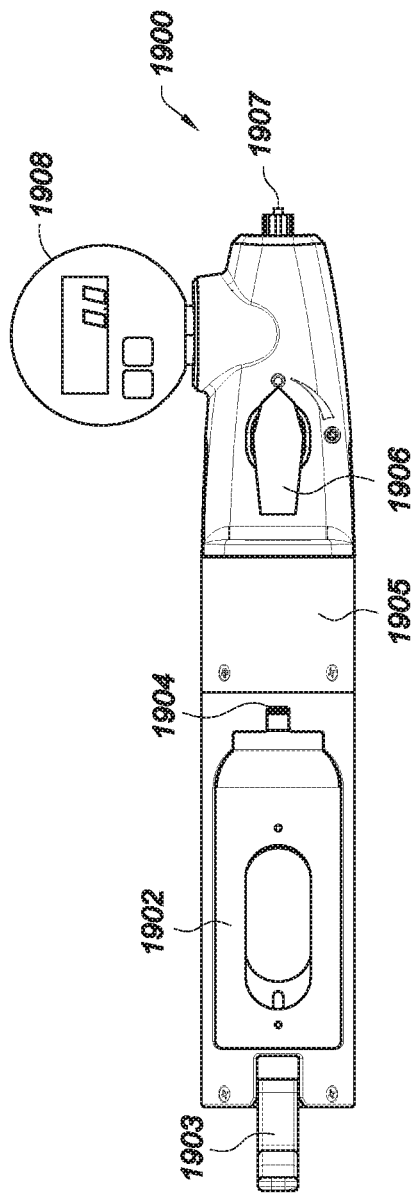
FIGS. 14A-14B depict an inflation fluid dispenser 1900 in isolation (FIG. 14A) and in connection with an inflation fluid container or canister 1602 (FIG. 14B). The inflation fluid dispenser ('dispenser') a securement latch 1901, a receiving space 1902 fitted to receive an inflation fluid container 1602, a spring 1904, a housing 1905 configured to couple to a canister, a lever 1906 for actuating a valve inflation fluid flow within the dispenser 1900, a port 1907, and a pressure gauge 1908.
Figure 14B:
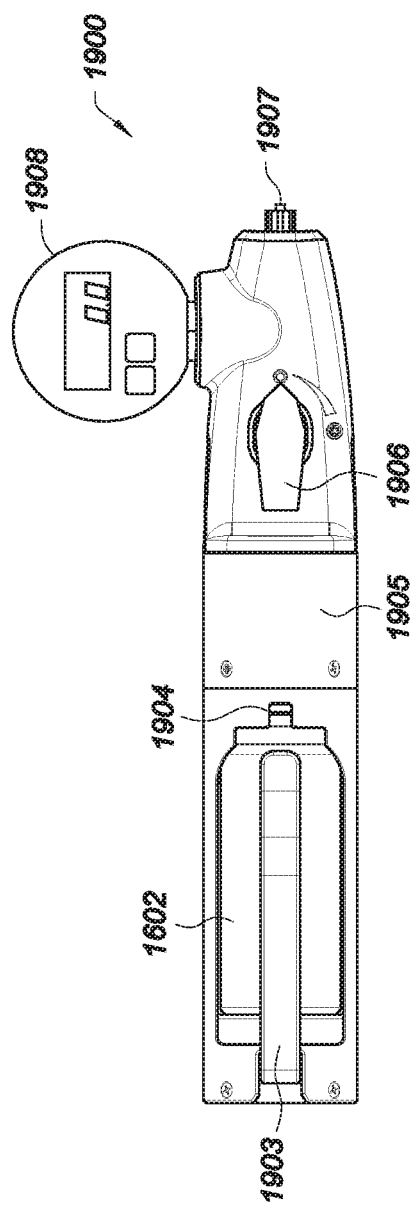

Alternatively, the balloon 10 can be filled based on a starting pressure by using a spring mechanism, a balloon-within-balloon mechanism, or other pressure source. These mechanisms can potentially result in more predictable/consistent pressure decay curves, and again can have accompanying, predetermined tolerances for feedback back to the end user. FIG. 13 depicts the expected decay curve for these methods of pressure sources, and again would have accompanying, predetermined tolerances for feedback back to the end user.

Inflation Fluid Dispeners

Figure 11A:
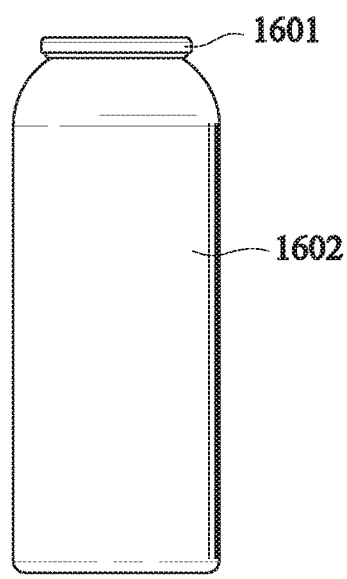
FIGS. 11A and 11B depict a disposable inflation fluid container 1602 with a cap 1601 and without a cap with a portion of a tube 1603 that extends to the bottom of the can exposed (FIG. 11A and FIG. 11B, respectively).
Figure 11B:
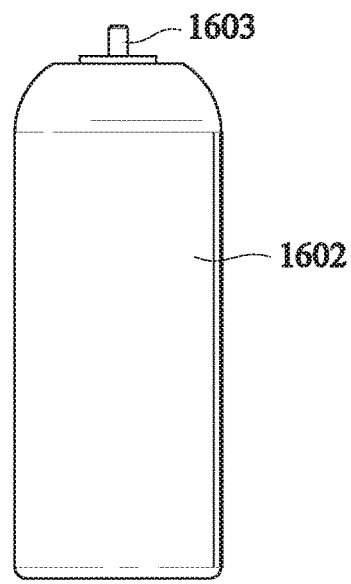
Figure 12:
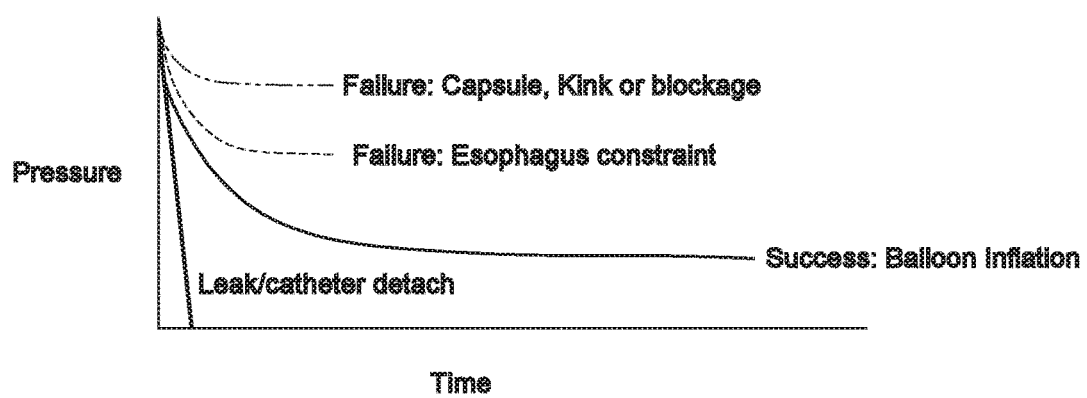
FIG. 12 is a graph depicting pressure as a function of time (pressure decay), obtained from feedback from an inflation source container.

FIGS. 14A-14C and 15 illustrate an exemplary embodiment of an inflation system, including an inflation fluid container 1602, an inflation fluid dispenser 1900 and an optional connector assembly 1911. In some embodiments, a canister, such as the canister of FIGS. 11A and 11B, is coupled to an inflation fluid dispenser 1900 in order to deliver an inflation fluid to the intragastric balloon 10 or other inflatable intragastric device. The inflation fluid dispenser 1900 includes a housing 1905 configured to couple to the canister 1602. Some embodiments have a securement latch 1903, a receiving space fitted to receive a canister 1602, a threaded engagement feature, and/or other features configured to securely couple the housing to the aerosol canister 1602.

The housing 1905 may also include a spring 1904 positioned to contact the straw 1603 of the aerosol canister 1602 when the aerosol canister 1602 is in its secured position within the housing 1905. In such embodiments, as the canister 1602 is brought into the secured position, the spring 1904 applies a force onto the straw 1603 in the direction of the canister 1602, causing a preliminary quantity of inflation fluid to be released from the canister 1602. In some embodiments, the release of a preliminary quantity of inflation fluid is designed to lower the inflation fluid within the aerosol canister 1602 to a desired starting volume or pressure. In some embodiments, the material, size, and strength of the spring 1904 are selected such that the amount of force exerted by the spring 1904, and the resultant preliminary quantity of inflation fluid released, are predetermined. The material, size, and strength of the spring 1904 can be selected according to the elevation and average atmospheric pressure of the location in which the inflation fluid dispenser will be used. In this manner, the inflation fluid dispenser can be calibrated for use in particular regions or elevation ranges, and a canister 1602 of a standard size and fill volume can be used regardless of location.

Figure 15:
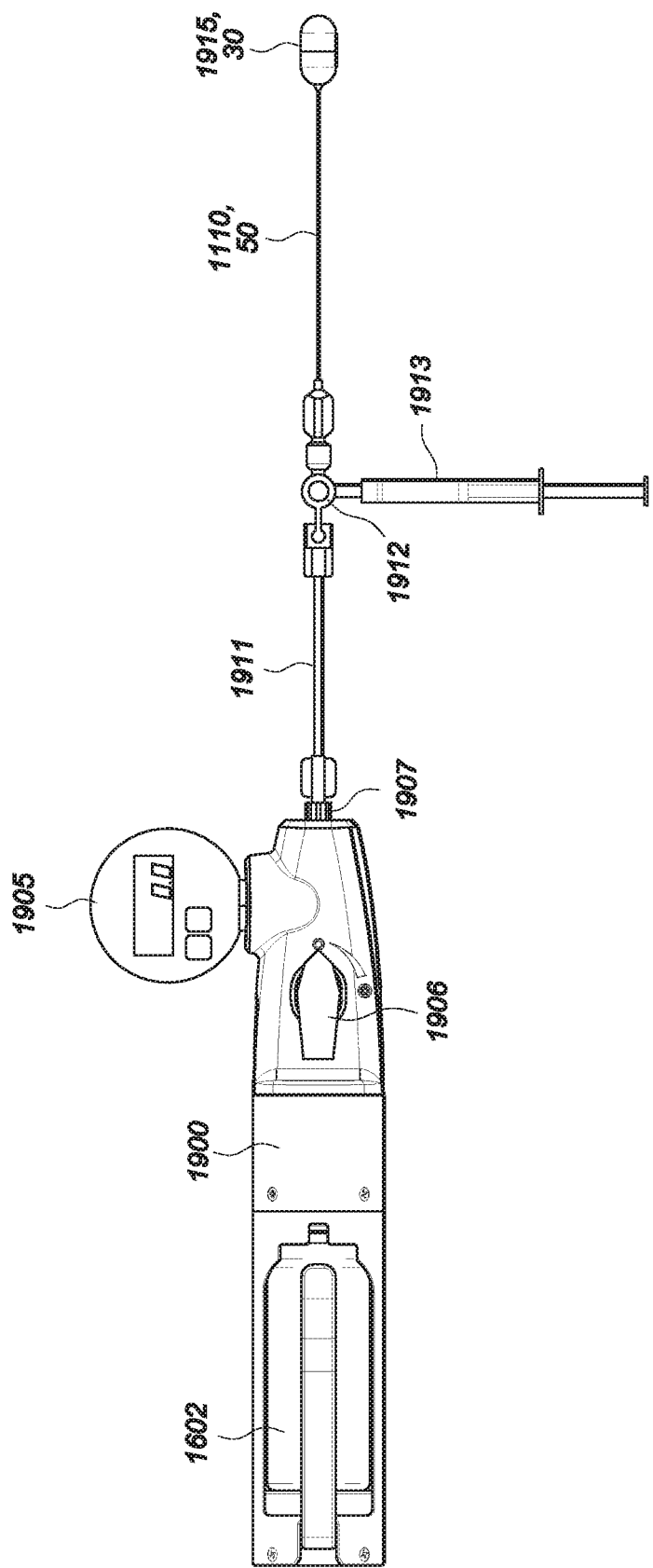
FIG. 15 depicts an inflation system for inflating a gastric balloon including an inflation fluid container 1602, an inflation fluid dispenser 1900, an extension tube 1911, a stopcock 1912 ('3-way valve'), a catheter 1110, 50 similar to those described with respect to FIGS. 2 and 9A-9C, an ejection syringe 1913, and a capsule encasing a balloon 1915, 30 similar to that described with respect to FIG. 2.
Figure 16:
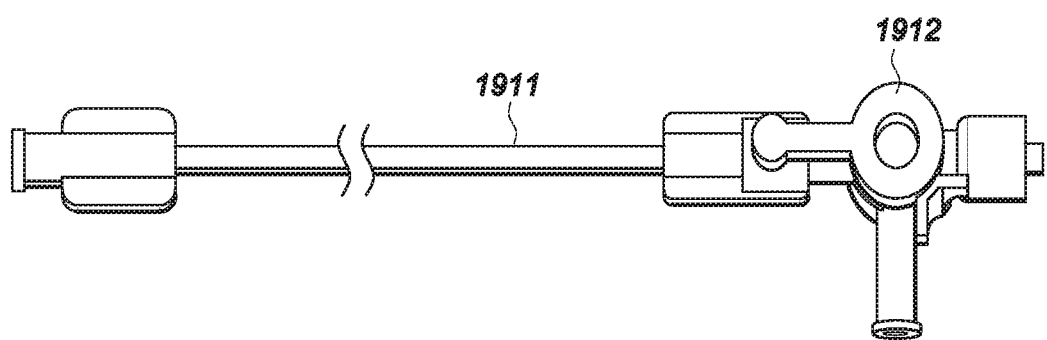
FIG. 16 depicts an extension tube 1911 and stopcock 1912 with a 3-way valve for use in conjunction with the Obalon Gastric Balloon Assembly of FIG. 17.
Figure 17:
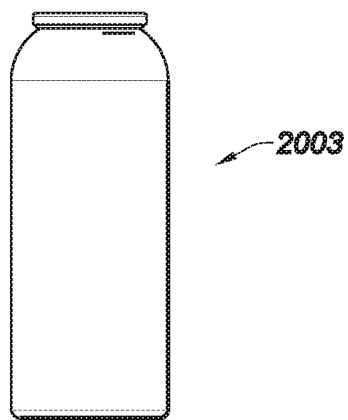
FIG. 17 depicts a disposable Procedure Canister ('can' or 'canister') 2003 for use with the Nitrogen Fill System ('dispenser') 2000 of FIG. 20 for use in conjunction with the Obalon Gastric Balloon Assembly 30 of FIG. 2.
Figure 18:
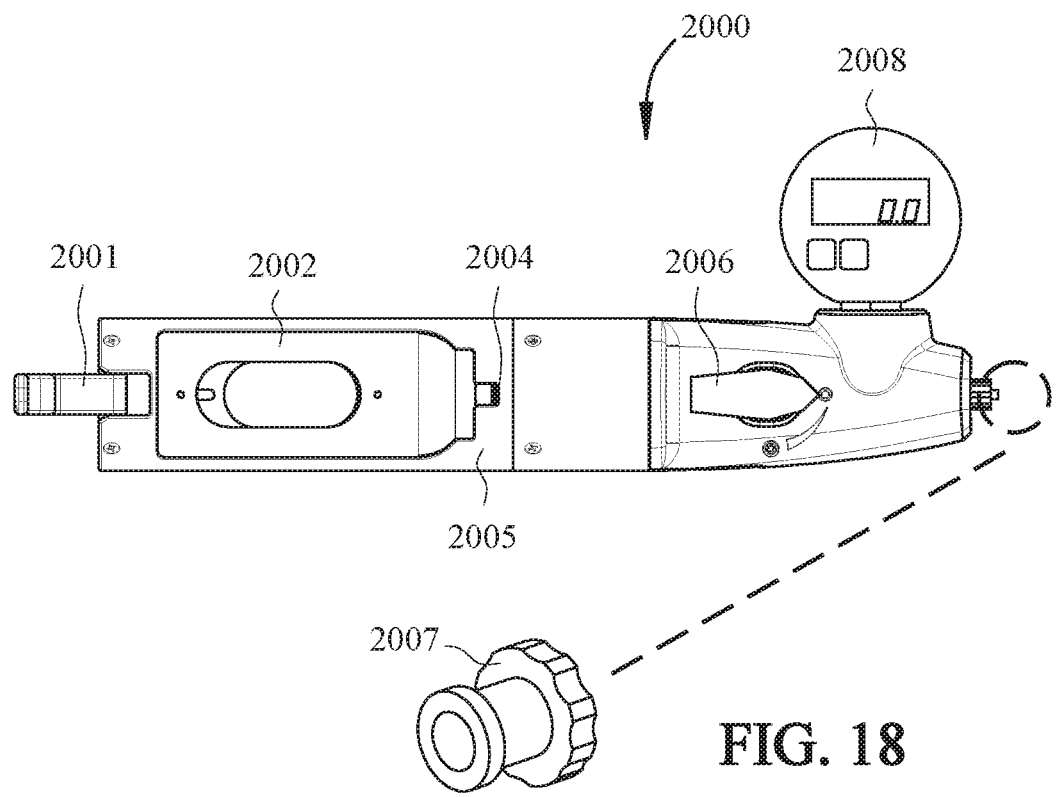
FIG. 18 depicts a Nitrogen Fill System 2000 (or "dispenser," for use in conjunction with the Obalon Gastric Balloon Assembly 30 of FIG. 2) with a securement latch 2001, a receiving space 2002 fitted to receive the Procedure Canister 2003 of FIG. 19, a spring 2004, a housing 2005 configured to couple to a canister 2003, a valve 2006, a port 2007 with a luer lock plug 2007 configured to cover the end of the gauge of the Nitrogen Fill System 2000 and the valve 2006 in the 'open' position, and a pressure gauge 2008, wherein the valve 2006 in the 'open' position.
Figure 19:
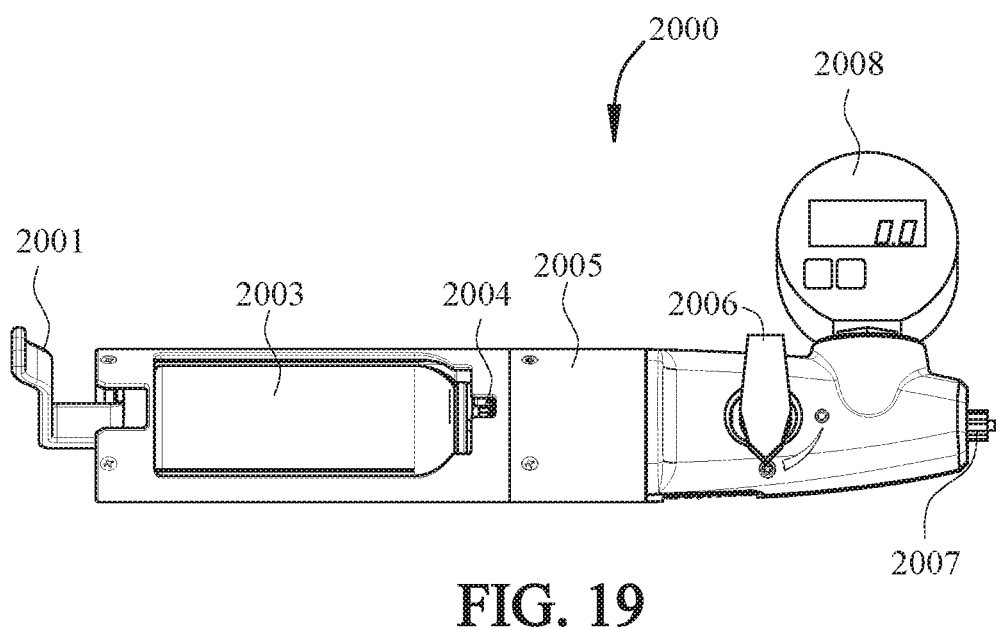
FIG. 19 depicts the Nitrogen Fill System 2000 with lever 2001 in the 'open' position and valve 3600 in the 'closed' position in advance of receiving the disposable Procedure Canister 2003.
Figure 20:
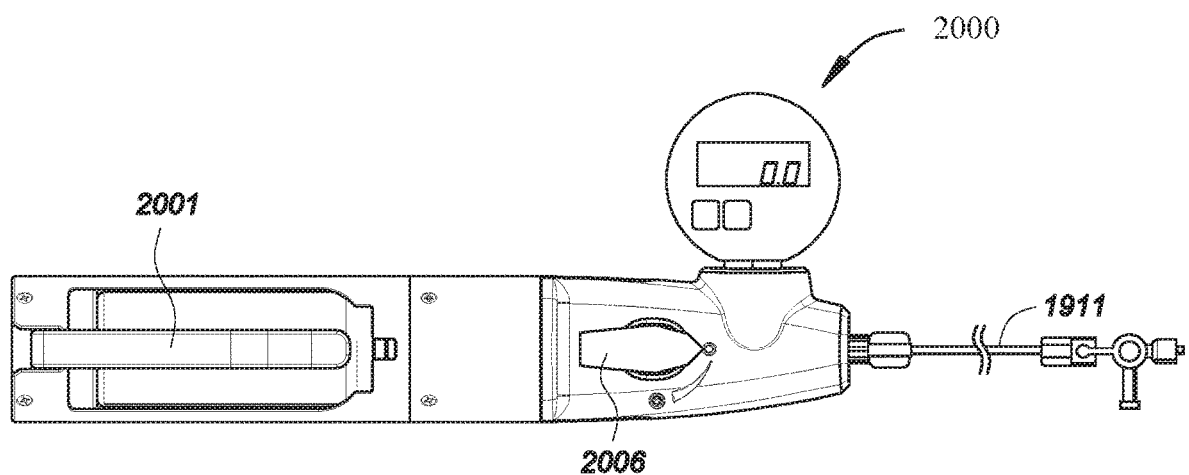
FIG. 20 depicts the Nitrogen Fill System 2000 of FIG. 18 with lever 2001 in the 'closed' position and valve 2006 in the 'open' position after receiving the disposable Procedure Canister 2003, and the Extension Tube 1911 attached to the port 2007.
Figure 21:
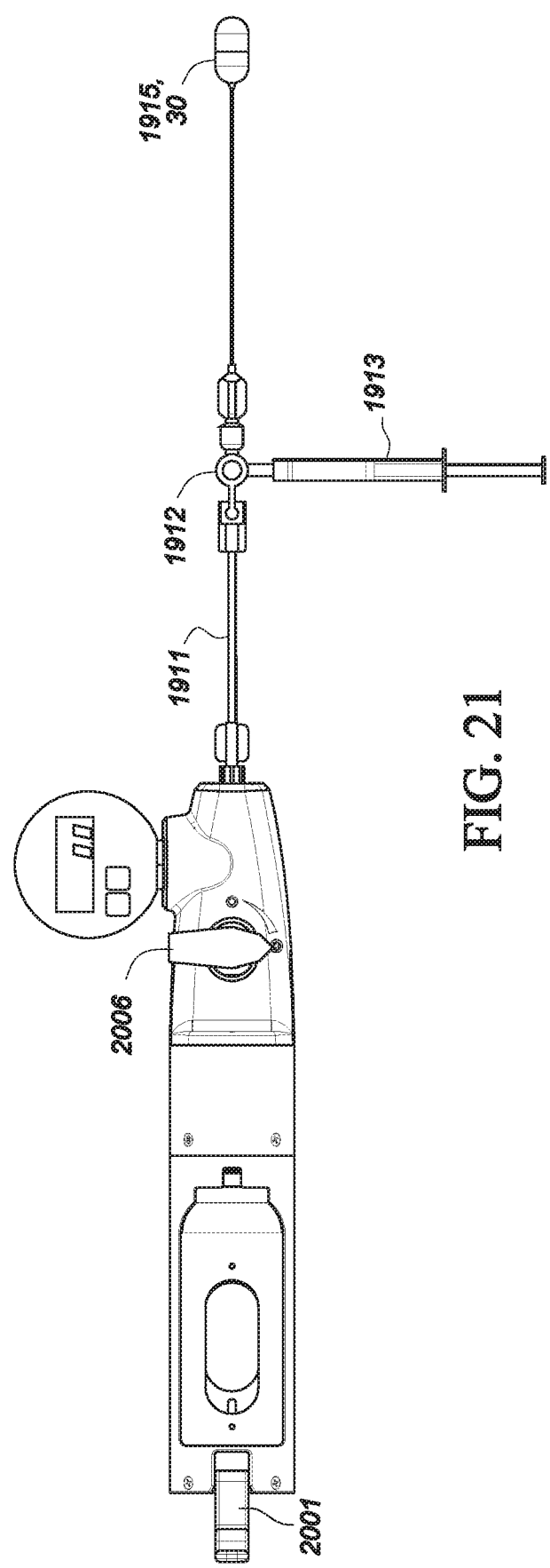
FIG. 21 depicts the Nitrogen Fill System 2000 with the valve 2006 in the 'closed' position, the Balloon Ejection Syringe 1913 and Obalon Gastric Balloon Assembly 1915, 30 attached to the Extension Tube 1911, and the 3-way valve 1912 (in the 'closed' position) attached to the catheter 1110, 50.
Figure 22:
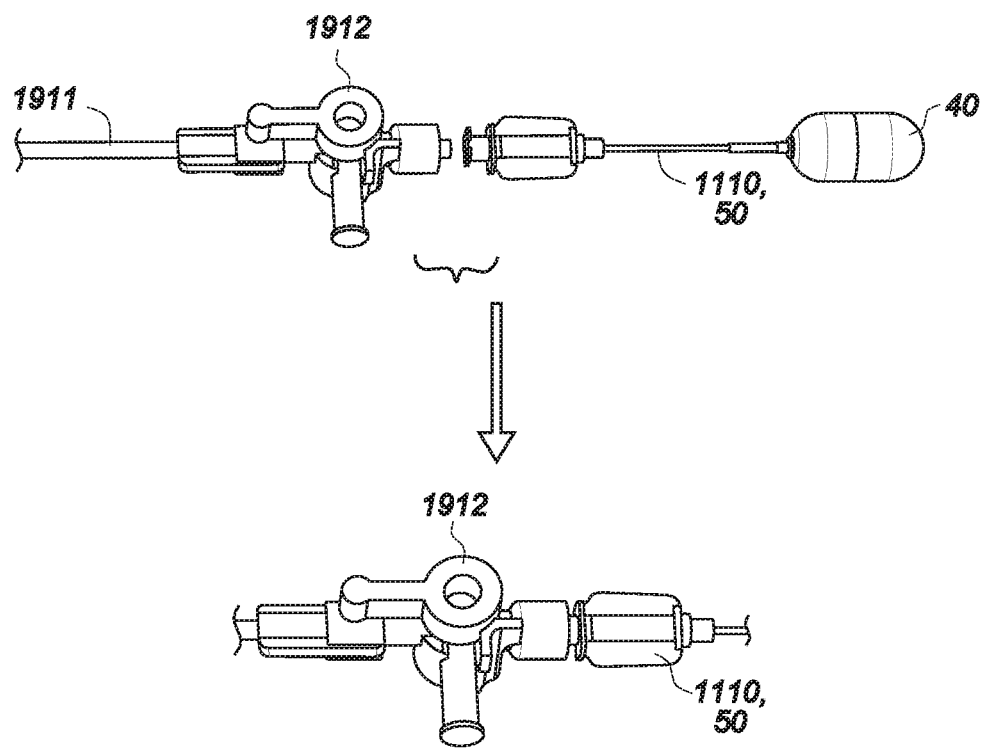
FIG. 22 depicts connection of the catheter 1110, 50 to the extension tube Extension Tube 1911 so as to attach the balloon (not shown) contained in the capsule 1915, 40 and with the 3-way valve in the 'closed' position.
Figure 23:
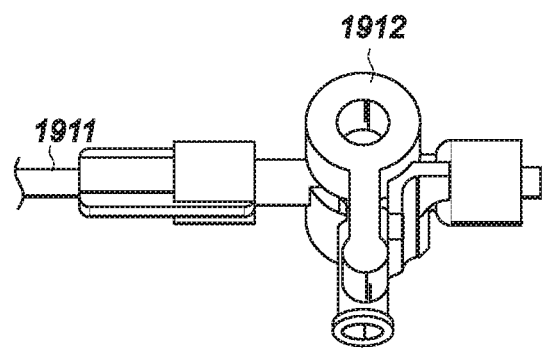
FIG. 23 depicts detail of the stopcock of the Extension Tube 1911 with 3-way valve 1912 in the 'open' position.
Figure 24:
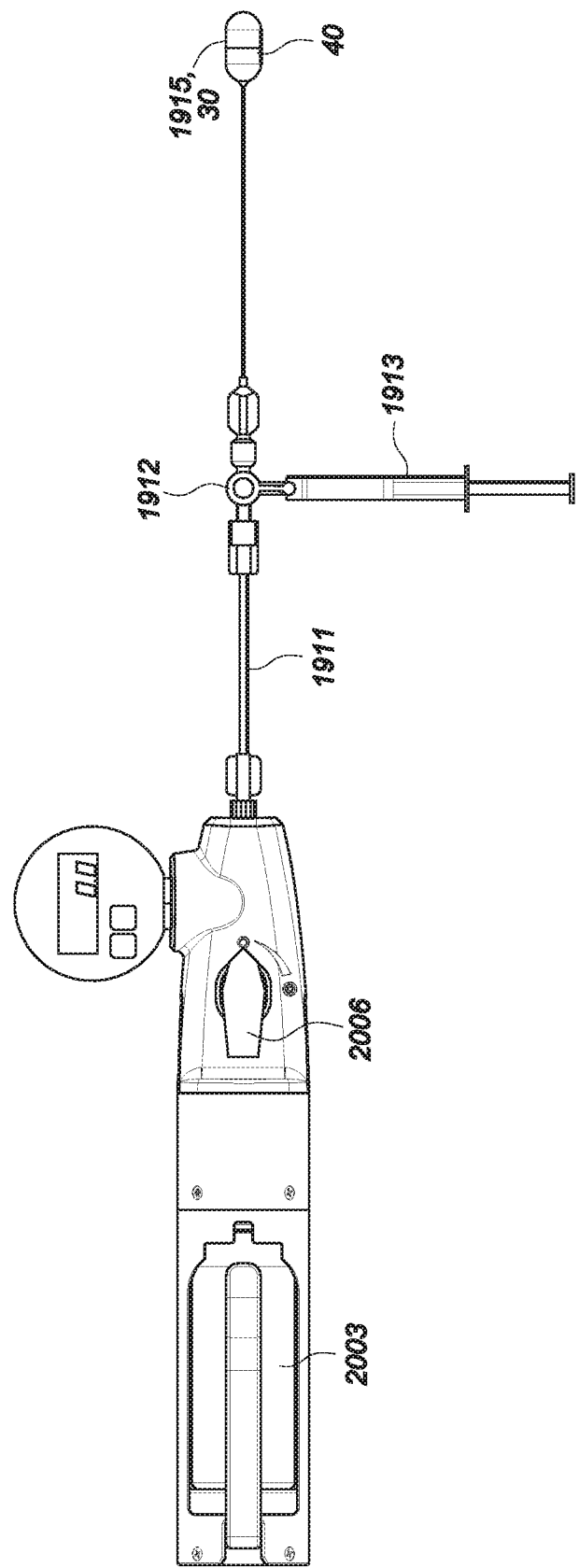
FIG. 24 depicts the Nitrogen Fill System with the valve 2006 in the 'open' position and the Balloon Ejection Syringe 1913 and Obalon Gastric Balloon Assembly 1915, 30 attached to the Extension Tube 1911 via the 3-way valve 1912, with the 3-way valve 1912 in the 'open' position, such that inflation fluid can flow from the canister 2003 to the balloon within the capsule 40.

The housing 1905 may also have an inner wall defining a channel (e.g., similar to channel 5203 of FIG. 29), which extends at least partially through the housing 1905. In such embodiments, a proximal inlet of the channel is positioned around the straw of the canister when the canister is securely coupled to the housing 1905. The spring 1904, if present, may be disposed within the proximal inlet. A distal outlet 1907 of the channel is positioned at a distal end of the inflation fluid dispenser 1900 and is configured as a port 1907 to which a catheter 50, 1110 or other flexible tubing can be connected. In various embodiments, a valve (e.g., mechanically coupled to lever 1906) is disposed in the channel between the proximal inlet 1904 and the distal outlet 1907 and is configured to transition between a 'closed' position (e.g., see lever 2006 in FIG. 19) and an 'open' position (e.g., see lever 1906 in FIG. 14A). In the closed position, the valve blocks the flow of fluid between the proximal inlet 1904 and the distal outlet 1907. In the open position, the flow of fluid is not blocked. Accordingly, as shown in FIG. 15, in the open position, an inflation fluid can flow from an inner reservoir of the aerosol canister 1602, 2003, through the straw 1603 of the canister 1602, 2003 and the channel of the inflation fluid dispenser 1900, and out the distal outlet 1907 to a catheter 50, 1110, and then an intragastric device 30, 1915, and/or other component coupled to the port 1907.

In some embodiments, the inflation fluid dispenser 1900 includes a lever 1906 disposed on an outer surface of the housing 1905 and mechanically coupled to the valve. A medical professional can move the lever 1906 between a first and a second position to transition the valve between the open and closed positions. In other embodiments, the inflation fluid dispenser 1900 may include a button, key, toggle, or switch disposed on an outer surface of the housing 1905 and electrically coupled to the valve. When manipulated by a medical professional, the button, key, toggle, or switch may send an electrical signal to the valve to open or close. In still other embodiments, any suitable valve control mechanism configured for manipulation by a user may be present in the inflation fluid dispenser 1900.

In some embodiments, a pressure gauge 1908 is coupled to the housing 1905 and configured to detect the gauge pressure within the channel between the valve and the distal outlet 1907. In some such embodiments, the pressure gauge 1908 includes a digital display; in other embodiments, the pressure gauge 1908 has a card and mechanical dial indicator.

In some embodiments, the inflation fluid dispenser 1900 and canister 1602, 2003 (or other inflation fluid container) form part of a larger inflation system 2000 used to deliver the inflation fluid to the inflatable intragastric device 10. One example of an inflation system is provided in FIGS. 18-24. In some such embodiments, flexible tubing and a substantially encapsulated intragastric device are coupled to the inflation fluid dispenser 2000 and inflation fluid container 2003. The flexible tubing may include a catheter 50, 1110 a synthetic rubber extension tube 1911, or other bendable, elongated device having an inner lumen. In some embodiments, the flexible tubing includes both an extension tube 1911 and a catheter 50, 1110 connected via spokes of a stopcock 1912 having a three-way valve 1912 (e.g., see FIGS. 22-24. A syringe 1913 may be connected to a third spoke of the three-way valve 1912. Each of these components of the system is described in detail above.

In one method of delivering an inflatable intragastric device 10 into a patient's stomach 20 illustrated in FIGS. 18-24, the inflation fluid dispenser 2000 is first coupled to the inflation fluid container 2003. In some embodiments, this coupling is performed with the dispenser's valve in an open position. The inflation fluid dispenser 2000 may contain a barometric pressure compensation valve that accounts for temperature, altitude, starting pressure; where based on the current altitude settings adjusts for the final starting gas number of moles required to inflate a balloon 10 to its target pressure (constant, but can range from 1-5 psi). This compensation is done at coupling and may cause a preliminary amount of inflation fluid to be vented from the distal outlet 2007 of the channel when the inflation fluid container 2003 comes into contact with, and experiences a force from, a spring 2004 positioned in the proximal inlet of the channel based on differences in the environment of the manufacturing settings and the current environment the device 2000 is being utilized in (e.g., altitude). In some embodiments having a pressure gauge 2008, when the valve is open, the pressure of the inflation fluid container can be monitored. In some embodiments, it is desired for inflation fluid to be vented from the inflation fluid container 2003 until the pressure within the container 2003 reaches 250 kPa, 300 kPa, or any value there between. In other embodiments, the desired pressure within the inflation fluid container 2003 is between 257 and 297 kPa, inclusive of said values. Once the inflation fluid container 2003 is securely coupled to the dispenser 2000 and the desired pressure has been reached, the valve may be closed.

In some embodiments, the extension tube 1911, stopcock 1912, catheter 1110, 50, ejection syringe 1913, and the at least partially encapsulated intragastric device 1915, 30 are attached to each other, and a proximal end of the extension tube 1911 is attached to the port 2007 on the distal end of the dispenser 2000. With the three-way valve of the stopcock 1912 in a position which allows for fluid connection between the extension tube 1911 and the catheter, fluid will flow between the channel of the dispenser 2000 (downstream from the dispenser's valve), the extension tube 1911, the catheter 50, 1110, and the encapsulated intragastric device 30, 1915 until an equilibrium is reached. The reading of the pressure gauge 2008 should be generally reflective of the pressure within the intragastric device 10.

In some methods of delivering the inflatable intragastric device 10 into a patient's stomach 20, the patient swallows the substantially encapsulated intragastric device 30 in order to deliver it to the stomach 20. In various embodiments, the catheter 50, 1110 remains connected to the intragastric device 30 and extends from the stomach 20, through the esophagus, and at least into the patient's mouth. In some embodiments, the swallowing and positioning of the intragastric device 30 is monitored using a radiographic imaging method, such as, for example, fluoroscopy.

Once in the stomach 20, the capsule 40 surrounding the intragastric device 10 of various embodiments begins to dissolve. In some embodiments, the capsule 40 dissolves in less than ten minutes. In some embodiments, the capsule 40 dissolves within thirty seconds to four minutes. In some embodiments, the detected pressure will drop to below 10 kPa when the capsule dissolves. In some embodiments, the detected pressure will drop below 7 kPa upon dissolution. In various embodiments, the process of filling the inflatable intragastric device 10 can begin upon dissolution of the capsule 40. In order to fill the inflatable intragastric device 10 with an inflation fluid, the valve of the dispenser 2000 is transitioned to an open position. Inflation fluid will flow substantially from the relatively high-pressured inner reservoir of the inflation fluid container 2003 to the relatively low-pressured inner cavity of the inflatable intragastric device 10 until an equilibrium pressure is achieved in the system. In some embodiments, approximately 150 cm$^3$ of a gas in unconstrained atmosphere that is constrained to 28 psi or approximately 450 cc at atmospheric pressure. For example, $N_2$ will be transferred into the intragastric device 10. In some embodiments, the intragastric device 10 will achieve a final volume within the stomach 20 of approximately 250 cc. In other embodiments, the intragastric device 10 will achieve a final volume within the stomach 20 of 50 to 400 cc, and preferably 90 to 300 cc, or any individual value or range there between. The intragastric device 10 of some embodiments will achieve a final pressure of 5 kPa, 20 kPa, or any value there between. In a preferred embodiment, the final pressure within the intragastric device 10 is between 8.3 kPa and 17.2 kPa, and more preferably, the final pressure of the intragastric device 10 is 13.8 kPa. The intragastric device 10 of some embodiments reaches a desired final pressure in less than five minutes. In some embodiments, the final pressure is reached in approximately two minutes.

In some embodiments of the method, once the pressure of the system has stabilized and reached an equilibrium, the catheter can be separated from the intragastric device 10 and removed from the patient. In some embodiments, the syringe 1913 is used to separate the catheter 50, 1110 from the intragastric device 10. The three-way valve 1912 is moved into a position in which the syringe is in fluid connection with the catheter 50, 1110 and intragastric device 10. The syringe's plunger is pushed rapidly and expels a fluid from the syringe 1913 into the inner cavity of the balloon 10 at a force (e.g., hydraulic force) sufficient to dislodge the catheter 50, 1110 from the intragastric device 10.

Automated Inflation Systems

FIGS. 25-46 illustrate several embodiments of an automated inflation system for use with the Obalon Gastric Balloon Assembly 30. In some embodiments, an automated inflation system is employed to deliver inflation fluid to an inflatable gastric device similar to that illustrated in FIGS. 2 and 15. An automated inflation system can include a computing device, such as a computer, having a processing unit, such as a processor, microprocessor, or microchip configured to perform logical operations to cause one or more components of the inflation system to perform functions to facilitate the inflation of an intragastric balloon to a final target volume. The inflation fluid container or the inflation fluid dispenser can be configured to dispense an inflation fluid for delivery to an intragastric balloon. The computing device can further include a memory, which may be read only memory (ROM) and random-access memory (RAM). The memory can store one or more modules that store data values defining instructions to configure the processing unit to perform the logical operations of the inflation fluid system. In some embodiments, the computing device can include a user interface having a user input configured to allow a user to program one or more parameters of the inflation system. The user interface can further include a display configured to display data regarding the operation of the inflation system.

The computing device can further include a communications module for transmitting and/or receiving data from one or more components of the automated inflation system. The communications module can include a receiver, a transmitter, and or a transceiver. The communications module can be configured to communicate via any suitable wired or wireless communications medium. In some embodiments, the communications module can be configured to communicate with an external device via a medium capable of transmission through the body of a patient.

In some embodiments, the communications module of the computing device can be configured to transmit instructions to an inflation fluid container or inflation fluid dispenser. The memory of the computing device can store instructions that configure the processing unit to cause the inflation fluid container or the inflation fluid dispenser to dispense an initial volume of inflation fluid estimated to cause the intragastric balloon to inflate to a final target pressure of the intragastric balloon or an initial bolus target pressure. The initial bolus target pressure can be a pressure less than the desired final target pressure of the intragastric balloon. After an intragastric balloon receives an initial volume of inflation fluid causing the intragastric balloon to fill to an initial bolus target pressure less than the final target pressure of the intragastric balloon, the inflation system can be configured to provide one or more additional incremental volumes of inflation fluid to raise the pressure in the intragastric balloon to the final target pressure, as described further herein. In some embodiments, the initial bolus target pressure can be a pressure greater than the desired final target pressure of the intragastric balloon. After an intragastric balloon receives a volume of inflation fluid causing the intragastric balloon to fill to an initial bolus target pressure greater than the final target pressure of the intragastric balloon, the inflation system can be configured to cause the incremental release of one or more volumes of inflation fluid from the intragastric balloon in order to cause the pressure in the intragastric balloon to decrease to the final target pressure, as described further herein.

The inflation fluid container or inflation fluid dispenser can include a communications module configured to communicate with the computing device and/or one or more other components of the inflation system. The inflation fluid container or inflation fluid dispenser may further include a processing unit and/or memory storing data values defining instructions to configure the processing unit to perform the logical operations of the inflation fluid container or inflation fluid dispenser.

The inflation fluid system can further include one or more pressure sensors configured to provide data to the computing device. The pressure sensors can include a communications module for transmitting data to the computing device. The processing unit of the inflation fluid container can be configured to determine based on the data from the one or more pressure sensors, one or more additional volumes of inflation fluid to dispense in order to cause the intragastric balloon to inflate to a final target pressure. In some embodiments, the inflation system can include at least one pressure sensor configured to detect a pressure within the balloon. In some embodiments, the inflation system can include at least one pressure sensor configured to detect a pressure within the inflation fluid container or inflation fluid dispenser.

In some embodiments, the inflation fluid system can include a pressure regulator configured to reduce the pressure of the inflation fluid received from the inflation fluid container to a lower desired value at an output of the pressure regulator. Inflation fluid output from the pressure regulator can be direct to the intragastric balloon. Reduction of the pressure of the inflation fluid by the pressure regulator can allow the inflation fluid to enter the intragastric balloon at a safe pressure to reduce the risk of harm to patient. Further, reduction of pressure of the inflation fluid by the pressure regulator can allow for delivery of inflation fluid at a consistent pressure, which can improve the accuracy of the processing unit of the inflation fluid container or inflation fluid dispenser in determining additional volumes of inflation fluid to dispense in order to cause the intragastric balloon 10 to inflate to a final target pressure. In some embodiments, the pressure regulator can be configured to communicate with the computing device and/or one or more additional components of the inflation system. The pressure regulator may further include a processing unit and/or memory storing data values defining instructions to configure the processing unit to perform the logical operations of the pressure regulator. For example, in some embodiments, the pressure regulator can be configured to change the pressure of the inflation fluid output from the pressure regulator in response to data, such as pressure sensor data, received from the computing device and/or one or more additional components of the inflation system. In some embodiments, the pressure regulator can be configured to transmit data to the computing device for use in determining additional volumes of inflation fluid to dispense in order to cause the intragastric balloon to inflate to a final target pressure. The pressure regulator can be a diaphragm style pressure regulator, a piston style pressure regulator, or any other suitable pressure regulator.

The inflation fluid system can further include one or more valves configured to control the flow of the inflation fluid through the inflation system. In some embodiments, the inflation fluid system can include a valve positioned to control the flow of inflation fluid between the pressure regulator and the intragastric balloon. A pressure sensor can be positioned between the valve and the intragastric balloon such that, when the valve is closed, the reading of the pressure sensor is indicative of the pressure within the intragastric balloon. In some embodiments, a valve can be positioned between the intragastric balloon 10 and an outflow opening. A valve positioned between the intragastric balloon 10 and the outflow opening can be opened to control the flow of inflation fluid from the intragastric balloon 10 to the outflow opening to facilitate the reduction of pressure within the intragastric balloon. Each of the valves of the inflation system can be configured to communicate with the computing device and/or one or more additional components of the inflation system. Each valve can further include a processing unit and/or memory storing data values defining instructions to configure the processing unit to perform the logical operations of the pressure the valve. For example, each valve can be configured to open or close in response to instructions received from the computing device or one or more additional components of the inflation system. In some embodiments, each valve can transmit data to the computing device or one or more other components of the inflation system. For example, each valve can transmit data regarding the status of the valve as open or closed.

An automated inflation system can further include one or more sections of flexible tubing configured to facilitate the flow of the inflation fluid between various components of the inflation system.

Figure 25:
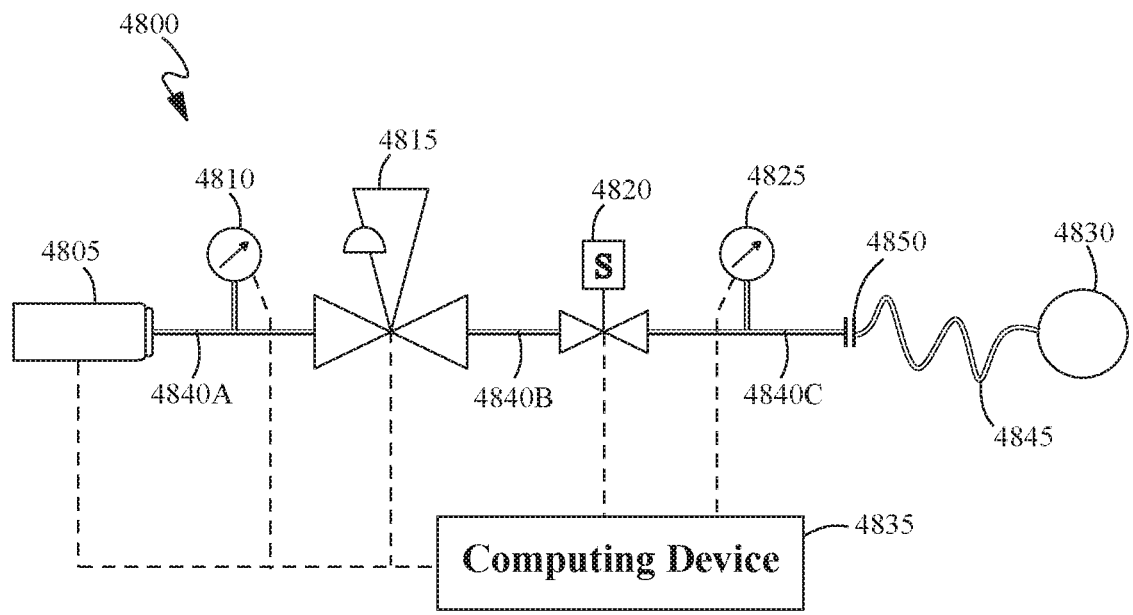
FIG. 25 is a schematic of an inflation system 4800 for inflating an intragastric balloon 10.

One example of an automated inflation system is provided in FIG. 25. FIG. 25 depicts an inflation system 4800 including an inflation fluid container 4805, a first pressure gauge 4810, a pressure regulator 4815, a valve 4820, a second pressure gauge 4825, an intragastric balloon 4830, and a computing device 4835. The inflation system 4800 can further including a plurality of sections of flexible tubing 4840A-C (or a rigid channel) to facilitate the flow of an inflation fluid from throughout the inflation fluid system 4800. The intragastric balloon 4830 can be configured to receive the inflation fluid via a catheter 4845 connected to the flexible tubing at a connector 4850.

The inflation fluid container 4805 can contain an inflation fluid for delivery to the intragastric balloon 4830. When full, the inflation fluid container 4805 can have a pressure of 60 psi or about 60 psi. In response to instructions from the computing device 4835, the inflation fluid container 4805 can be configured to dispense a bolus of inflation fluid into the flexible tubing 4840A. The pressure regulator 4815 can be positioned to receive the inflation fluid from the flexible tubing 4840A. The pressure regulator 4815 can be configured to reduce the pressure of the inflation fluid. In some embodiments, the pressure regulator 4815 reduces the pressure of the inflation fluid to 5 psi, about 5 psi, 4 psi, about 4 psi, 3 psi, about 3 psi, 2 psi, about 2 psi, 1 psi or about 1 psi. In some embodiments, the pressure regulator can receive instructions from the computing device 4835 to adjust the pressure of the inflation fluid output by the pressure regulator. The pressure regulator can be configured to output the inflation fluid into the flexible tubing 4840B. The valve 4820 can be positioned to receive inflation fluid from the flexible tubing 4840B. The valve 4820 can be opened to permit inflation fluid to flow through the valve or closed to prevent inflation fluid from flowing through the valve. In some embodiments, the valve 4820 can be configured to open or close in response to instructions received from the computing device 4835. In some embodiments, the valve 4820 can be a solenoid valve. Inflation fluid flowing through the valve 4820 can be output into the flexible tubing 4840C. Inflation fluid flowing through the flexible tubing 4840C can flow through the catheter 4845 and into the intragastric balloon 4830. In some embodiments, a final target pressure of the intragastric balloon 4830 is 2 psi or about 2 psi. In some embodiments, a final target pressure of the intragastric balloon 4830 is between 2 psi to 5 psi or between 2 psi to 8 psi. Inflating an intragastric balloon to a pressure above 8 psi may risk injury to a patient.

The pressure gauge 4810 can be positioned between the inflation fluid container 4805 and the pressure regulator 4815. The pressure gauge 4810 can allow the pressure in the inflation fluid container 4805 to be monitored. The pressure gauge 4810 can further be configured to transmit pressure data to the computing device 4835 for processing. The computing device 4835 can monitor the pressure data received from the pressure gauge 4810 in the event of failure of the inflation system 4800, for example, as described herein with respect to FIG. 12.

The pressure gauge 4825 can be positioned between the valve 4820 and the intragastric balloon 4830. When the valve 4820 is closed, the reading of the pressure gauge 4825 should be generally reflective of the pressure within the intragastric balloon 4830 after an equilibrium is reached. The pressure gauge 4825 can be configured to transmit pressure data to the computing device 4835 for processing.

Figure 27:
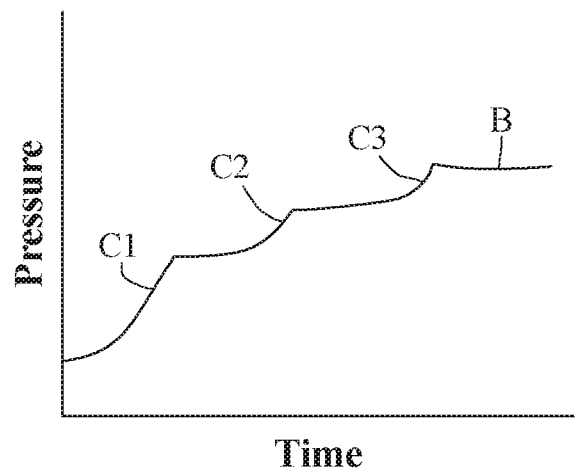
FIG. 27 depicts a graph illustrating the pressure in an intragastric balloon over time as the intragastric balloon is inflated in an exemplary operation of the inflation system 4800 of FIG. 25.

Referring now to FIG. 27, in one example of operating the inflation system 4800, the computing device 4835 can provide instructions to dispense an initial bolus volume C1 of inflation fluid from the inflation fluid container 4805 into the inflation fluid system 4800 (e.g., into tubing 4840A). The initial bolus C1 volume of the inflation fluid may be a volume estimated to produce a final target pressure B in the intragastric balloon 4830 or an initial bolus target pressure that is less than the final target pressure B. The valve 4820 can be in the open position prior to dispensing of the initial bolus C1 volume of inflation fluid from the inflation fluid container 4805 or may be opened after dispensing of the initial bolus C1 volume of inflation fluid from the inflation fluid container 4805 to allow the initial bolus C1 volume of the inflation fluid container to flow through the inflation fluid system 4800 and into the balloon 4830.

After a defined period of time sufficient to allow the initial bolus C1 volume of inflation fluid to flow into the intragastric balloon 4830, the computing device 4835 can be configured to provide instructions to the valve 4820 to close. The defined period of time can be determined by the computing device 4835. After the valve 4820 is closed, the computing device 4835 can be configured to determine an additional bolus (e.g., C2, C3) or volume of inflation fluid to be dispensed by the inflation fluid container 4805 when it is determined that the pressure in the intragastric balloon 4830 is lower than the final target pressure B based on data received from the pressure gauge 4825 after sufficient time is allowed for equilibrium to be achieved. As explained above, when the valve 4820 is closed and equilibrium is achieved (e.g., as indicated by a flat portion of the graph line of FIG. 27), the pressure measured by the pressure gauge 4825 is generally indicative of the pressure within the intragastric balloon 4830. In some embodiments, the computing system 4835 is configured to determine that equilibrium has been achieved after a determined period of time. In other embodiments, the computing system 4835 is configured to determine that equilibrium is achieved based on trends in the data received from the pressure gauge 4825.

After the computing device 4835 determines an additional volume or bolus (e.g., C2, C3) of inflation fluid to be dispensed from the inflation fluid container 4805, the computing device can provide instructions to the inflation fluid container 4805 to dispense the determined additional volume of inflation fluid. The computing device 4835 can further provide instructions to the valve 4820 to open to allow the determined additional volume (e.g., C2, C3) of the inflation fluid to flow into the balloon 4830. Measurement of the pressure within the intragastric balloon 4830, determination of an additional volume of inflation fluid to be dispensed by the inflation fluid dispenser 4800, and dispensing of additional volumes of inflation fluid can be repeated until a final target pressure of the intragastric balloon 4830 is achieved.

FIG. 27 depicts a graph showing an example of pressure measurements measured by the pressure gauge 4825 during inflation of an intragastric balloon inflated by dispensing incremental volumes of inflation fluid, wherein the target final balloon pressure B is approached incrementally by sequential boluses (e.g., C1, C2, C3) of inflation fluid into the balloon.

The computing device 4835 can further be configured to determine a status of the inflation system 4800 based on data from the first pressure gauge 4810 and the second pressure gauge 4825. For example, if the pressure measured at the first pressure gauge 4810 and the pressure measured at the second pressure gauge 4825 are each above certain values, a determination can be made that the intragastric balloon 4830 may be constrained, such as but not limited to in the esophagus or in a constrained space associated with the gastric system. If the pressure measured at the first pressure gauge 4810 and the pressure measured at the second pressure gauge 4825 are both below certain values, a determination can be made that there may be a leak in the inflation system 4800. Further, a certain range of pressures measured at each of the first pressure gauge 4810 and the second pressure gauge 4825 can be indicative of a successful inflation of the balloon 4830.

Although a separate computing device 4835 is described, one of skill in the art would recognize that the computing device may be part of one of the other components of the inflation system 4800, such as for example, the inflation container 4805 or a dispenser. In some embodiments, the functions described with respect to the computing device 4835 may instead be performed multiple separate components of the inflation system 4800. In some embodiments, one or more functions described with respect to the computing device 4835 can be performed at one or more processing units in connection with one or more of the inflation fluid container 4805, the first pressure gauge 4810, the pressure regulator 4815, the valve 4820, and the second pressure gauge 4825.

Figure 26:
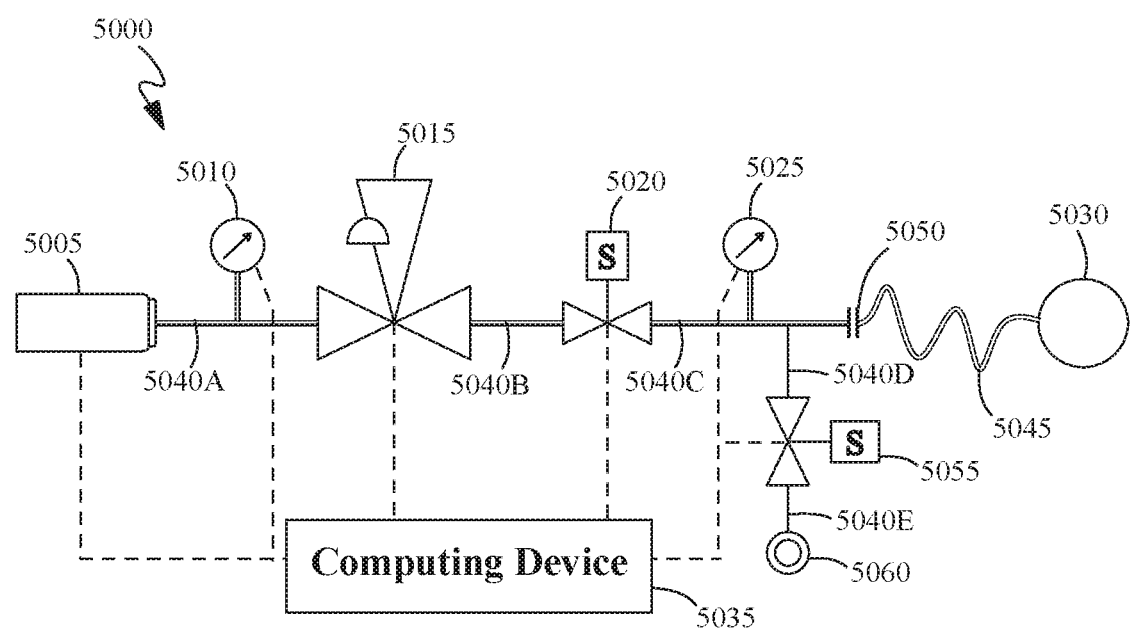
FIG. 26 is a schematic of another inflation system 5000 for inflating an intragastric balloon 10.

Another example of an automated inflation system is provided in FIG. 26, which depicts an inflation system 5000 including an inflation fluid container 5005, a first pressure gauge 5010, a pressure regulator 5015, a first valve 5020, a second pressure gauge 5025, a second valve 5055, an outflow opening 5060 or vent, and an intragastric balloon 5030, and a computing device 5035. The inflation system 5000 can further including one or more sections of flexible tubing 5040A-E (or a rigid channel) to facilitate the flow of an inflation fluid from throughout the inflation fluid system 5000. The intragastric balloon 5030 can be configured to receive the inflation fluid via a catheter 5045 connected to the flexible tubing at a connector 5050, such as is described elsewhere herein.

The inflation fluid container 5005 can contain an inflation fluid for delivery to the intragastric balloon 5030. When full, the inflation fluid container 5005 can have a pressure of 60 psi or about 60 psi. In response to instructions from the computing device 5035, the system 5000 can be configured to dispense an initial bolus of inflation fluid from the inflation fluid container 5005 into the flexible tubing 5040A. The pressure regulator 5015 can be positioned to receive the inflation fluid from the flexible tubing 5040A. The pressure regulator 5015 can be configured to reduce the pressure of the inflation fluid. In some embodiments, the pressure regulator 5015 reduces the pressure of the inflation fluid to 5 psi, about 5 psi, 4 psi, about 4 psi, 3 psi, about 3 psi, 2 psi, about 2 psi, 1 psi or about 1 psi. In some embodiments, the pressure regulator can receive instructions from the computing device 5035 to adjust the pressure of the inflation fluid output by the pressure regulator. The pressure regulator can be configured to output the inflation fluid into the flexible tubing 5040B. The first valve 5020 can be positioned to receive inflation fluid from the flexible tubing 5040B. The first valve 5020 can be opened to permit inflation fluid to flow through the valve or closed to prevent inflation fluid from flowing through the valve, respectively. In some embodiments, the first valve 5020 can be configured to open or close in response to instructions received from the computing device 5035. In some embodiments, the first valve 5020 can be a solenoid valve. Inflation fluid flowing through the first valve 5020 can be output into the flexible tubing 5040C. Inflation fluid flowing through the flexible tubing 5040C can flow through the catheter 5045 and into the intragastric balloon 5030. In some embodiments, a final target pressure of the intragastric balloon 5030 is 2 psi or about 2 psi. In some embodiments, a final target pressure of the intragastric balloon 5030 is between 2 psi to 5 psi or between 2 psi to 8 psi. Inflating an intragastric balloon to a pressure above 8 psi may risk injury to a patient.

The pressure gauge 5010 can be positioned between the inflation fluid container 5005 and the pressure regulator 5015. The pressure gauge 5010 can allow the pressure in the inflation fluid container 5005 to be monitored. The pressure gauge 5010 can further be configured to transmit pressure data to the computing device 5035 for processing. The computing device 5035 can monitor the pressure data received from the pressure gauge 5010 to failure of the inflation system 5000, for example, as described herein with respect to FIG. 12.

The pressure gauge 5025 can be positioned between the first valve 5020 and the intragastric balloon 5030. When the first valve 5020 and second valve 5055 are closed, the reading of the pressure gauge 5025 should be generally reflective of the pressure within the intragastric balloon 5030 after an equilibrium is reached. The pressure gauge 5025 can be configured to transmit pressure data to the computing device 5035 for processing.

The second valve 5055 can be positioned to receive inflation fluid flowing through the flexible tubing 5040C from the valve 5020 or from the intragastric balloon 5030. The second valve 5055 can be opened to permit inflation fluid to flow through the second valve 5055 or can be closed to prevent inflation fluid from flowing through the valve 5055. Inflation fluid flowing through the valve 5055 can flow out of the output opening 5060, and consequently, out of the inflation system 5000. If the first valve 5020 is open and the second valve 5055 is open, inflation fluid flowing through the first valve 5020 can flow out of the inflation system 5000 via the outflow opening 5060. If the first valve 5020 is closed and the second valve 5055 is open, inflation fluid within the intragastric balloon can flow out of the inflation system 5000 via the outflow opening 5060. In some embodiments, the second valve 5055 can be configured to open or close in response to instructions received from the computing device 5035. In some embodiments, the second valve 5055 can be a solenoid valve.

If the second valve 5055 is closed, the inflation system 5000 can operate in a similar manner as discussed herein with respect to the inflation system 4800 to inflate the intragastric balloon 5030 to a final target pressure.

Figure 28:
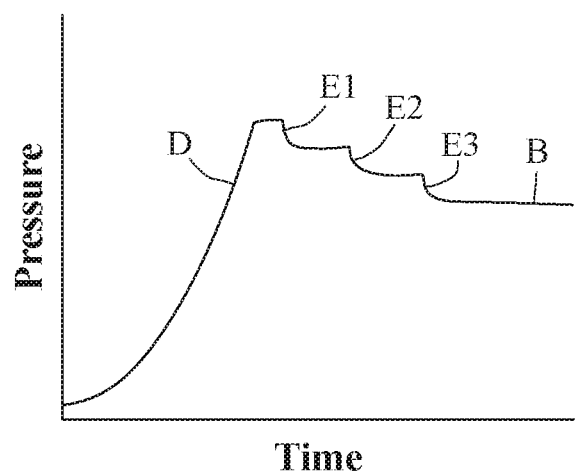
FIG. 28 depicts a graph illustrating the pressure in an intragastric balloon over time as the intragastric balloon is inflated in an exemplary operation of the inflation system 5000 of FIG. 26.

In one example of operating the inflation system 5000, the inflation system 5000 can be configured to fill the intragastric balloon 5030 to an initial bolus target pressure (e.g., D of FIG. 28) that is greater than the final target pressure B and incrementally reduce the pressure in the balloon 5030 by opening the second valve 5055 (e.g., E1, E2, E3 of FIG. 28). In some embodiments, the initial bolus target pressure is 5 psi or about 5 psi, is between 2 psi to 5 psi, or is between 2 psi to 8 psi. The computing device 5035 can provide instructions to the inflation fluid container 5005 to dispense the initial bolus D volume of inflation fluid into the inflation fluid system 5000. The initial bolus D volume of the inflation fluid may be a volume estimated to produce a final target pressure in the intragastric balloon 5030 or an initial bolus target pressure D that is greater than the final target pressure B. The first valve 5020 can be in the open position prior to dispensing of the initial bolus volume of inflation fluid from the inflation fluid container 5005 or may be opened after dispensing of the initial bolus volume of inflation fluid from the inflation fluid container 5005 to allow the initial bolus D volume of the inflation fluid container to flow through the inflation fluid system 5000 and into the balloon 5030. The second valve 5055 can be closed prior to dispensing of the initial bolus volume of inflation fluid to prevent the inflation fluid from flowing out of the outflow opening 5060.

After a defined period of time sufficient to allow the initial bolus D volume of inflation fluid to flow into the intragastric balloon 5030, the computing device 5035 can be configured to provide instructions to the first valve 5020 to close. The defined period of time can be determined by the computing device 5035. After the first valve 5020 is closed, the computing device 5035 can be configured to determine a volume (e.g., E1, E2, E3) of inflation fluid to be removed, vented or released from the intragastric balloon 5030 when the pressure in the intragastric balloon 5030 is determined to be greater than the final target pressure B based on data received from the pressure gauge 5025 after sufficient time is allowed for equilibrium to be achieved. When the first valve 5020 and the second valve 5055 are closed and equilibrium is achieved, the pressure measured by the pressure gauge 5025 is generally indicative of the pressure within the intragastric balloon 5030. In some embodiments, the computing system 5035 is configured to determine that equilibrium has been achieved after a determined period of time. In other embodiments, the computing system 5035 is configured to determine that equilibrium is achieved based on trends in the data received from the pressure gauge 5025.

After the computing device 5035 determines a volume of inflation fluid to be removed from the intragastric balloon 5030, the computing device 5035 can provide instructions to the valve 5055 to open for a determined length of time (while valve 5020 is closed) in order to allow the determined volume of inflation fluid to flow from the intragastric balloon 5030 out of the outflow opening 5060. After the valve 5055 allows the determined volume of inflation fluid to be removed from the intragastric balloon 5030, the computing device can provide instructions to the valve 5055 to close. Measurement of the pressure within the intragastric balloon 5030, determination of an additional volume of inflation fluid to be removed from the intragastric balloon 5030, and dispensing of additional volumes of inflation fluid from the intragastric balloon 5030 through the outflow opening can be repeated until a final target pressure of the intragastric balloon is achieved.

FIG. 28 depicts a graph showing an example of pressure measurements measured by the pressure gauge 5025 during inflation of an intragastric balloon inflated by dispensing an initial bolus volume D of inflation fluid and then reducing the internal pressure of the intragastric device 10 as by sequentially releasing small volumes (e.g., E1, E2, E3) of inflation fluid until the target internal pressure B is achieved, such as is described herein.

In some operations of the inflation system 5000, the inflation system 5000 can be configured to both incrementally increase the volume of the inflation fluid within the intragastric balloon 5030 and incrementally decrease the volume of the inflation fluid within the intragastric balloon 5030 following the dispensing of an initial bolus D volume of the inflation fluid by the inflation fluid container 5005. This can be desirable, for example, if the pressure in the intragastric balloon 5030 falls below a final target pressure B during an incremental decrease of the pressure within the intragastric balloon 5030 or rises above a final target pressure B during an incremental increase of the pressure within the intragastric balloon 5030. As described herein, the pressure within the intragastric balloon 5030 can be increased by dispensing an additional volume of inflation fluid from the inflation fluid container 5005 when the first valve 5020 is opened and the second valve 5055 is closed. The pressure within the intragastric balloon 5030 can be reduced when the first valve 5020 is closed and the second valve 5055 is open.

Although a separate computing device 5035 is described, one of skill in the art would recognize that the computing device 5035 may be part of one of the other components of the inflation system 5000, such as for example, the inflation container 5005. In some embodiments, the functions described with respect to the computing device 5035 may instead be performed multiple separate components of the inflation system 5000. In some embodiments, one or more functions described with respect to the computing device 5035 can be performed at one or more processing units in connection with one or more of the inflation fluid container 5005, the first pressure gauge 5010, the pressure regulator 5015, the first valve 5020, and the second pressure gauge 5025, and the second valve 5055.

FIGS. 29-37 illustrates an automated dispenser 5200 that may be configured similar to system 4800 or system 5000, for use with the intragastric device system described elsewhere herein. The dispenser 5200 may comprise a housing 5205 to surround a pressurized canister 2003 in order to lock and hold the canister 2003 in place. The housing 5205 may surround the canister 2003, in part or in full, and may provide a visual indicator (not shown in the FIG.) to enable an operator to gauge the remaining pressure in the canister 2003. The canister housing 5205 may comprise a locking mechanism 5206 to allow an operator to install, and lock into place, a canister 2003 of pressurized matter. The locking mechanism 5206 may also allow the operator to safely release and remove the pressurized canister 2003. Attached to the canister housing 5205 is a tunnel housing 5203 comprising in part a tunnel 5207 providing a trajectory into which the contents of the canister 2003 may be released. The tunnel 5207 can allow for the directional flow of the content of the canister 2003, and may also allow for manipulation of the flow through a plug valve 5202. The plug valve 5202 may be situated in an orthogonal orientation relative to the tunnel 5207 to allow interruption or prevention of the flow of the canister contents within the tunnel 5207. The tunnel 5207 may include a vent valve 5201. For example, a vent valve 5201 located between the plug valve 5202 and the canister 410 may allow for atmospheric normalization between the s system and the surrounding pressure. The tunnel housing 5203 may provide sufficient structural strength as to prevent damage to, or compromise the structural integrity of, the tunnel 5207 caused by the pressurized contents of the canister or other potential damage caused by shock, vibration, etc. The tunnel housing 5203 may also provide a structure for which additional components may be installed.

Figure 42:
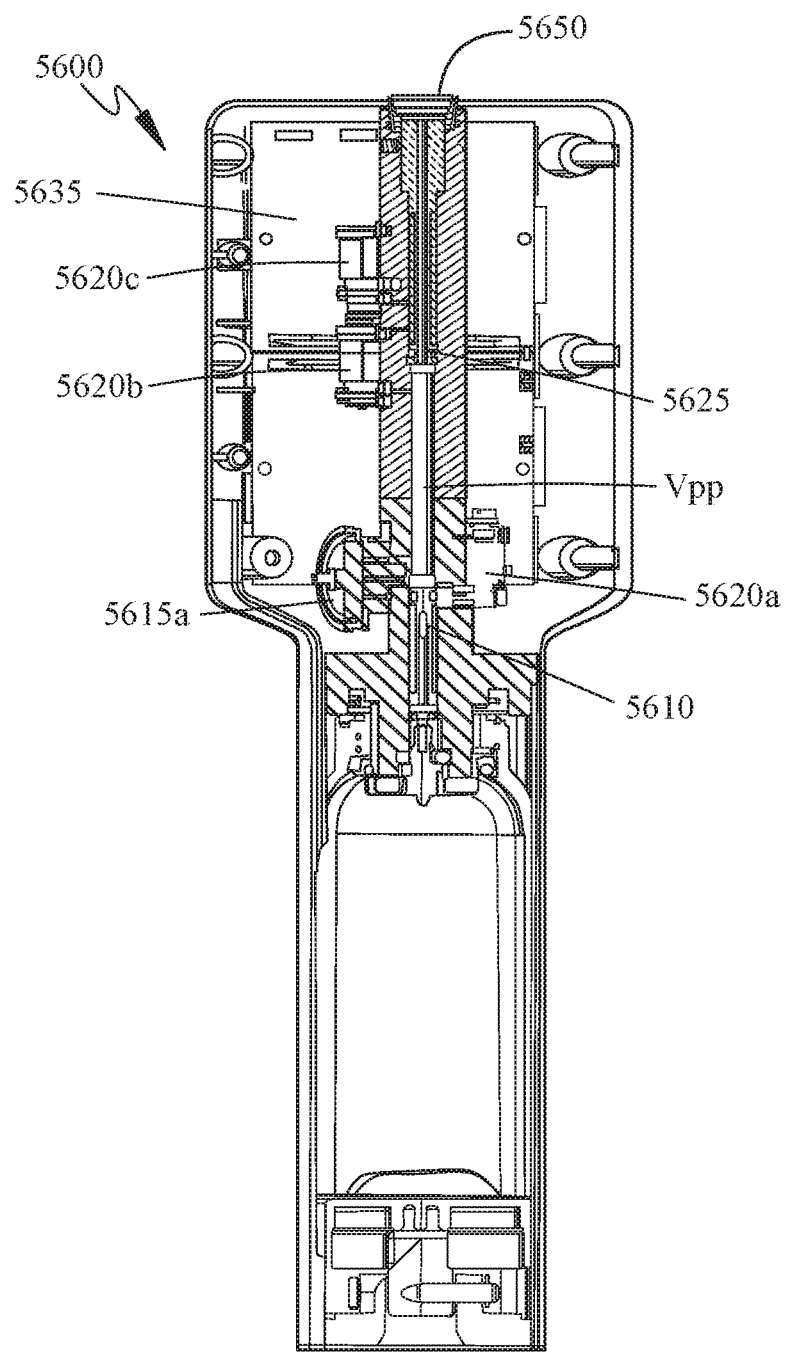
FIG. 42 is a bottom cross-sectional view of the Dispenser 5600 of FIG. 39 with the cross-section being taken along line 42-42 of FIG. 44.

As further illustrated in FIG. 42, the tunnel housing 5203 may be connected to the canister housing 5205 in a manner which allows for the tunnel 5207 to direct the flow of the pressurized contents of the canister 2033. In one embodiment, the tunnel housing 5203 is connected with the canister housing 5205 using an O-ring seal 5209 and a number of screws to fasten the two components together. The connection may also comprise gaskets, gasket sealing adhesives, or any other fastener or sealer sufficient to prevent damage of the components from pressure.

Figure 29:
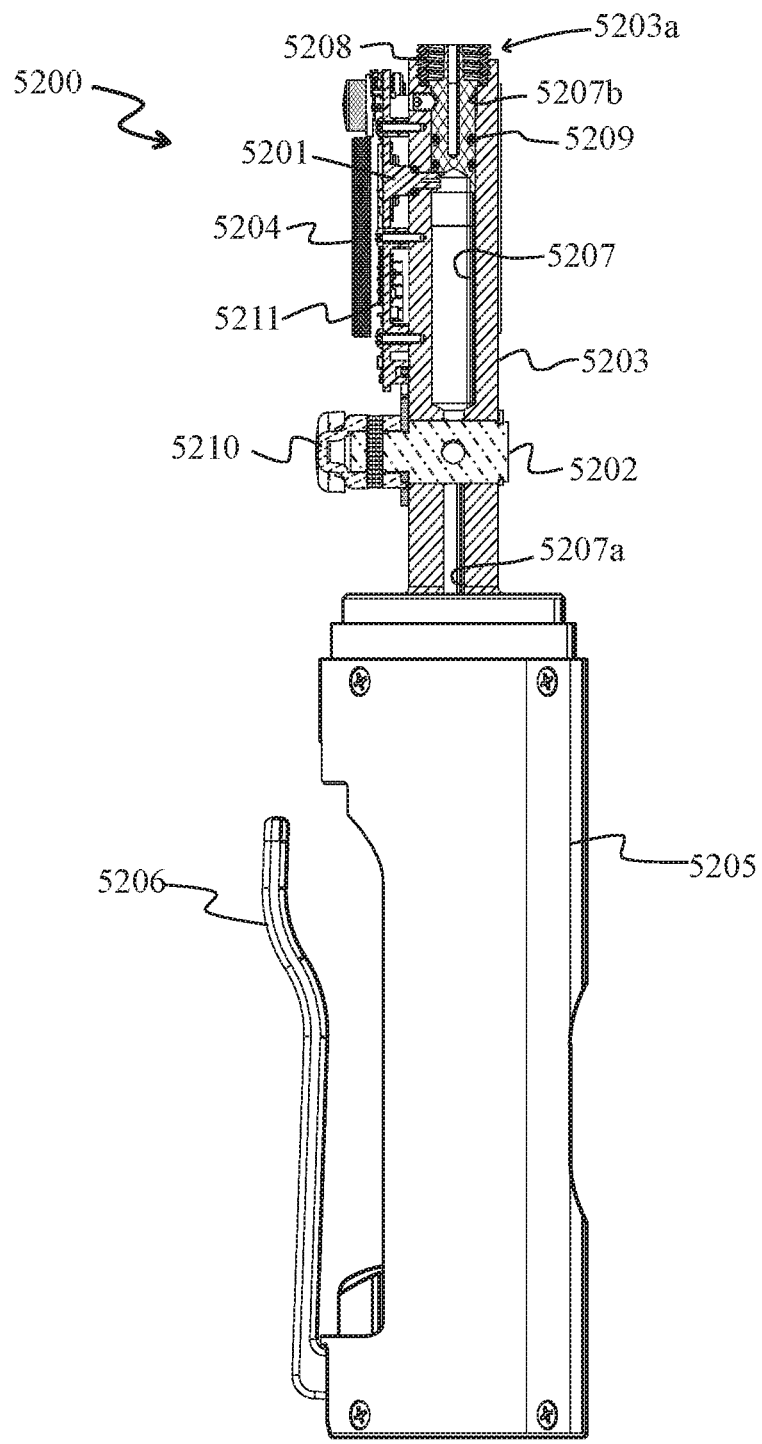
FIG. 29 is a side view of an exemplary embodiment of a dispenser 5200 for use with an inflatable intragastric device system 1915, 30, wherein portions of the dispenser are shown in cross-section, the cross-section being taken along line 31-31 of FIG. 30.

As previously stated, the tunnel housing 5203 may provide a structure for support of additional components. For example, FIG. 29 provides an exemplary embodiment wherein the tunnel housing 5203 provides structure for a plug valve handle 5210, a touch sensitive display 5204 and related circuitry 5211, a quick disconnect valve 5208, and a solenoid vent valve 5201.

The plug valve 5202 may be manually operated using a plug valve handle 5210 attached to the plug valve 5202 outside of the tunnel housing 5203. Such a configuration may allow for the operator to manually adjust the pressure seen by the tunnel 5207. In one example embodiment, the plug valve 5202 may be adjustable by a handle 5210 that allows the operator to twist the valve 5202 open and shut, such as in response to instructions provided by the computer system. In another example embodiment, the valve 5202 may be adjustable by pushing or pulling the valve 5202 open and shut, such as in response to instructions provided by the computer system. Another exemplary embodiment may include a plug valve 5202 that can be electronically activated by either (1) operator feedback or instruction, or (2) electronically adjusted through automated feedback from a processor. In another exemplary embodiment, the plug valve 5202 may include a plug valve channel 5202a that is fluidly engageable with the tunnel 5207, such that when the channel 5202a is longitudinally aligned with the tunnel 5207, the pressurized fill fluid may flow therethrough, and when the channel 5202a is misaligned with the tunnel 5207, the flow therethrough is substantially blocked. Accordingly, the operator may control flow of the pressurized fluid by rotating the valve handle 5210, to move the valve channel 5202a to either an aligned position or a non-aligned position, relative to the tunnel 5207. Alternatively, positioning of the valve channel 5202a can be controlled electronically via the circuitry 5211.

The dispenser 5200 may also comprise a quick disconnect valve 5208 affixed to a distal end 5203a of the tunnel housing 5203 in order to allow an operator of the system to attach a catheter 5400a or 5400b to an exit point of the tunnel housing 5203. The tunnel 5207 may direct the flow of the pressurized matter into the catheter 5400a or 5400b in this manner. The disconnect valve 5208 may be fastened to the tunnel housing 5203 using an adhesive or mechanical fastening means. In one exemplary embodiment, the connection between the housing 5203 and the disconnect valve may be sealed with an O-ring 5209 or other type of sealant (e.g., adhesive, gasket, weld). The disconnect valve 5208 may provide a port for connection to the catheter connection assembly 5400a or 5400b. The disconnect valve 5208 may further comprise an electromechanical means for alerting the system to when a catheter assembly 5400a or 5400b is connected to the valve, or when there is no peripheral connection.

Figure 30:
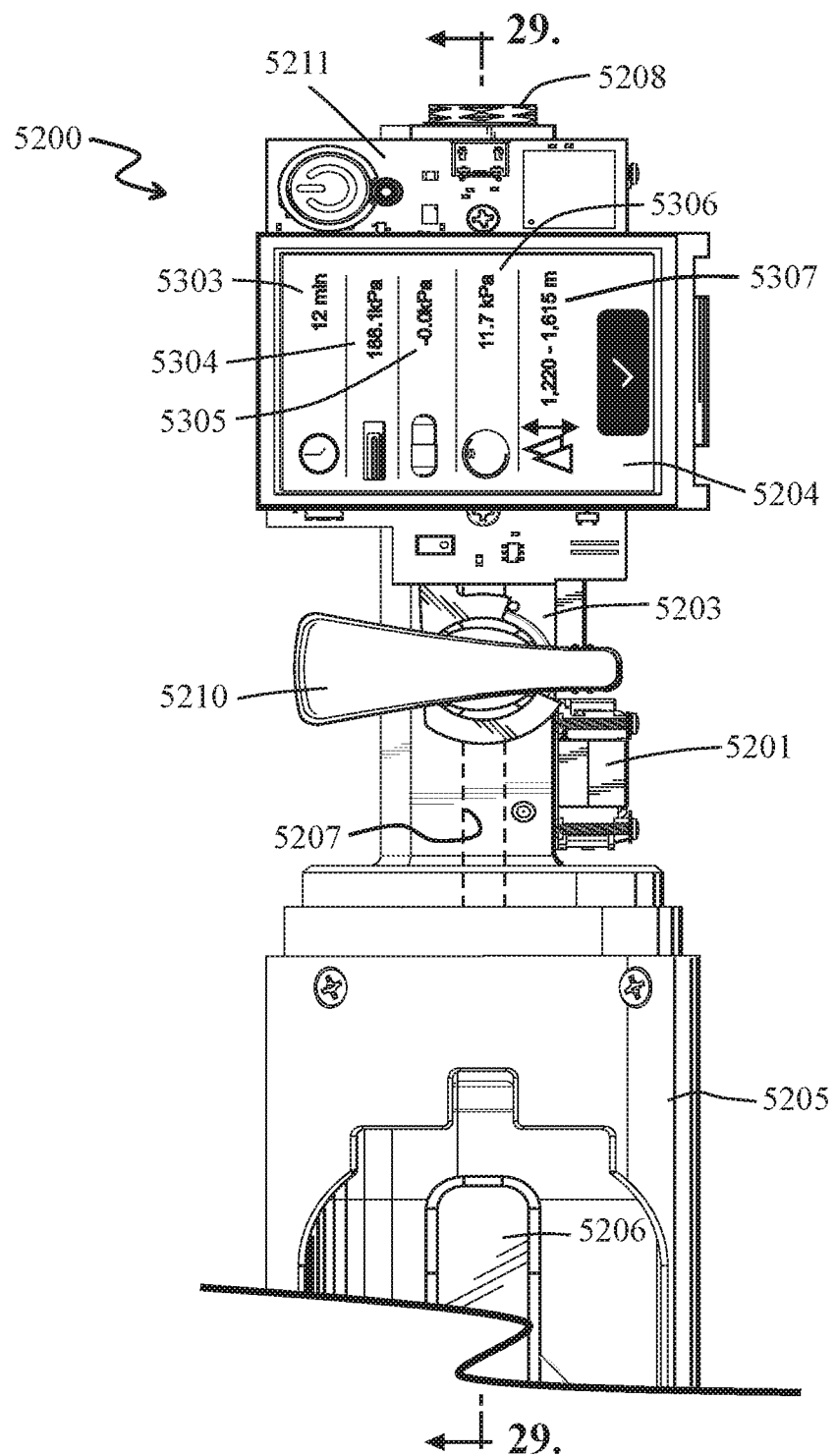
FIG. 30 is a front view of the dispenser 5200 of FIG. 29, with portions cut away, a touch screen housing 5201 not shown and a tunnel 5207 shown in phantom.
Figure 31:
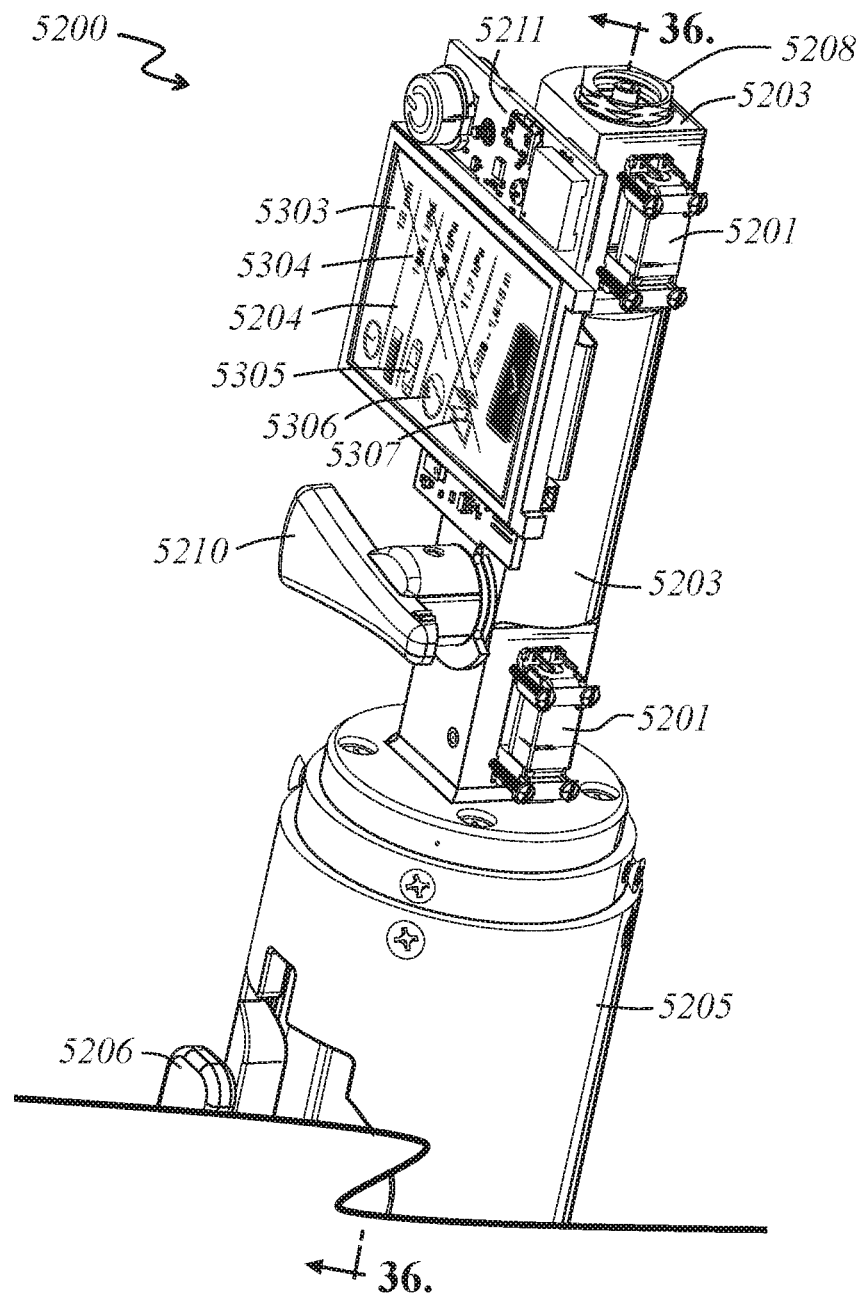
FIG. 31 is a front perspective view of the dispenser 5200 of FIG. 29, with portions broken away and the touch screen housing 5201 not shown.

As further illustrated in FIGS. 30-31, the tunnel housing 5203 may provide structure to support a solenoid vent valve 5201. The solenoid vent valve 5201 may allow for atmospheric normalization between the pressure in the intragastric device 10 and the pressure in the surrounding atmosphere. The vent valve 5201 may be controlled by an electric current through a solenoid 5201 that is activated when a pressure difference is detected between the intragastric device 10 and the surrounding atmosphere. In one exemplary embodiment, the solenoid 5201 may be activated automatically upon connection of the catheter connection assembly 5400 to the disconnect valve 5208 when the catheter assembly 5401 triggers the electromechanical means for alerting the system to a catheter 5400 connection. In another exemplary embodiment, the solenoid 5201 can be activated automatically by one or multiple pressure transducers (not shown in FIG.) that monitor the pressure of the intragastric device 10 and also the atmospheric pressure when a pressure transducer senses a delta (i.e., Δ, a difference or change in a certain quantity), between the two environments.

FIG. 30 illustrates further the connection between the canister housing 5205 and the tunnel housing 5203, as well as the structural support provided by the tunnel housing to accommodate an adjustable plug valve 5202 and plug valve handle 5210, a solenoid vent valve 5201, quick disconnect valve 5208, and a touch sensitive display 5204 with related circuitry 5211.

FIG. 30 also illustrates an exemplary embodiment of the touch screen display 5204. The touch screen display 5204 may provide information to the operator of the system, about the system. For example, the touch screen display 5204 may provide a time monitor 5303 that can show the time elapsed since the initiation of the procedure. The time indication 5303 may also provide a normal clock, timer, stop-clock or alarm system. The operator may toggle and edit these features using the touch screen 5204.

FIG. 30 further illustrates a touch screen display 5204 comprising a real-time indicator of canister pressure 5304. The indicator of canister pressure 5304 may be adjustable by the operator to show pressure, of the canister 410, in different measuring units or increments.

FIG. 30 further illustrates a touch screen display 5204 comprising a real-time indicator of catheter internal pressure 5305. As with the indicator of canister pressure 5304, the catheter pressure indicator 5305 may be adjustable by the operator to show pressure within the catheter 5400 in different measuring units or increments.

FIG. 30 further illustrates a touch screen display 5204 comprising a real-time indicator of intragastric device pressure 5306. As with the indicator of canister pressure 5304, the intragastric device pressure indicator 5306 may be adjustable by the operator to show intragastric device pressure in different measuring units or increments.

FIG. 30 further illustrates a touch screen display 5204 comprising a real-time indicator of ambient atmospheric pressure 5307. As with the indicator of canister pressure 5304, the ambient atmospheric pressure indicator 5307 may be adjustable by the operator to show ambient pressure in different measuring units or increments.

FIG. 30 further illustrates a touch screen 5204 comprising a touch-screen button 208 or similar graphical input device. The touch-screen button 5308 may be actuated by the operator, such as in response to queries by the device 5100 or at the completion of steps in a balloon implantation procedure.

Figure 32:
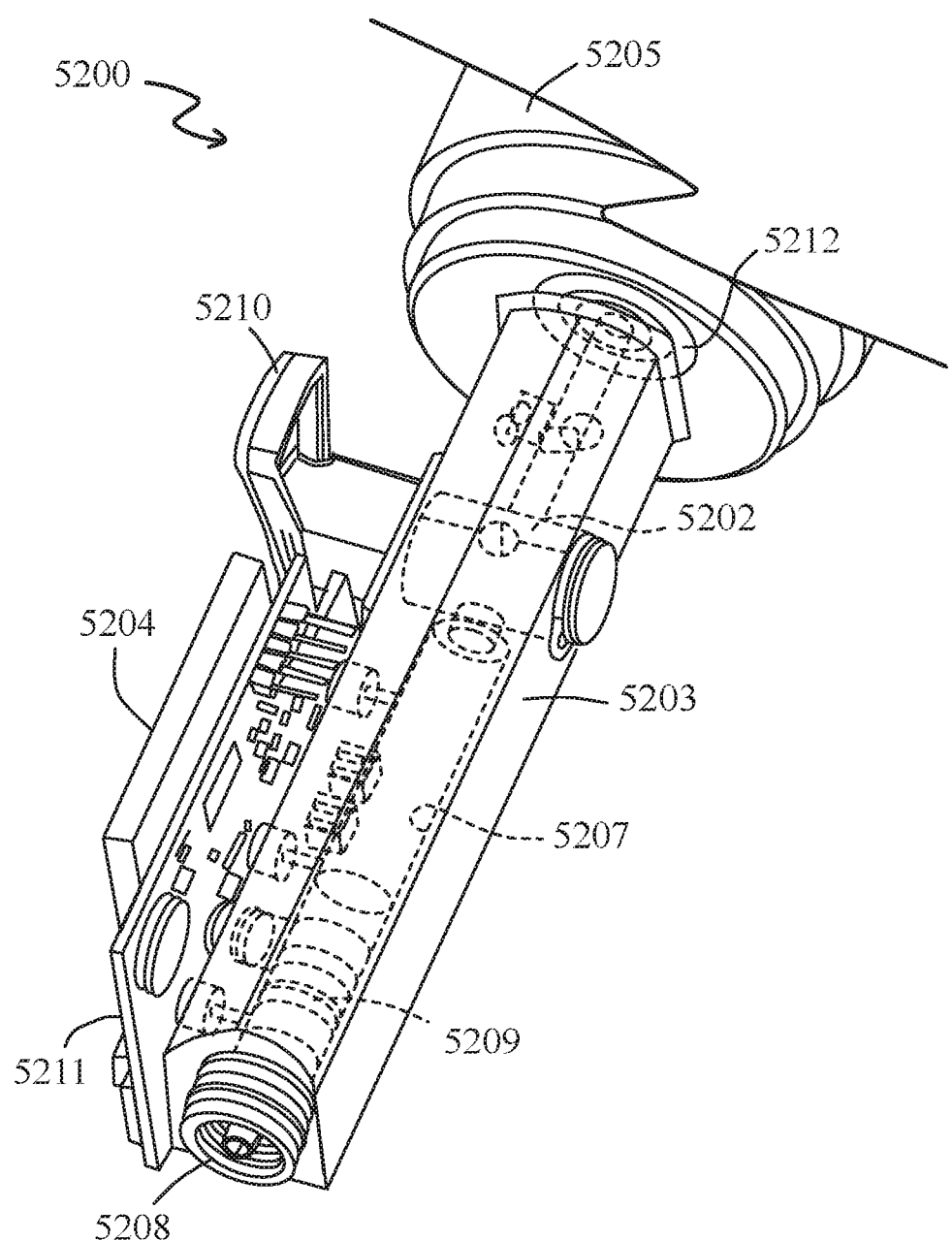
FIG. 32 is a rear perspective view of the dispenser 5200 of FIG. 29, with portions broken away, the touch screen housing 5201 not shown and the tunnel 5207 shown in phantom.

FIG. 31 and FIG. 32 provide different views of the features provide in FIGS. 29 and 30.

Figure 33:
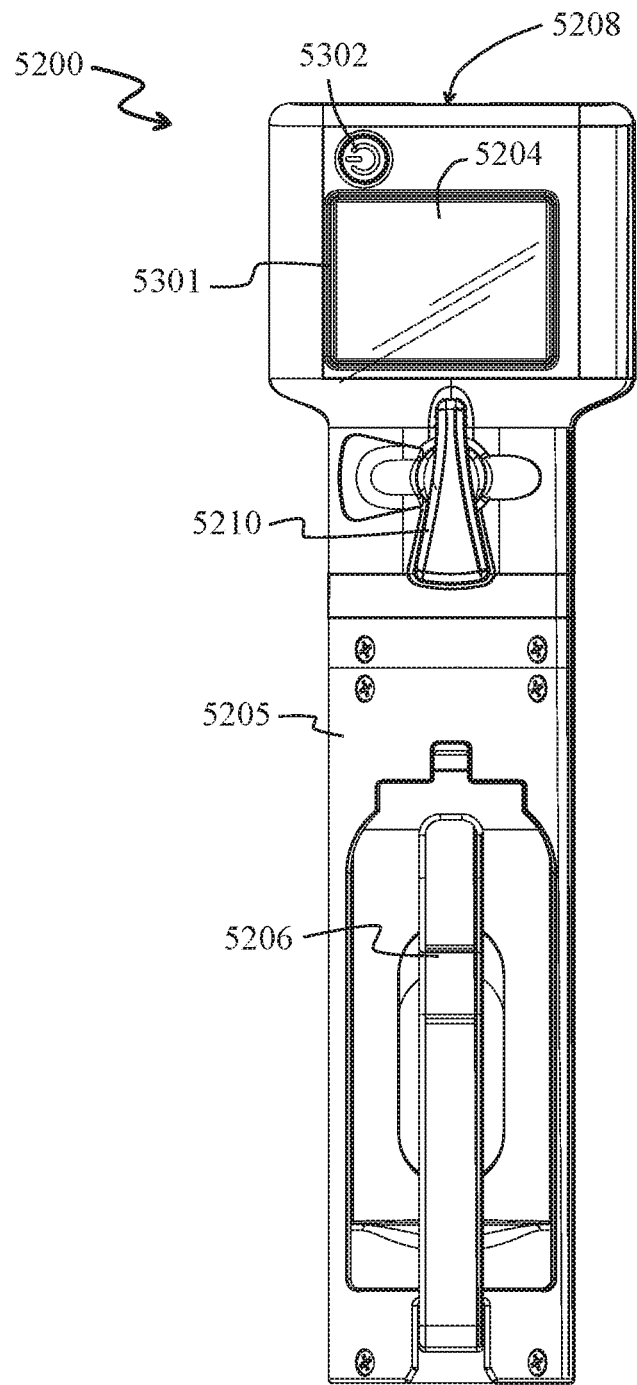
FIG. 33 is a front view of the dispenser 5200 of FIG. 29, including the touch screen housing 5201.

FIG. 33 provides a view of the dispenser 5200 wherein a housing 5301 for the touch screen circuitry 5211 and the plug valve 5202 is installed. The housing 5301 may provide a protective shell for the circuitry from operator misuse, dropping, liquid spilling, biological contamination, or another hazard. The touch screen housing 5301 may have an opening with a push button interface 5302 to allow the operator to toggle power to the dispenser 5200 on and off. The power toggle 5302 may be a touch sensitive interface, a push button interface, a switch, or any other apparatus that allows for operator modulation of power. The touch screen housing 201 may attach to the dispenser 5200 through any adhesive or mechanical fastening means, and may further comprise at least one O-ring, gasket seal, or other means for sealing the apparatus.

FIG. 34A provides a view of a portion of an exemplary catheter 5400a including a two-way luer activated valve 5404 coupled to the dispenser connection assembly 5401 to allow for automatic pressure normalization between the intragastric device and pressure relative to the catheter 5400a. Such a configuration makes the catheter 5400a safer for use on patients by automating the valve system as opposed to a manual configuration, and provides a "plug-n-play" functionality. The structure and features illustrated in FIG. 34A are described in detail below.

FIG. 34B provides a view of a portion of another exemplary catheter 5400b including syringe-activated valve 5307.

Figure 35:
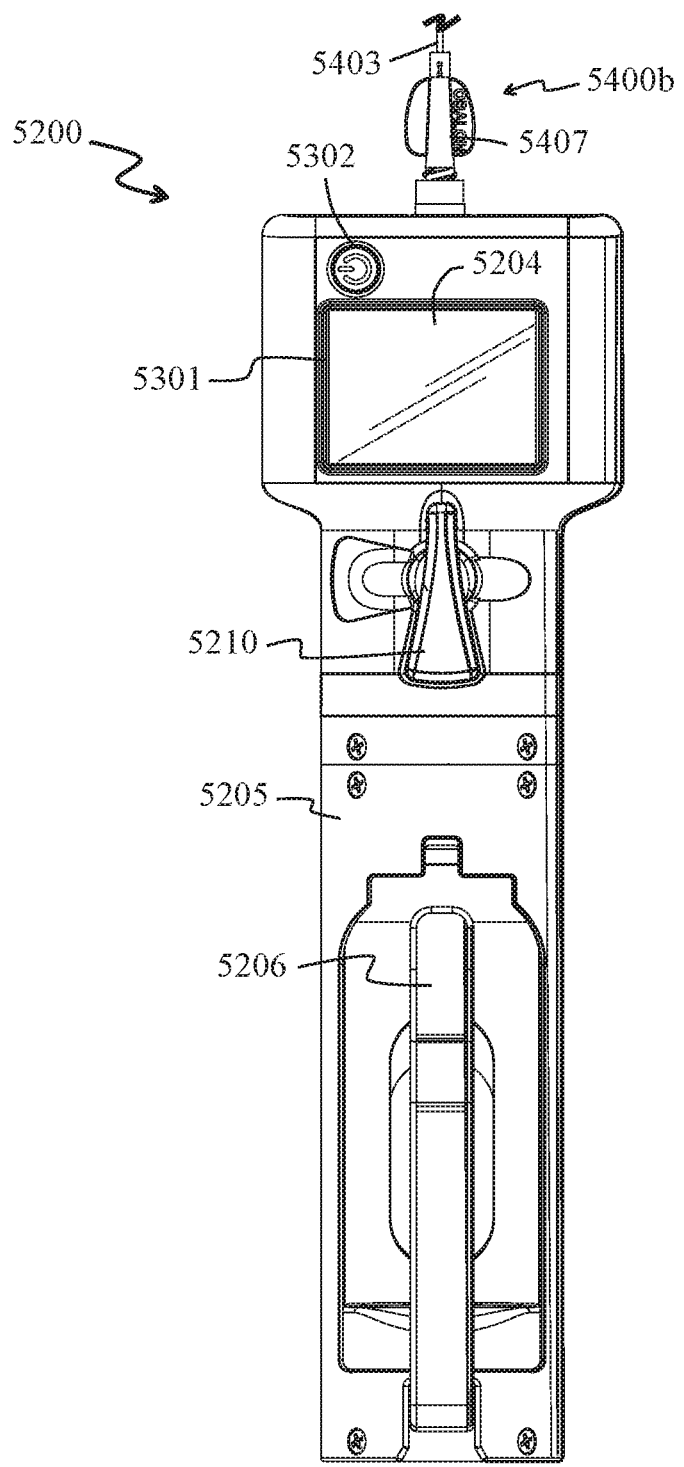
FIG. 35 is a front view of the dispenser 5200 of FIG. 29 with a catheter connection assembly 5400*b* of FIG. 36B attached to a dispenser quick disconnect valve 5208.

FIG. 35 illustrates the dispenser device 5200 of FIG. 33 with a self-sealing valve system 5401 installed on the disconnect valve 5208.

Figure 36:
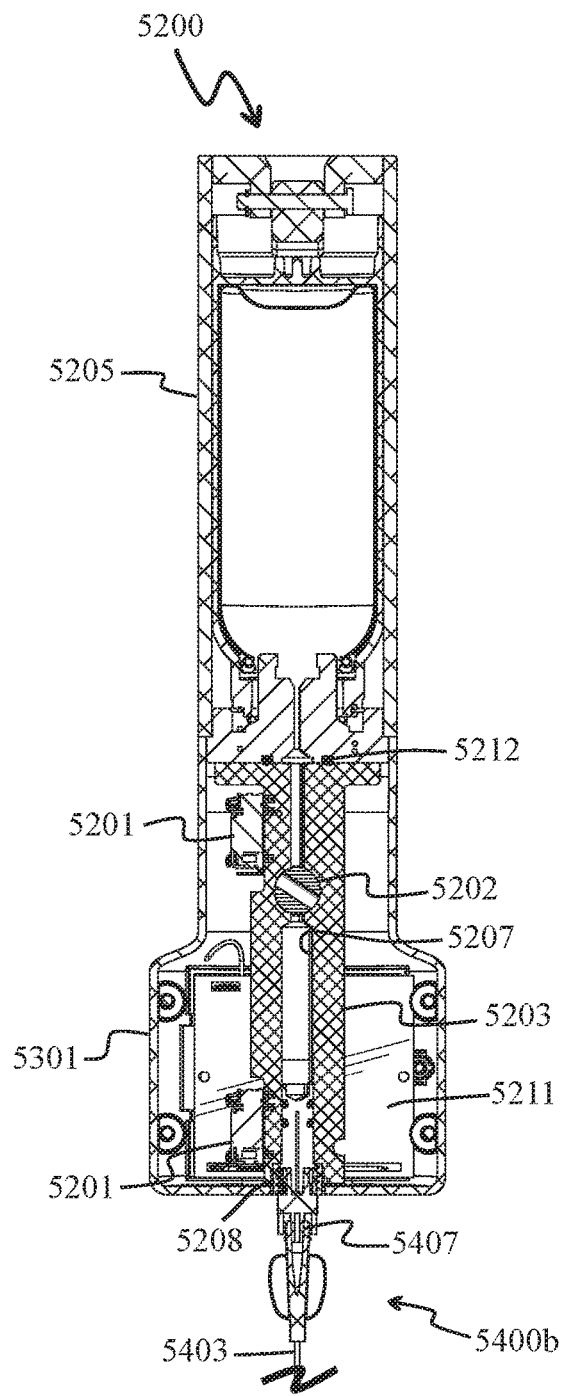
FIG. 36 is a cross-section of the dispenser 5200 of FIG. 29, the cross-section being taken along line 38-38 of FIG. 33.

FIG. 36 illustrates a cut-away view of the dispenser 5200 that allows one to view the internal structure of the device as displayed in FIGS. 33, 35-37 with the touch screen housing 5301 installed.

Figure 37:
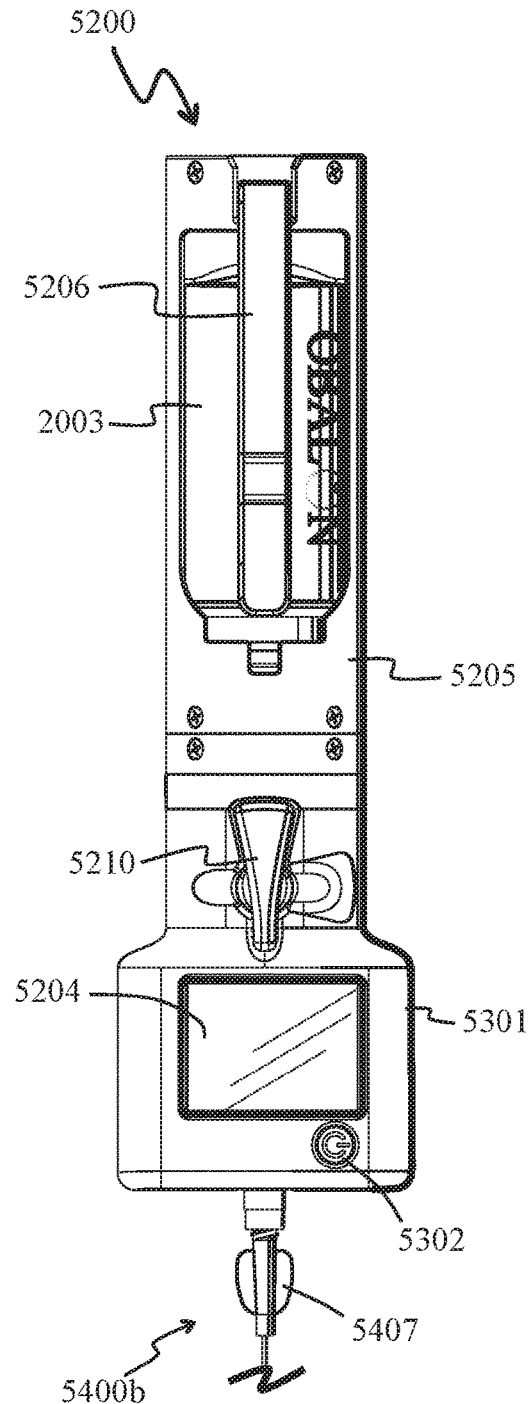
FIG. 37 is a front view of the dispenser 5200 of FIG. 29 with a fill fluid canister 2003 engaged in a canister housing 5205 and locked in place by a locking mechanism 5206.

FIG. 37 illustrates the dispenser 5200 with the inflation fluid canister 2033 installed.

Figure 38:
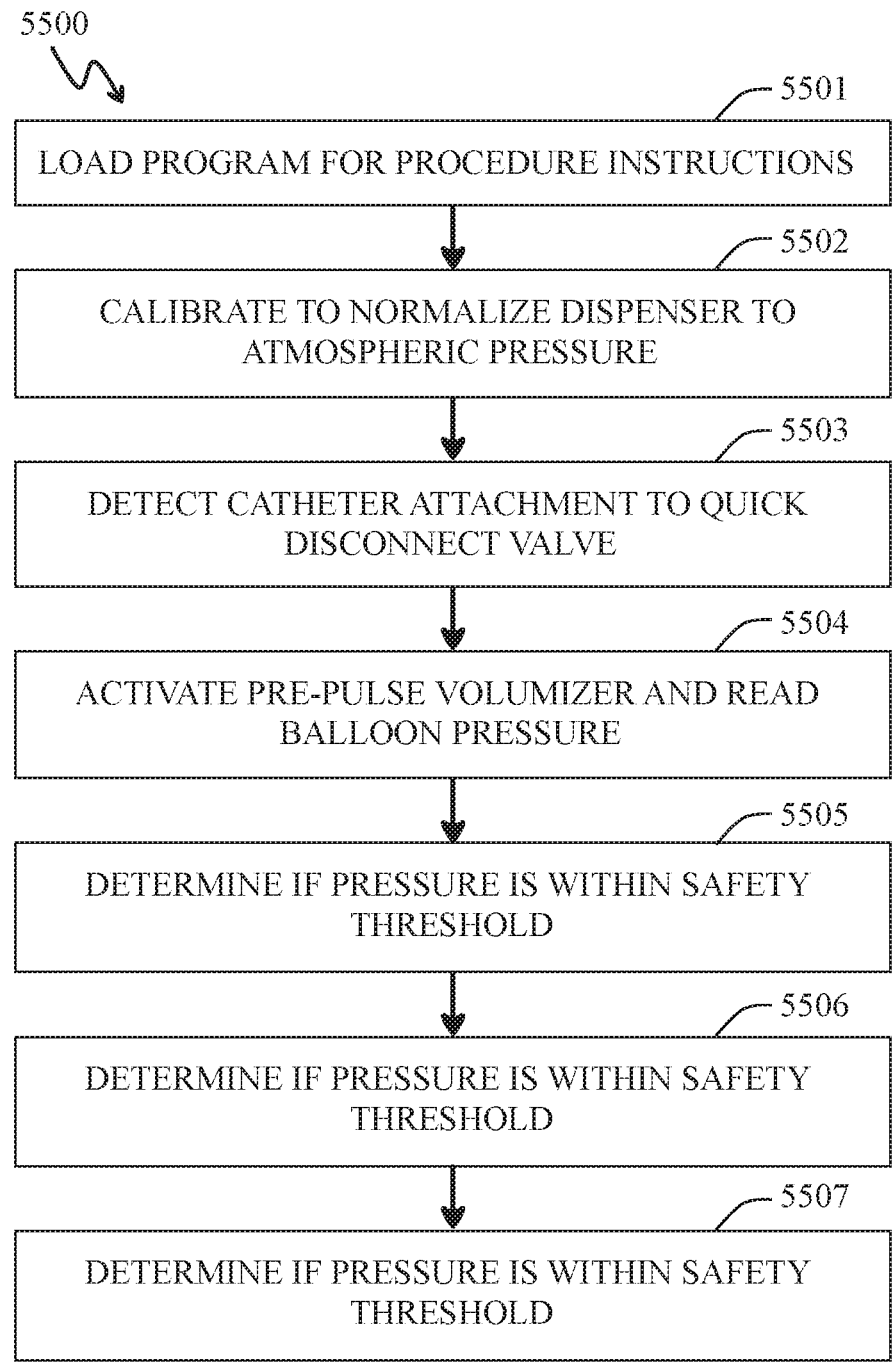
FIG. 38 is a flow chart 5500 illustrating steps in using the dispenser 5200 of FIG. 42 to inflate an inflatable intragastric device.

FIG. 38 illustrates an exemplary method 5500 by which the dispenser 5200 may operate with the intragastric device system. Initially, a program is loaded 5501 onto the dispenser 5200, specifically the circuit element 5211 which may include processors and memory units. The program loaded onto the dispenser 5200 may be one of a plurality of programs tailored for a specific application, or may be a single program with adjustable features that allow the operator of the dispenser 5200 to calibrate according to a particular situation or need. The program may provide a set of directions in a visual format on the display screen 5204, or may provide an audio set of directions.

Further to FIG. 38, the dispenser 5200 may calibrate 5502 the dispenser and peripheral objects to normalize the sensed pressure of the intragastric balloon and the sensed pressure of the catheter 5400a or 5400b and tunnel 5207 to the surrounding atmospheric pressure. This may allow for use of the intragastric device system in location of varying elevations.

The dispenser 5200 may also detect 5503 connection of the self-sealing valve 5401 of a catheter 5400a or 5400b to the quick disconnect valve 5208. The disconnect valve 5208 may further comprise an electromechanical means for alerting the system to when a catheter assembly 5400a or 5400b is connected to the valve 5208, or when there is no peripheral connection.

Further to FIG. 38, the dispenser 5200 may activate 5504 a pre-pulse volumizer. In one example embodiment, the dispenser 5200 may release a configurable volume and pressure from the canister 2003 into the intragastric balloon to determine whether the balloon is constrained in the esophagus. In another embodiment, a metered pre-pulse may release high-pressured gas contained in the canister 2003 into the intragastric balloon through the catheter 5400a or 5400b in short, timed doses, while the dispenser 5200 measures the pressure of the balloon as the metered pre-pulse releases progresses. The pre-pulse volumizer may partially inflate the intragastric balloon allowing the operator of the device to determine 505 whether the intragastric balloon is safe to inflate.

FIG. 38 further illustrates a method whereby once the operator of the dispenser 5200 has determined the intragastric balloon is safe to be further inflated, the operator may open the plug valve and instruct the dispenser 5200 to activate 5506 the primary volumizer to inflate the balloon to its fully inflated state and provide a reading of the pressure within the intragastric balloon.

The method described in FIG. 38 may also include termination 5507 of the primary volumizer once a certain pressure within the balloon is detected.

Touch Screen

As previously discussed, the dispenser 5200 may comprise a computer-implemented method for use in conjunction with an intragastric volume occupying system with a touch sensitive display 5204 to detect user gestures on a touch screen 5204 and translate the user gestures into commands to be performed.

In one embodiment, the touch screen 5204 may be housed in a touch screen housing 5201 comprised of a material such as a metal, or polymer or other plastic material attached to the dispenser 5200. The surface area of the touch screen 5204 that comes in contact with the housing 201 may be made waterproof by incorporating a gasket or adhesive material to seal the touch screen 5204 in contact with the housing 201. The housing 201 may have a window generally the length and width of the touch screen 5204 area to allow users to see and touch the touch screen 5204 surface when the touch screen 5204 is mounted to the housing 201.

The touch screen circuitry 5211 or the touch screen 5204 may provide I/O ports for attaching peripheral hardware, for example a printer, keyboard, mouse, monitors, headphone and microphone jacks. The circuitry 5211 or touch screen 5204 may also provide options for a wireless connection including, for example, Bluetooth, Wi-Fi or WLAN.

In one exemplary embodiment, the dispenser 5200 may include a display 5204 without a touch sensitive screen. In this example, the display 5204 may provide a visual display of the data described above and may also allow for user interface through means including, but not limited to, voice activation, Bluetooth, Wi-Fi 33 or WLAN, integrated button control, and I/O ports for attaching peripheral hardware, for example a printer, keyboard, mouse, monitors, headphone and microphone jacks.

In some embodiments, the touch sensitive display 5204 may be physically integrated with various electronic elements 5211 including, for example, one or more processors, memory (which may include one or more computer readable storage mediums), I/O ports (e.g., USB ports, micro USB ports, audio and video ports, Ethernet, Wi-Fi 33, and RFID), a battery, and a set of push button controls. The I/O ports couple the input and output of any peripherals of the dispenser 5200 to the CPU and memory. The one or more processors may run or execute various software programs and/or sets of instructions stored in memory to perform various functions for the device and to process data.

In another example embodiment, the touch screen 5204 may display a Graphical User Interface (GUI) and one or more programs or sets of instructions stored in the memory for performing multiple functions. In one example embodiment, the user interacts with the GUI primarily through finger contacts and gestures on the touch sensitive display 5204. In some embodiments, GUI functions may include digital photographing, digital videoing, digital audio playing, digital video playing, instructions for performing a plurality of procedures with the device and intragastric system, displaying diagnostic information for the intragastric system and any individual component or sensor connected to the system. Instructions for performing these functions may be included in a computer readable storage medium or other computer program product configured for execution by one or more processors. The integrity of the programming may be protected using a combination login and password prompt upon startup. The programming may further be encrypted through the use of fingertip detection, smart card identification, or magnetic-read identification. These parameters may further be implemented to prevent misuse of the dispenser 5200 or to allow limited access to the use of the dispenser 5200. In another example embodiment, the GUI may comprise a memory controller, one or more processing units (CPU's), a peripherals interface, RF circuitry, audio circuitry, a speaker, a microphone, an input/output (I/O) subsystem, other input or control devices, and an external port. The device may include one or more optical sensors. These components may communicate over one or more communication buses or signal lines.

In another embodiment, the dispenser 5200 may include a memory (which may include one or more computer readable storage mediums), a memory controller, one or more processing units (CPU's), a peripherals interface, RF circuitry, audio circuitry, a speaker, a microphone, an input/output (I/O) subsystem, other input or control devices, and an external port. The device may include one or more optical sensors. These components may communicate over one or more communication buses or signal lines.

Catheter

A swallowable, self-inflating or inflatable intragastric balloon system according to selected preferred embodiments includes the following components: self-sealing valve system 1000 (e.g., FIGS. 3A-3D) for addition of fluid to the lumen of the balloon or to the inner container ("valve system"), a balloon in a deflated and compacted state ("balloon") and an outer capsule, container, or coating ("outer container") that contains the balloon, the outer container being optional. For self-inflating balloons, an inner capsule or other container ("inner container") that contains one or more $CO_2$ generating components is present inside the lumen of the balloon, the inner container being optional. For inflatable balloons, an inflation fluid source, a catheter 5400a or 5400b and tubing 5403 ("inflation assembly") are provided for inflating the balloon after ingestion or placement in the stomach. In the self-inflating balloon configuration, the valve is preferably attached to the inner surface of the balloon by an adhesive or other means (e.g., welding), and provided with an inoculation spacer to prevent puncture of the wall of the balloon and inner container by a needle or other means for injecting a liquid activation agent into the lumen of the balloon via the self-sealing valve. A valve providing releasable attachment of the tubing to the balloon is provided in the inflatable balloon configuration. Preferably, the self-sealing valve system attached to the balloon (e.g., on its inside surface) in the inflatable configuration is "universal" or compatible with a swallowable catheter 5400a or 5400b or a physician-assisted catheter 5400a or 5400b. The valve system serves to allow for balloon inflation using a miniature catheter 5400a or 5400b that includes a needle assembly and also provides a mechanism for detachment of the catheter 5400 after inflation has been completed.

As shown in FIG. 34A, the catheter 5400a may comprise a two-way luer activated valve 304 coupled to the dispenser connection assembly 5401 to allow for automatic pressure normalization between the intragastric device and pressure relative to the catheter 5400. Such a configuration makes the catheter 5400 safer for use on patients by automating the valve system as opposed to a manual configuration, and provides a "plug-n-play" functionality.

Further illustrated in FIG. 34A, the dispenser connection assembly 5401 may also comprise an O-ring seal 5402 at the disconnect valve 5208 connection point. The O-ring 5402 can provide a seal to prevent pressure escape at the connection point, and may alternatively be constructed of any adhesive or molding sufficient to prevent release of pressure.

The connection assembly 5401 may also comprise a one-way valve 5406 for back-flow prevention. For example, the valve 5406 may prevent backflow of ejection fluid. The valve 5406 may allow an operator to release the pressurized contents from the canister 2003 into the intragastric device, but prevent the device from re-pressurizing the canister 2003 or dispenser 5200 after emptying. It may further allow for the catheter 5400 to be removed from the dispenser 5200 and attached to another dispenser 5200 or other compatible device without releasing pressure from the intragastric device.

The connection assembly 5401 may further comprise a sealed navigation port 305 to allow an operator to navigate and control the catheter tube 5403 in areas that prevent the operator from directly handling.

Valve

As discussed above, a plug valve 5202 and a vent valve 5201 may be configured to be integrated with the dispenser 5200. The vent valve 5201 may be configured to normalize a pressure within the dispenser 5200 or the intragastric device to the surrounding atmospheric pressure to allow for consistent use of the intragastric system, including the intragastric balloon, in regions of varying elevation. The vent valve 5201 may further be configured to release an amount of pressure, a "pre-pulse volume" of a pressurized amount dependent on the surrounding atmospheric pressure. This pre-pulse volume may be released upon connecting the catheter 5400a or 5400b to the quick disconnect valve 5208. In an exemplary embodiment, the pre-pulse volume may be 3 ml. Once the intragastric volume occupying device is inside of the patient, the release of the pressure may partially inflate the intragastric balloon. This pressure may provide information to the dispenser 5200 regarding the location of the balloon in a patient's body by comparing the amount of pressure provided by the pre-pulse with the amount of pressure sensed after the release of the pre-pulse volume. For example, once the pre-pulse volume is released into the balloon, the catheter 5400a or 5400b may sense the pressure within the balloon and transmit the pressure data for display on the touch screen 5204. If the pressure data provided shows a pressure below 7 kPa, then the balloon can be assumed to be within the stomach 20 and safe for additional inflation. If the pressure shows 7 kPa or higher, then this may indicate that the balloon is still within the esophagus, and thus unsafe for further inflation. In one exemplary embodiment, a pressure sensor attached to the dispenser 5200 will feed information to the touch screen display 5204 and touch screen display circuitry 5211 in order to display the pressure after release of the pre-pulse volume and notify the user of whether it is safe to apply additional pressure to inflate the intragastric balloon, or whether the balloon is not safe for additional pressure.

Touch Dispenser

FIGS. 39-47 illustrate an exemplary automated constant pressure Dispenser 5600, referred to herein as the Touch Dispenser. The Touch Dispenser 5600 performs the valve actuations and pressure monitoring during dissolution of the balloon capsule 40 and the initial opening of the balloon 10, referred to as "pre-pulse," to determine if the balloon is in the patient's esophagus or in the stomach 20, and then during subsequent inflation of the balloon 10, so as to remove the potential for use errors and reduces the risk of esophageal inflation. The Touch Dispenser 5600 is configured to detect possible balloon inflation in constrained spaces, such as but not limited to the esophagus or a hiatal hernia, and stops balloon the inflation so as to prevent injury to the patient. Constrained spaces have a diameter that is smaller than the diameter of the fully inflated balloon. Balloon inflation within such constrained spaces can severely injure the patient and lead to death. In addition to improving the safety profile of the Obalon Balloon System, automation of the inflation process improves reliability and repeatability of the process and reduces the potential for operator errors and reduces the risk of esophageal inflation.

In one preferred embodiment, the Dispenser 5600 is configured to detect at least one constrained space during balloon inflation, and either (1) direct the physician to a failsafe procedure or (2) terminate the inflation procedure entirely, thereby preventing patient injury. If the physician follows the failsafe procedure, it may be possible to move the balloon from the constrained space into the stomach, and then to continue with the balloon administration procedure. If the failsafe procedure fails, and does not move the balloon from the constrained space into the stomach, then the Dispenser 5600 may terminate the balloon administration procedure. Once the procedure has been terminated, the balloon may be removed via endoscopy. In another preferred embodiment, the Dispenser 5600 is configured to detect and/or distinguish between at least two constrained spaces. For example, if the patient swallowed the balloon successfully, and a first constrained space is not detected, and the dispenser may determine if the balloon is within either (1) the stomach or (2) another (e.g., second) constrained space, such as but not limited to a hiatal hernia. If a second constrained space is detected, the dispenser may be able to direct the physician to perform a second fail-safe procedure to cause the balloon to move from the second constrained space into the stomach, and then procedure with the balloon administration procedure. If such a second fail-safe procedure fails, or if the physician is not able to perform such a second fail-safe procedure, then the Dispenser 5600 may be configured to direct the physician to remove the balloon endoscopically. In certain embodiments, there may be no second fail-safe procedure for moving the balloon into the stomach from the second constrained space, and the Dispenser 5600 will terminate the balloon administration procedure. In a further embodiment, when the balloon is detected to be in a constrained space, such as either of the first and second constrained spaces, the Dispenser 5600 is configured to vent a portion of gas from the balloon to the atmosphere, thereby reducing the pressure or stress on the patient's tissues by the constrained balloon.

In the illustrated embodiment, the Touch Dispenser 5600, or inflation system, is used to transfer an inflation gas (e.g., from the Inflation Can 5605) to an intragastric balloon (e.g., 5630, such as but not limited to the Obalon Gastric Balloon Assembly, described above) while the balloon is within a patient's stomach 20. The pressurized Inflation Can 5605 is pre-filled with a specific mass of a mixture of $SF_6$ and $N_2$ gases and utilizes a seal that maintains the gas content and purity for the useful life of the can 5605. The gas content is sufficient or great enough such that the Inflation Can 5605 can be used at any elevation within 0 to 8000 ft. The seal on the Inflation Can 5603 is designed to engage with the Dispenser 5600 such that the can 5605 is only open when actuated by the Dispenser 5600. The Inflation Can 5603 has a shelf-life of at least 6 months.

The Dispenser 5600 is prepared for use outside of the patient environment and its readiness is verified prior to any balloon administration. The Device 5600 provides an automated system to accurately inflate the Balloon to the correct pressure, minimize the probability of esophageal or hiatal hernia damage, provide self-diagnostic capabilities, and provide feedback to the user. To ensure that the balloon is deployed in the correct location (e.g., the stomach) at the correct time, the Device 5600 contains pressure sensors, regulators, and valves which monitor and limit the balloon inflation pressure when necessary to ensure proper placement thereof. The Dispenser 5600 includes an internal computing device 5635, or computing component, with software that provides a Graphic User Interface and controls gas flow to allow balloon inflation at any elevation within 0 to 8000 ft. The Dispenser software verifies its own readiness, e.g., it is working correctly, the batteries have sufficient energy to power the dispenser for the entire balloon administration and inflation procedure, the Inflation Can 5605 contains a sufficient amount of gas to fill the balloon 5630, and the like, prior to balloon administration and verifies balloon integrity (e.g., the balloon is inflated in a nonconstrained space, such as the stomach and there are no leaks) prior to completion of the procedure.

Figure 39:
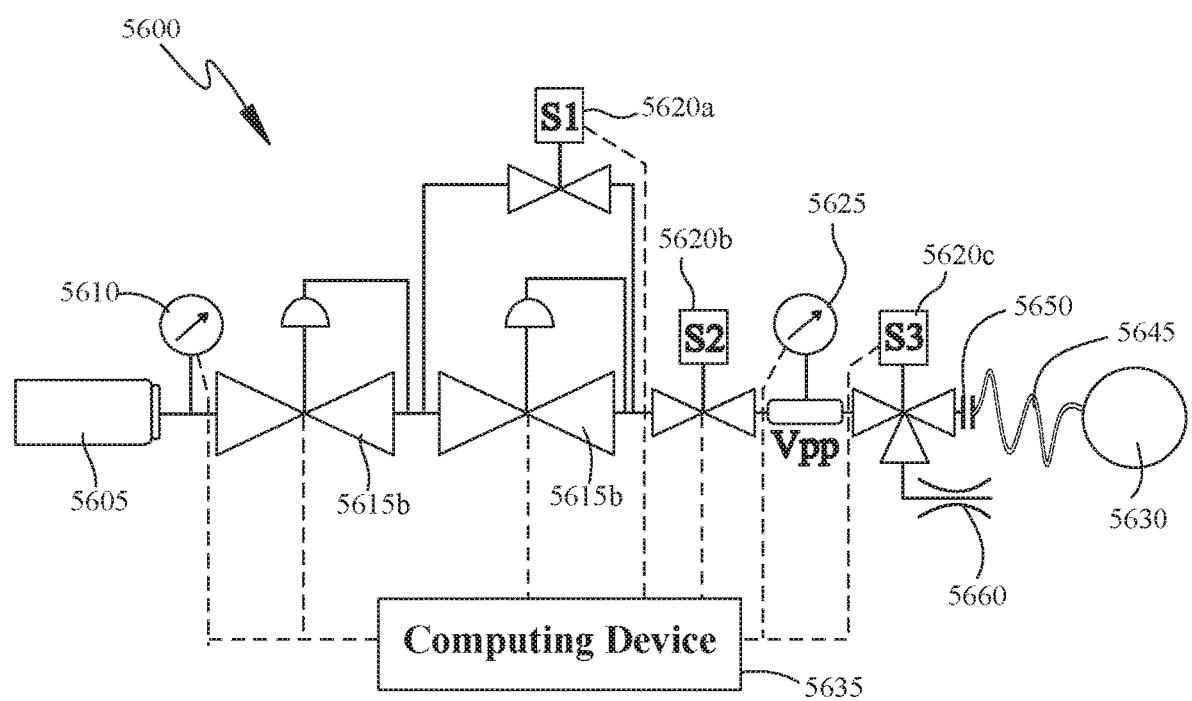
FIG. 39 is a schematic of the components of a Dispenser 5600 in an embodiment.
Figure 40:
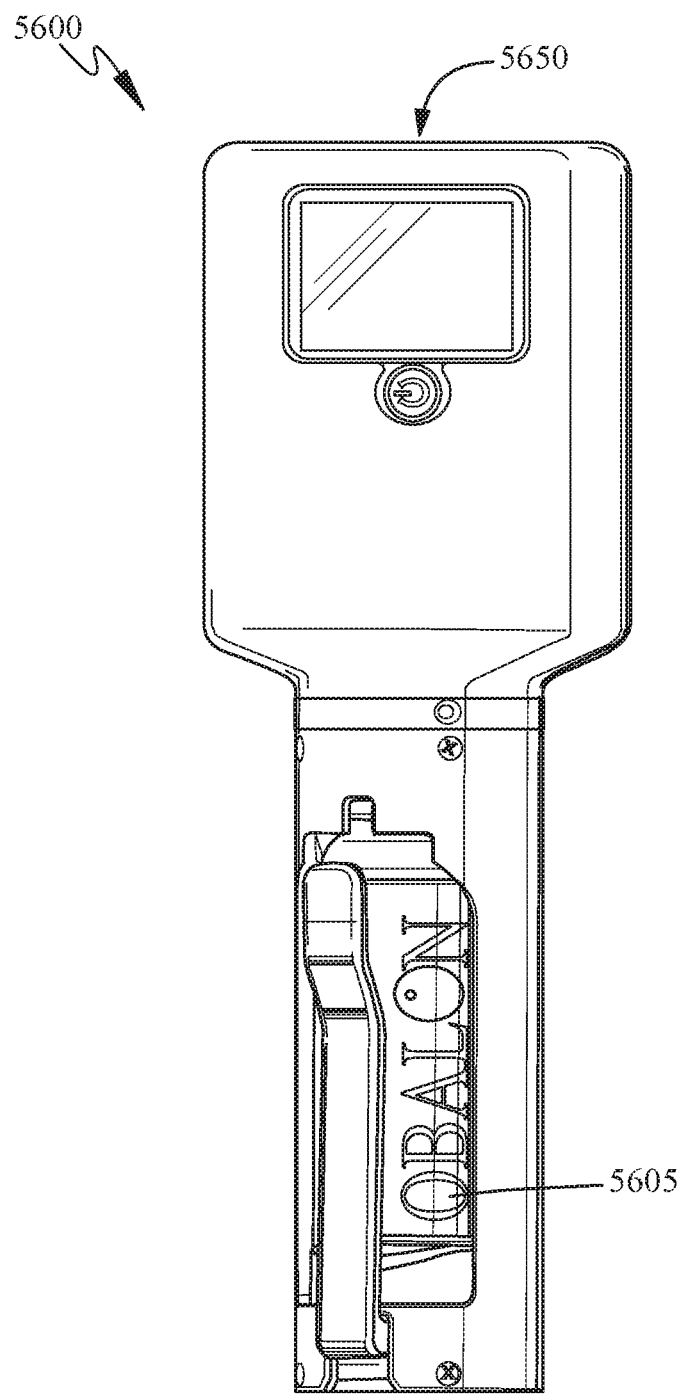
FIG. 40 is a top view of the Dispenser 5600 of FIG. 39.
Figure 41:
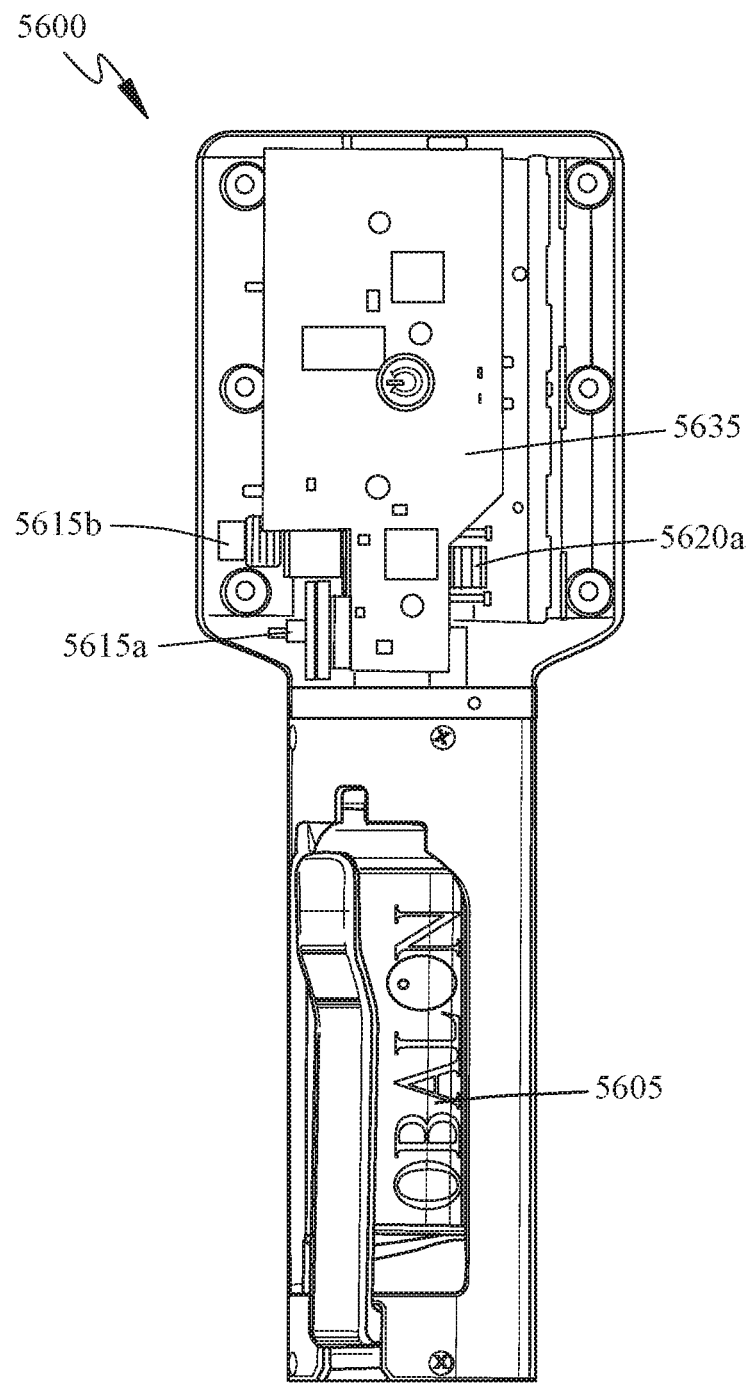
FIG. 41 is a top view of the Dispenser 5600 of FIG. 39, with the top shroud removed.

FIG. 39 is a schematic of the Touch Dispenser 5600. In the illustrated embodiment, the Dispenser 5600 comprises seven (7) primary components to control the flow of gas and detect inflation in constrained spaces; two (2) pressure regulators (5615a, 5615b), two (2) gauge pressure sensors (5610, 5625), and three (3) solenoid valves (5620a, 5620b, 5620c). These components operate in concert to safely inflate the Balloon 5630 to the proper pressure while preventing inflation within constrained spaces.

The pressure sensors provide feedback to the software device for control of the solenoid valves. The first or Proximal Pressure Sensor 5610 measures gas pressure in the can 5605. The Pressure Regulators (5615a, 5615b) restrict the flow of gas from the Inflation Can 5605 such that pressure flow is limited in case of esophageal or hiatal hernia placement. The High-Pressure Regulator 5625a regulates pressure for the pre-pulse phase of the balloon fill procedure as well as providing controlled pressure to the Low-Pressure Regulator 5615b during the fill phase of the procedure. The Low-Pressure Regulator 5615b keeps the pressure at the second pressure sensor 5625 below a value that would cause harm to the patient, if the system attempted to fill the balloon while in a constrained space, such as the esophagus.

The High-Pressure Bypass Valve 5620a is under control of the computing device 5635 and enables the Dispenser 5600 to pressurize the pre-pulse volume Vpp. The High-Pressure Bypass Valve 5620a is only open during pre-pulse. Opening of the High-Pressure Bypass Valve 5620a will enable a pre-pulse of the gas mixture to flow at the required pressure and volume to confirm proper balloon placement (e.g., the balloon is not constrained in the patient's esophagus) and to facilitate the opening of the balloon after the capsule has softened and at least partially dissolved in the patient's stomach. Closure of the High-Pressure Bypass Valve 5620a enables use of another solenoid control valve (e.g., a Proximal or Control Valve 5620b). The Control Valve 5620b both captures the pre-pulse volume Vpp and controls gas flow during balloon inflation or filling. When the volume Vpp is charged with high pressure gas, the Control Valve 5620b is closed to capture the pre-pulse volume Vpp. During balloon inflation, the Control Valve 5620b is open to the balloon 5630 and the Control Valve 5620b dispenses controlled pulses of gas to the balloon 5630. The second or Distal Pressure Sensor 5625 measures pressure downstream of the pressure regulators and provides a feedback signal to the Computing Device 5635 for controlling the amount of gas that is dispensed to fill that balloon 5630, thereby ensuring accurate balloon inflation. A distal 3-Way Valve 5620c is used both to fill the balloon 5630 and to vent balloon pressure. When the 3-Way Valve 5620c is opened to the balloon 5630, the gas can flow from the pre-pulse volume Vpp and into the balloon 5630. When the 3-Way Valve 5620c is opened to the Exhaust Orifice 5660, gas can flow from the balloon 5630 through the Exhaust to the atmosphere, thereby reducing pressure within the balloon. When both Control Valve 5620b and the 3-Way Valve 5620c are closed, the system 5635 is able to determine if the Low-Pressure Regulator 5615b is functioning properly by measuring pressure with the Distal Pressure Sensor 5625. If the High-Pressure Bypass Valve 5620a is also closed, (e.g., all three valves are closed), the functionality of the High-Pressure Regulator 5615a can be determined by measuring pressure with the Distal Pressure Sensor 5625. In addition, the Dispenser 5600 has an Atmospheric Pressure Sensor (not shown) which is used as an indirect measurement of elevation, the information from which is used by the computing device 5635 to ensure the Dispenser 5600 inflates the balloon 5630 to an internal pressure required at the altitude at which the procedure is being performed.

The Touch Dispenser 5600 is a durable, re-usable device that may be used for up to 5,000 cycles. The Inflation Can is a single-use device and must be disposed of after use. In preferred embodiments, the dispenser includes three solenoid valves, which are configured for use with gas and have an operational pressure range which includes 1 to 207 kPa, and to control balloon inflation without leaking. Dispenser precisely displays pressure using a digital pressure sensor with 0.1 kPa resolution. The dispenser is configured to step down the can pressure to a range that is capable of detecting when the balloon is in a constrained state during pre-pulse. To do this, the dispenser includes a pressure regulator that is not user adjustable and reduces the can pressure to 155±25 kPa. The Dispenser is configured to limit the pressure during the balloon inflation process to below 70 kPa. In preferred embodiments, Dispenser and Inflation Can are configured to fill balloon to within ±0.5 kPa of the desired set pressure within the range of 8.3-17.2 kPa over the altitude range of 0-8000 ft (0-2438 m). In some embodiments, the Dispenser is configured to perform at least 5000 procedure cycles, and to hold pressure and function as intended. The Dynamic components, e.g., the actuator lever 5640, of Touch Dispenser can cycle through intended range of motion with Inflation can inserted into the can receiving space 5642. The Dispenser is configured to open Inflation can valve when actuator lever is closed. Touch Dispenser is configured to dispense the contents of Inflation Can to support total system procedure time goal of 10 minutes. For example, in some embodiments, the fully pressurized Dispenser and Inflation Can inflates Balloon in about 4 to 6 minutes. Touch Dispenser is configured to provide advance notification of low battery level. Touch Dispenser contains a low battery alert which will allow at least 10 procedures of additional use. Touch Dispenser is configured to have a battery life that is useful for a reasonable amount of balloon deployments. Battery life is rated at least 100 procedures with standard AA batteries that are replaceable in the field as needed. Touch Dispenser shall preserve battery when not in use. In some embodiments, Touch Dispenser is configured to automatically shut off 40 minutes or less from last user input.

In some embodiments, the Touch Dispenser is configured to seal to Inflation Can in such a way to prevent leaks. Accordingly, in some embodiments, the Inflation Can engaged in the Touch Dispenser does not leak more than 0.7 kPa over 5 minutes from a starting pressure of 413±7 kPa. The dispenser is configured to be reliable. Accordingly, the dispenser is configured to regulate the output pressure to 130-180 kPa (18.6-26.1 psi) for pre-pulse, and to regulate the output pressure to 43-53 kPa (6.2-7.7 psi) for balloon fill. In some embodiments, the Dispenser is configured to safely release balloon pressure. For example, the Dispenser is configured to vent the pressure in a balloon pre-pulsed in a simulated esophagus to below 7.0 kPa. Additionally, the flow of gas during pressure release is directed inside of protective shrouds of the dispenser. The Dispenser pressure sensors are configured to maintain accuracy during a low power condition. For example, the Dispenser pressure sensors are configured to maintain accuracy as described elsewhere herein if low battery condition is present.

In preferred embodiments, the Dispenser comprises pressure gauges with adequate accuracy to ensure final balloon pressure is attained. For example, in some embodiments, the Dispenser includes a balloon pressure gauge (distal sensor)

with accuracy of ±0.8 kPa (0.4%) over 0 to 207 kPa. In a further example, the Dispenser includes a can pressure gauge (proximal sensor) with accuracy of ±1.6 kPa (0.4%) over 0 to 414 kPa. In another further example, the final inflation pressure range of the Touch Dispenser does not exceed 9.5-13 kPa so as to ensure that the final pressure balloon will not exceed 8.3-17.2 kPa.

In preferred embodiments, the Touch Dispenser comprises one, two or more pressure gauges that maintain accuracy over the dispenser's useful life. For example, the Dispenser's balloon pressure gauge is configured to have an accuracy of ±0.8 kPa over 0 to 207 kPa after 5000 cycles of 0 kPa to 207 kPa. In another example, the can pressure gauge is configured to have an accuracy of ±1.6 kPa over 0 to 414 kPa after 5000 cycles of 0 kPa to 414 kPa.

In preferred embodiments, the Dispenser and Inflation Can are configured to operate normally in the temperature range of 15° C. to 25° C. and 30-85% relative humidity (i.e., RH). Further, the Dispenser may be configured to withstand storage conditions of 0° C. to 40° C., and 30% to 85% RH, and 0-3000 meters elevation.

The Obalon Touch Balloon System (the "System") is designed to assist weight loss by partially filling the stomach, so as to provide the patient with a feeling of fullness. The system consists of up to 3 intragastric balloons placed during a 6-month period. In some embodiments, up to three balloons may be placed in the patient's stomach 20 for a period of 8 months, 9, months, 10, months, 11 months, 12 months or longer. The balloons are swallowable by the patient using normal peristalsis, or peristaltic waves, in that the balloons are delivered via capsule. Each balloon is placed individually within the first 3 months. All 3 balloons are removed at the end of the treatment period. For example, in the case of a 6-month treatment period, all three balloons are removed from the patient's stomach 20 six months after the first balloon was placed (i.e., swallowed by the patient and then inflated).

For administration, a balloon and catheter assembly is used, such as described elsewhere herein. In some embodiments, each balloon is contained within a USP grade hydroxypropyl methylcellulose (HPMC) capsule, which is attached to the catheter. When it is swallowed by the patient, the balloon capsule delivers the balloon in a similar manner that a medicinal capsule delivers pharmaceuticals, via peristalsis. The catheter comes pre-attached to the compacted balloon's radiopaque, self-sealing valve, as described elsewhere herein.

The administration (placement) procedure requires no sedation. The capsule and a portion of the attached capsule are swallowed by the patient. The catheter is then attached to the Obalon Touch Dispenser, which contains an engaged Obalon Touch Can (a can containing nitrogen-sulfur hexafluoride gas mixture) to fill the balloon. After the patient swallows the balloon capsule, radiography is performed prior to inflation, to ensure that the balloon is in the patient's stomach 20 (e.g., visualized by the radiopaque marker). The preferred radiographic method is fluoroscopy or digital radiography since both provide real-time image of the balloon using low levels of radiation with immediate imaging feedback. Once there is radiographic confirmation that the balloon (e.g., the radiopaque marker associated with the self-sealing valve) is below the gastroesophageal junction, and therefore not constrained in the patient's esophagus, then the balloon is inflated.

In some embodiments, a fully inflated single balloon is an ellipsoid, a spheroid or an oblate spheroid with a volume of approximately 250 cc. When 3 balloons are placed in the patient's stomach, the total balloon volume is approximately 750 cc. However, it is foreseen that the balloon could include larger or smaller volumes. For example, balloons for use with teenagers, or smaller people, can be configured with a volume of less than 250 cc, such as but not limited to approximately 100 cc, approximately 125 cc, approximately 150 cc, approximately 175 cc, approximately 200 cc, and approximately 225 cc. In another example, the balloon is configured with a volume greater than 250 cc, such as but not limited to approximately 275 cc, approximately 300 cc, approximately 325 cc, approximately 350 cc, approximately 375 cc and approximately 400 cc. In still another example, the patient may receive only two balloons or as many as four balloons.

After inflation is complete, the catheter is ejected from the balloon valve and retrieved, leaving each balloon free-floating in the patient's stomach.

Balloon use may require the concurrent use of proton pump inhibitors for the duration of implantation. For example, clinical studies have shown that use of 40 mg/day of omeprazole or an equivalent dosage of similar medications is required over the duration of use. Some patients may require an anti-emetic and anti-spasmodic medication at least 24 hours prior to administration and such medications may be prescribed in conjunction with balloon use for up to 5 days beyond balloon administration. In preferred embodiments, Pre-existing GI pathology is ruled out prior to placement of any balloons by conducting a comprehensive medical history and an upper endoscopy (e.g., and upper GI) to determine a patient's suitability for the procedure and to ensure the patient is not contraindicated for device use.

The inflation system is prepared prior to balloon administration. The dispenser is first powered on, and then the dispenser lever is lifted and the can is inserted into the shuttle. The lever on the dispenser is closed to actuate the can valve and pressurize the system. The system performs a series of electrical and pressure tests to ensure that the inflation system is working properly. Once these tests are complete, the dispenser displays a screen to indicate that the system is ready for use. Throughout the procedure, the dispenser screen displays pressure readings, images, and touchscreen buttons to provide information and control to the user.

After the balloon capsule is swallowed, the balloon catheter is attached to the Touch Inflation System. All entries and exits within the dispenser and catheter connections are sealed and it is imperative that the catheter connection is fully secured during the procedure to maintain a closed gas pathway between the can and balloon.

In some embodiments, the automated inflation systems described herein can be incorporated into a dispenser, such as the dispenser described with respect to FIGS. 39-47.

EXAMPLES

Example 1

Figure 47:
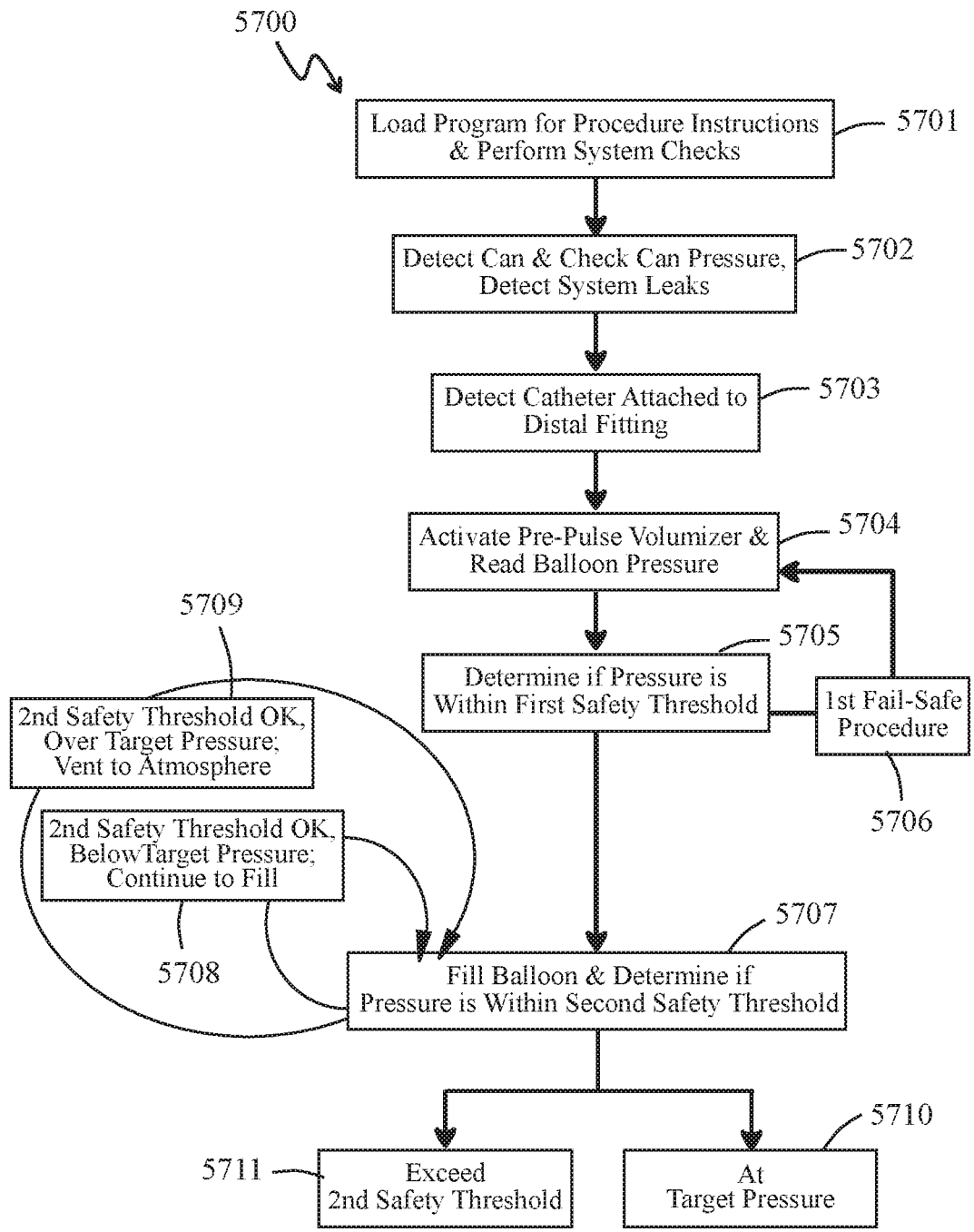
FIG. 47 is a flow chart 5700 illustrating steps in using the dispenser 5600 of FIG. 39 to inflate an inflatable intragastric device.

FIG. 47 illustrates an exemplary 5700 by which the Touch Dispenser 5600 5200 may operate with the intragastric device system. Initially, a program is loaded 5701 onto the dispenser 5600, specifically the circuit element 5635 which may include processors and memory units. The program loaded onto the Dispenser 5600 may be one of a plurality of programs tailored for a specific application, or may be a single program with adjustable features that allow the operator of the Dispenser 5600 to calibrate according to a particular situation or need. The program may provide a set of directions in a visual format on the display screen, or may provide an audio set of directions. The Dispenser 5600 may calibrate the dispenser and peripheral objects to normalize the sensed pressure of the intragastric balloon and the sensed pressure of the catheter 5645 and the pre-pulse volume Vpp to the surrounding atmospheric pressure. This allows for use of the Dispenser 5600 in location of varying elevations.

Further to FIG. 47, the Dispenser 5600 may detect 5702 the presence of the canister 5605. The Dispenser 5600 may also detect 5503 connection of the self-sealing valve of a catheter 5645 to the dispenser distal fitting 5650. The distal fitting 5660 may further comprise an electromechanical means for alerting the system to when a catheter 5645 is connected to the fitting, or when there is no distal connection.

Further to FIG. 47, the Dispenser 5600 may activate 5704 a pre-pulse volumizer. In one example embodiment, the dispenser 5200 may release a configurable volume and pressure from the pre-pulse volume Vpp into the intragastric balloon 5630. The Dispenser 5600 then determines 5705 if the balloon pressure is within a first safety threshold. If the dispenser determines that the balloon pressure is not within the first safety threshold, then the device determines that the balloon is constrained in a space such as the esophagus. In the event that the balloon is determined to be constrained in the esophagus, then the physician may be directed 5706 to perform a Fail-Safe Procedure that may move the constrained balloon from the constrained space and into the stomach. A Fail-Safe Procedure may include venting a portion of the gas within the balloon, either via the Exhaust 5650 or via disconnecting the catheter 5645 from the fitting 5650 and using a syringe attached to the catheter 5645 to withdraw the gas within the balloon 5635. The Fail-Safe Procedure may also include encouraging the patient to drink water or swallow a small amount of soft food to push the balloon 5635 out of the esophagus and into the stomach. Once the Fail-Safe Procedure has been performed, the Balloon administration procedure may be restarted by returning to step 5704. In some embodiments, the Fail-Safe Procedure 5706 may be repeated two or more times. If the patient fails to swallow the balloon (e.g., move the balloon from the confined space of the esophagus and into the stomach), then the Device 5700 may direct the balloon to be removed, such as via endoscopy.

When the balloon pressure passes the first safety threshold 5705, the system begins filling the balloon 5635. To fill the balloon, the system releases small volumes of gas, such as an amount of gas equal to the Vpp, into the balloon. When an amount of gas is released into the balloon, the system may determine 5707 if the balloon pressure passes a second safety threshold and/or if the balloon pressure has reached a final target balloon pressure. If the balloon pressure is within the second safety threshold but below the target pressure (e.g., step 5708), then the system may deliver another small volume of gas (e.g., Vpp) to the balloon. If the balloon pressure is within the second safety threshold but above the target pressure (e.g., step 5709), then the system may open the Exhaust 5660, to allow a small volume of gas to bleed from or flow out of the balloon. Steps 5708 and 5709 may be repeated iteratively, until the balloon pressure equals the target pressure 5710. Once the balloon pressure is stabilized at the target pressure 5710, the catheter 5645 may be ejected from the balloon 5630 and removed from the patient, such as described elsewhere herein. Once the catheter 5644 has been removed, the patient may be free to go home. However, if the balloon pressure fails the second safety threshold 5711, then the balloon 5635 may be constrained within a second constrained space, such as a hiatal hernia. In certain embodiments, the physician may perform a second fail-Safe procedure to move the balloon 5635 from the second constrained space into the stomach, and then continue with the balloon administration procedure. In other embodiments, the system may terminate the balloon administration procedure, and optionally direct the physician to remove the balloon endoscopically.

Example 2

The Touch Dispenser 5600 was used in an animal model to demonstrate that the Dispenser 5600 is capable of detecting when the Obalon balloon is in an anatomically confined space during the pre-pulse and balloon inflation phases of the balloon administration procedure. Pre-pulse is a means of detection to determine if the balloon has passed safely from the patient's esophagus into the stomach. During pre-pulse, a small volume Vpp within the Dispenser 5600 is filled to a higher pressure than the pressure that used for balloon inflation. This higher pressure is limited to between 130-180 kPa as flow from the inflation can is directed through a High-Pressure Regulator to step the pressure down from the pressure within the Can 5605. This high pressure volume (e.g., Vpp) is then isolated from the can and delivered to the balloon 5630 through the catheter 5645. The pressure detected by the Distal Pressure Sensor 5625 remains high while the balloon 5630 is still inside of the capsule. As the capsule material disintegrates, the balloon begins to unfold, which the system detects as a decrease in balloon pressure.

The Dispenser waits until the pressure is below 60 kPa and determines the balloon's location based upon the balloon's pressure value and the rate of pressure decay. If the pressure is less than 60 but greater than 17.2 kPa and the rate of pressure decrease is less than 0.2 kpa/s, then first safety threshold has been exceeded, the dispenser will provide indicia to the physician that the balloon is within a constrained space, such as within the esophagus. If the pressure continues to decrease at a high rate to below 17.2 kPa, the system with evaluate the rate of change for a rate of change that is less than 0.2 kPa in 3 seconds before alerting the user of an esophageal placement. If the pressure decreases to below 7 kPa, the first safety threshold has been passed, and the balloon is unconstrained. Whenever a constrained state is detected the dispenser will exhaust the pressure to below 7 kPa, so as to relieve pressure on the anatomical space.

After a successful pre-pulse, the dispenser will continue sensing for a constrained balloon during the fill portion of the procedure by looking for a pressure that is greater than 11 kPa during the first balloon fill phase. If the dispenser senses a high pressure, it will alert the user via suitable indicia, such as but not limited to a sound and an image on the dispenser's touch screen. The dispenser or instructions for use may instruct the user how to proceed (e.g., removing gas from the balloon and drinking water) and provide a chance to continue the balloon administration procedure. If it detects another high pressure, it will alert the user. The dispenser may allow three attempts to clear a constrained fill situation before a final error is shown, which terminate the balloon administration procedure.

To evaluate severity of esophageal injury when a balloon was constrained in the esophagus, while inflating the balloon with the Touch Dispenser, esophageal inflations were evaluated in three animals. Each animal was used for three balloons that were partially inflated in three locations in the esophagus, at locations that were 10 cm apart. For each partial deployment, pre-pulse and three confined pressure scenarios were performed. A dispenser was prepared. To create the, a balloon was placed in the animal's esophagus via endoscopy. The catheter was attached to the Touch Dispenser and a pre-pulse gas was delivered to each balloon. The initial balloon pressure was high, about 130 kPa. The pressure began to decrease and the balloon was observed to inflate. The balloon pressure stabilized between 30-45 kPa. The Touch Dispenser provided indicia that the balloon was constrained and exhausted an amount of gas from the balloon, such that the balloon was observed to deflate. After the initial partial deflation, the administration procedure was continued without moving the balloon. When the balloon continued to inflate, the constrained balloon indicium was again provided. Again, the dispenser allowed the balloon to deflate. This was done two additional times before the dispenser displayed the final warning and required the user to turn off the dispenser. The balloon was then manually deflated with a 60 cc syringe and removed from the animal's esophagus. This was done in two other locations for a total of three balloon deployments in each animal.

No redness or trauma was observed endoscopically after the esophageal testing. One animal was sacrificed and the esophagus examined at necropsy. No damage was observed. Tissue was sent for histological evaluation and nothing of concern was noted. The other two animals were survived and will be sacrificed at 30 days and the esophagus will be examined at necropsy.

Example 3

A Nitrogen Fill System and disposable Procedure Canister devices are provided as accessories to the Obalon Gastric Balloon (OGB). In use, the cap is removed from the valve of a disposable Procedure Canister. This disposable Procedure Canister is inserted into a Procedure Canister and the lever is closed to engage the valve on the disposable canister. A lack of a fluid path of a lower pressure gradient keeps the fluid from expelling. The Nitrogen Fill System is attached to an Accessory Kit via a luer fitting. A 3-port, 2-position valve on the Accessory Kit is confirmed closed before opening the 90° valve. Appropriate pressure is confirmed via the digital gauge, then a standard OGB System inflation procedure commences and the fluid path is opened to the balloon in the body. After the procedure, the disposable Procedure Canister is removed from Nitrogen Fill System and properly disposed of. The Nitrogen Fill System is re-used and can have a useful life, e.g., of at least 1 year.

The Procedure Canister is an appropriate size to fit into the Nitrogen Fill System, e.g., a major outer diameter of the non-valved canister is 45±1 mm. The Procedure Canister is an appropriate size to fit into the Nitrogen Fill System, e.g., a height of the non-valved canister is 115±1 mm. The Procedure Canister is pressure resistant, e.g., having an 18-bar pressure resistance. The internal volume of the Procedure Canister is adequate to fill a Balloon Kit at appropriate fill pressure, e.g., a brimful volume of non-valved canister is 161±3 cm3. The Procedure Canister is accurately pressurized, e.g., sampling direct pressure measurements are within ±1 psi or ±7 kPa. The assembled Procedure Canister is bubble tight, e.g., pressurized disposable canisters are tested visually for leaks via a water bath bubble detection test. A volume of the canister allows for enough air at a pressure that is not great enough to rupture the catheter, e.g., a pressure of fully pressurized canister is not to exceed 75 psi. The Nitrogen Fill System has the ability to connect to the Balloon Kit. The Nitrogen Fill System contains a luer fitting that connects to a swallow catheter. The Nitrogen Fill System has an effective valve for inflation.

The Nitrogen Fill System has a ¼ turn valve. The valve is designed for gas and has an operational pressure range which includes 1 to 75 psi. The Nitrogen Fill System precisely displays pressure. The Nitrogen Fill System contains a digital gauge with 0.01 psi resolution or 0.1 KPA resolution. The Pressurized Nitrogen Fill System is bubble tight, e.g., no bubbles per bubble leak test in 130° F. water bath for 1.5 minutes. The Nitrogen Fill System fills the balloon to proper pressure, e.g., 2.0+/−0.5 psi at sea level. The pressure is retained by the assembled Nitrogen Fill System effectively enough to not place balloon fill pressures outside of specification. The mass of contained gas is not to drop more than <5 psi over the course of 1 year. The Nitrogen Fill System is reliable for at least 1 year, and the Nitrogen Fill System is good for at least 1000 actuation cycles. The Procedure Canister is compatible with the Nitrogen Fill System. The Dynamic components of the Nitrogen Fill System can cycle through intended range of motion with the disposable canister inserted.

The Nitrogen Fill System opens the disposable dispenser valve when the receiver is closed. The Nitrogen Fill System is capable of dispensing contents of the canister to support a total system procedure time goal of 5-10 minutes. The fully pressurized canister can be dispensed within 30 seconds. The Nitrogen Fill System's digital gauge provides advance notification of a low battery level. The digital gauge contains a low battery indicator. Nitrogen Fill System's digital gauge battery life shall be useful for the service life of the device. The digital gauge battery life is rated at least 2000 hours. The batteries are standard and replaceable in the field as needed. The digital gauge preserves the battery when not in use, e.g., by automatically shutting off 60 minutes from last button press. The Nitrogen Fill System seals to the canister in such a way to prevent leaks. The canister engaged in the Nitrogen Fill System does not leak more than 0.1 psi over 5 minutes. The Nitrogen Fill System's Digital Pressure Gauge is electromagnetically compatible. The Nitrogen Fill System's gauge readings are easy to read, e.g., the gauge size is at least 3" diameter with a digital display. The Nitrogen Fill System's pressure gauge is intuitive to operate, e.g., the gauge has one touch on and off button that is clearly labeled. The actuator on Nitrogen Fill System for inflation of the balloon is intuitive, e.g., a colored valve lever with only on and off positions is used for initial balloon fill from the Nitrogen Fill System. The Nitrogen Fill System is easily inserted into the Nitrogen Fill System, e.g., the Nitrogen Fill System opening is large and obviously apparent.

The mass of nitrogen contained by Procedure Canister is appropriate to attain a desired final balloon pressure, e.g., the canister sample is weighed before and after filling to assure 0.52±0.01 grams of gas. The Nitrogen Fill System has a digital gauge with adequate accuracy to ensure final balloon pressure is attained, e.g., the Nitrogen Fill System's digital gauge has an accuracy of 0.25% of Full Scale. The Nitrogen Fill System has a digital gauge that maintains accuracy over its useful life, e.g., the Nitrogen Fill System's digital gauge has an accuracy of 0.25% of Full Scale after 1000 cycles of 0 psi to 30 psi or 0 KPa to 26 kPa. The Nitrogen Fill System is preferably operated under reasonable environmental conditions, e.g., temperatures of from −18° C. to 55° C. and relative humidity of from 30% to 85%. The altitude classification system is used in altitude of a <2000 m (61 to 101 kPa).

The Obalon Gastric Balloon System (the "System" or OGB) is designed to assist weight loss by partially filling the stomach 20 and inducing satiety. The System consists of up to 3 intragastric balloons that are placed non-invasively in the stomach 20 (via a catheter-capsule assembly) and reside in the stomach 20 for up to 3 months (12 weeks). For administration, each balloon is contained within a medical-grade porcine gelatin capsule, which is attached to a miniature catheter. The balloon capsule delivers the balloon in the same manner that a medicinal capsule delivers pharmaceuticals. The catheter comes pre-attached to the compacted Balloon's radio-opaque, re-sealing valve. For administration of the device (placement), the catheter/capsule is swallowed by the patient. The catheter is then attached to a Procedure Canister that contains a disposable Nitrogen Fill System that is used to fill the balloon. After the patient swallows the balloon capsule, radiography is done to ensure the balloon is in the stomach 20 after swallow (visualized by the radio-opaque marker). The preferred radiographic method is fluoroscopy since it provides a real-time picture of the balloon using low levels of radiation. A fully inflated single balloon is an ellipsoid with a volume of approximately 250 cc. When 3 balloons are placed, the total balloon volume is 750 cc. The administration procedure requires no sedation. After inflation is complete, the catheter is manually ejected from the balloon valve and retrieved by the physician; leaving the balloon free-floating in the patient's stomach 20 for up to 3 months.

Balloon use can employ the concurrent use of Proton Pump Inhibitors for the duration of use, e.g., 40 mg/day of pantoprazol or an equivalent dosage of similar medications. It is likely an effective treatment for undiagnosed pre-existing esophagitis and gastritis which should enhance tolerability of the devices in residence. Antiemetic and spasmolytic agents can be given immediately following balloon placement and given as needed while the balloon(s) are in the stomach.

Clinical trials have shown that it is preferred to place one balloon initially and subsequent balloons be placed later in the 3-month period (FIG. 1). Determination of whether a patient requires additional volume should be made based on patient weight loss progress and reported satiety levels. Additional balloons are placed in the same manner as the first balloon placement; requiring only radiography for placement.

The balloon helps the patient eat less food at each sitting. The selection of less calorie dense foods in addition to the balloon(s) will only help facilitate weight loss. The balloons are intended to remain in the stomach 20 for 3 months (12 weeks) from the time of placement of the first balloon. All balloons placed are removed at the end of three months using standard endoscopic methods. The device(s) are removed by a trained healthcare professional proficient in gastroscopy.

The health care setting in which the device is to be used has access to fluoroscopy or digital x-ray at the time the device is administered, to ascertain the balloon/capsule placement in the stomach 20 prior to inflation. In addition, the prescribing physician has immediate access to an endoscopy unit and to personnel proficient in gastroscopy and foreign object retrieval should problems arise during administration. Gastroscopy equipment and persons trained in foreign object retrieval are employed for device removal.

The Obalon Gastric Balloon System (the "System") is indicated for temporary use for weight loss in overweight and obese adults with a BMI of 27 or greater who have previously failed a supervised weight control program. The Obalon Gastric Balloon system is intended to be used in conjunction with a diet and behavior modification program.

Up to 3 Obalon Gastric Balloons may be placed in the stomach 20 across a 3-month (12-week) period based on the individual's weight loss progress and satiety levels. The maximum placement period for the Obalon Gastric Balloon(s) is 3 months (12-weeks) and all balloons must be removed at that time or earlier.

All components are supplied non-sterile. The System can include the following: a Placebo Capsule Assembly including a capsule of the same material, size, shape and weight as the actual device but that does not contain a balloon or catheter. The capsule is filled with food-grade sugar to simulate device weight; an Obalon Gastric Balloon Assembly including one folded balloon contained in a swallowable Gelatin Capsule and attached to 1 disposable, flexible Catheter Delivery System; an Accessory Kit including two 3 $cm^3$ Syringes, an extension tube and stopcock with a 3-way valve, and a 60 $cm^3$ syringe; a Procedure Canister which is a reusable component and is used in conjunction with the disposable Nitrogen Fill System with the Digital Pressure Gauge attached; two AAA Batteries; and a Nitrogen Fill System filled with 150 cm3 of nitrogen. Other items that can be used in conjunction with administering and/or removing the System include a small clean bowl, bottled water, timer/clock, digital X-Ray or fluoroscope, vacuum aspiration source, gastroscope, gastroscope Injection Needle (minimum length can be 6 mm and minimum needle gauge size can be 23) compatible with the working channel of the gastroscope, and a rat tooth with alligator jaws grasping forceps (minimum opening width can be 15 mm) or other commercially available endoscopy retrieval tools such as two-prong graspers, compatible with the working channel of the gastroscope.

Figure 43:
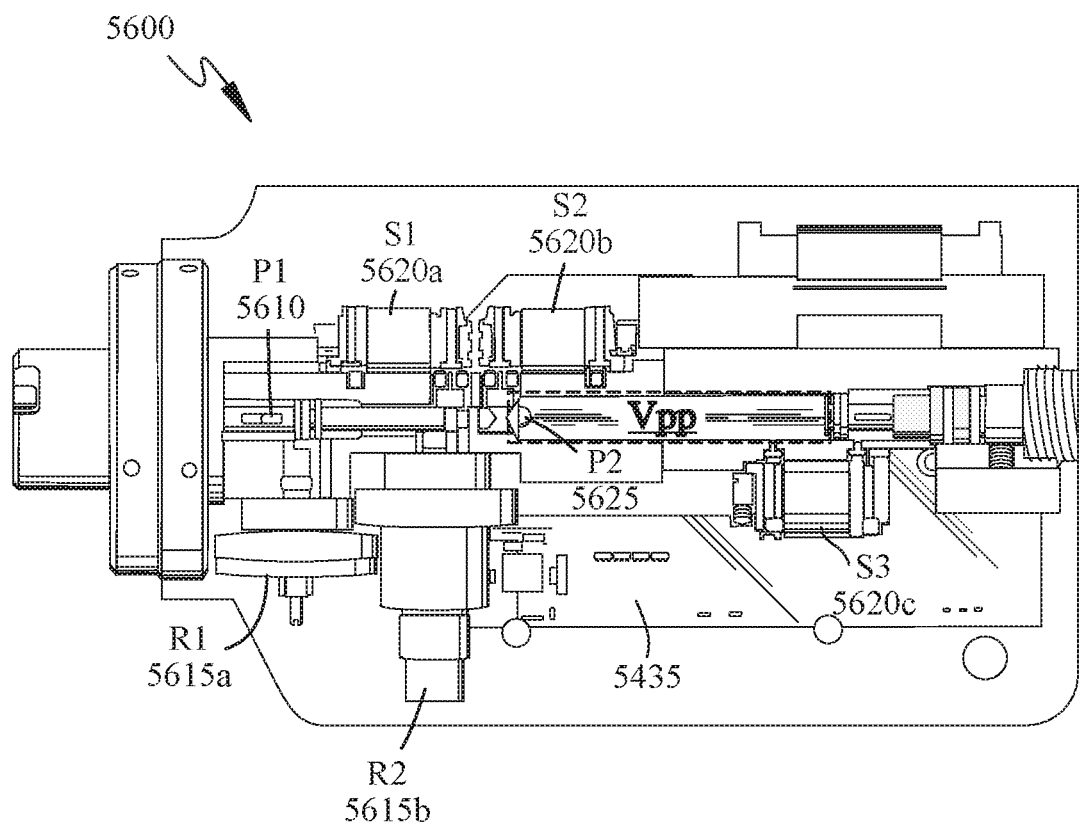
FIG. 43 is a schematic of the Dispenser 5600 of FIG. 39, illustrating the positions of various components.
Figure 44:
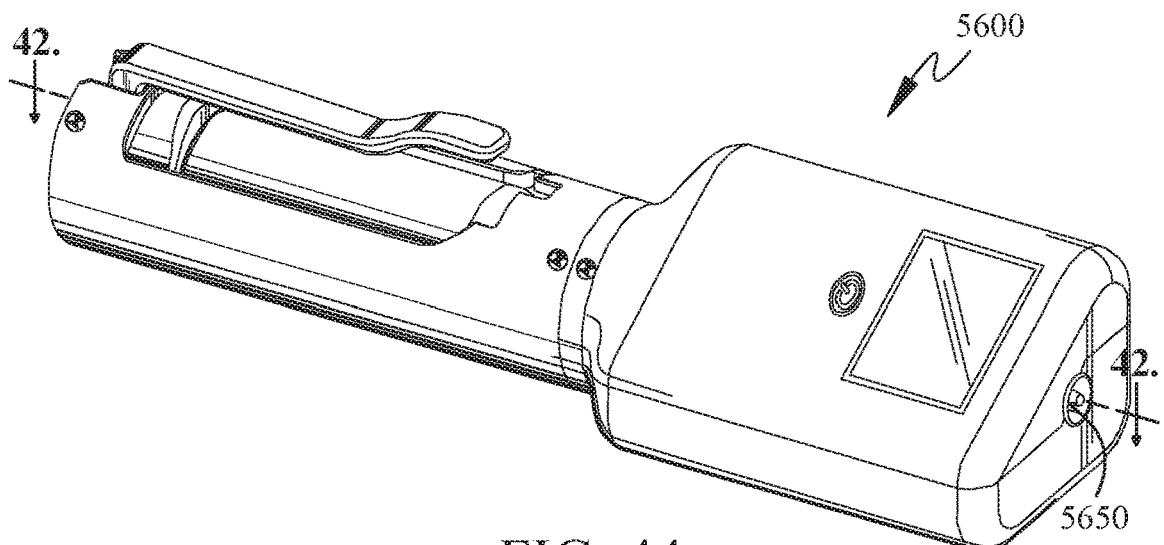
FIG. 44 is a top perspective view of the Dispenser 5600 of FIG. 39.
Figure 45:
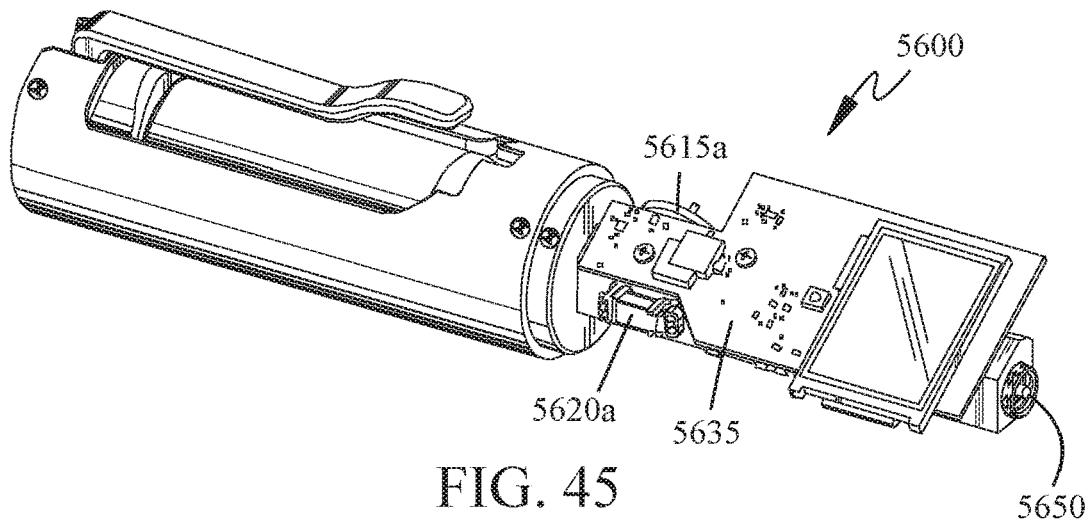
FIG. 45 is a front perspective view of the Dispenser 5600 of FIG. 29 with the shroud removed to show portions of the computer system 5635.
Figure 46:
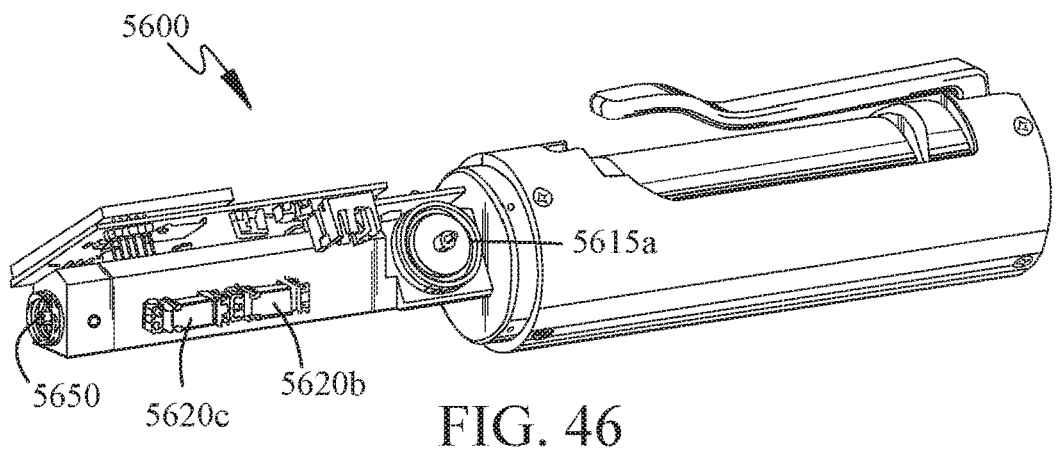
FIG. 46 is a rear perspective view of the Dispenser 5600 of FIG. 39.

The Nitrogen Fill System ("Dispenser") is prepared for use by first ensuring that the Dispenser is correct for the altitude of the facility or contains a barometric pressure compensation valve to adjust the starting pressure to ensure proper balloon end pressure. Failure to use the correct Dispenser can result in a deflated or over inflated balloon. The Dispenser valve is in the open position. The "ON" button is pressed to turn on the Dispenser Gauge. The extension tube and stopcock with 3-way valve is removed from the Accessory Kit packaging. The luer lock plug is removed from the end of the Dispenser. The luer lock plug is saved and put back on the Dispenser after the procedure is complete to keep the Dispenser free of debris. The proximal end of the luer connector of the extension tube (from the Accessory Kit) is connected to the Dispenser with valve open. The stop cock valve is in the closed position to stop the flow of gas. The cap is removed from the Disposable Canister. The canister is configured to not fit into the Dispenser if this cap is not removed. With the lever in the 'open' position, the disposable canister is inserted straight down into the Dispenser. The lever is set to the 'closed' position to secure the disposable canister in place. The initial reading on the gauge is confirmed to be between 257 kPa and 297 kPa, to ensure proper balloon inflation. The valve on the Dispenser is closed by rotating the valve clockwise (to the right) (FIG. 43). The Dispenser valve is in the closed position before proceeding to next steps to ensure the proper positioning and status of the balloon capsule prior to proceeding to the balloon fill step. The 3 $cm^3$ syringe is removed from its packaging and filled with 1.5 ml of room temperature water and set aside. A small clean bowl half-way with water. The Obalon Gastric Balloon Capsule and Catheter Delivery System are removed from their packaging.

Prior to the patient swallowing the functioning device, it is recommended that they first swallow the placebo capsule.

The purpose of this procedure is to determine which patients will and will not be good candidates to have the actual device placed. The placebo capsule should go down easily. If the patient swallows the placebo capsule without problem, it is recommended that they proceed with the Balloon therapy.

The Obalon Balloon capsule is administered to the patient using a normal pill swallowing method. Endoscopy is not required for placement. Fluoroscopy (or digital x-ray) is employed during the placement procedure to verify placement of the balloon in the stomach 20 prior to inflation of the device. Any existing balloons are also imaged to confirm their integrity prior to swallowing another capsule. The total placement time is less than 15 minutes for each balloon placed.

Should a patient have a strong gag reflex; a topical anesthetic may be applied immediately before capsule administration. To place the balloon, it is preferred that the patient has no lipstick, gloss, or emollients on their lips that could affect the administration process. The patient preferably stands or sits upright, and three large gulps of water are administered to prepare for capsule administration. The patient can be instructed not to bite down on the catheter, to close his/her mouth on catheter, to hold onto the catheter by hand, or to grab the catheter. The Capsule/Catheter is wet by submerging into the bowl of water for no more than 10 seconds. Within 1 minute of submerging the capsule in the water, the patient is handed the capsule/catheter and instructed to place the capsule immediately in the mouth and swallow the capsule with another large glass of water. The Proximal Catheter Port is held outside of the patient's mouth. The time of placement of the capsule/catheter in the mouth for swallow is documented. The patient is given additional water or juice (at least 100 ml) after swallow. The patient remains in an upright sitting or standing position the entire time. The patient is asked to continually drink water or juice to facilitate peristalsis of the capsule/catheter if the balloon has not visibly passed into the stomach. Once swallowed, the proximal end of the capsule/catheter assembly remains outside of the patients' mouth until after the balloon is filled. The catheter may have markings that are to be used as a reference guide to help determine how far the catheter has traveled after swallow or to be used with or without the radiography verification and with or without measurement provided by the digital gauge. When the 'bull's-eye' marking is at the patient's teeth, this indicates that the balloon is approximately 45 cm down the esophagus and fluoroscopy is used at this time to determine if the balloon is in the stomach. The preferred method to confirm proper balloon placement prior to inflation is with radiography (fluoroscopy/digital x-ray). The catheter markings can be used for additional reference as to when to properly perform the radiography or could be used alone to verify the length traveled into the stomach.

The Dispenser with the extension tube from the Accessory Kit is connected to the balloon catheter by connecting the catheter to the male luer port on the 3-way stopcock of the extension line previously connected to Dispenser. The lure fittings are tightened snugly with fingers. The valve on the Dispenser is in the closed position before proceeding to next steps to ensure the proper positioning and status of the balloon capsule prior to proceeding to the balloon fill.

Approximately 1-2 minutes after swallow, digital x-ray or fluoroscopy is performed with the patient standing or sitting upright, to determine location of the radio-opaque balloon marker in the stomach. At least 3-5 minutes after swallow, a second verification of device location is performed using the Dispenser. This is accomplished by turning the Dispenser Digital Gauge on by pressing the "ON" button, turning on the Gauge Backlight, pressing the "ON" button on again, and turning the 3-way valve on the stopcock counterclockwise 90 degrees until the valve stops to open the flow of gas from extension tubing to the balloon. The pressure initially drops on the pressure gauge by approximately 20 kPa and then proceeds to below 7 kPa when the capsule dissolves. This takes approximately 45 seconds but no longer than 4 minutes. If the pressure remains above 7 kPa, then the capsule has not dissolved sufficiently or the catheter is kinked. Having the patient drink more liquid may facilitate capsule dissolution. The pressure is monitored for up to 4 minutes. If after this time the pressure has not dropped to less than 7.0 kPa then the capsule has not dissolved or there is a kink in the catheter. Balloon fill steps are not initiated until the radio-opaque balloon valve is visualized in the stomach 20 and the Dispenser pressure gauge reads less than 7.0 kPa. During inflation, if there is indication of inflation in a constrained space (by pressure readings or patient symptoms) shut off the gas flow by closing the valve on the Dispenser, detach the catheter from the Dispenser, and evacuate the gas from the balloon with a 60 $cm^3$ syringe. The balloon can then be removed endoscopically. If the gauge reads less than 7.0 kPa, then the balloon can be filled. The balloon is not disconnected from the catheter prior to balloon fill completion. In the event of a premature disconnect, the catheter is retrieved by pulling it out and then the balloon is endoscopically punctured and removed.

The Disposable Nitrogen Canister contains 150 $cm^3$ of nitrogen that is transferred into the balloon to fill a single balloon to 8.3-17.2 kPa and 250 $cm^3$ of volume. When the gauge remains steady after decreasing from the initial set inflation pressure, the balloon is filled to the desired volume of 250 $cm^3$ at the desired pressure of 13.8 kPa in approximately 2 minutes. To fill the balloon, the Dispenser valve is turned to the on/open position. Equilibrium is observed about 2 minutes after opening the valve (inflation time). The final readout pressure on the Dispenser's digital gauge is verified as stable and reading 8.3-17.2 kPa. If the pressure is outside of the specified range, endoscopic removal of the balloon is performed. The pre-filled Syringe is attached to the Stopcock with a 3-way valve. The Stopcock with a 3-way Valve is rotated back 90 degrees to close the flow of gas from the Dispenser. The 3-way stopcock valve is not rotated until attached to the pre-filled syringe so as to avoid reducing the final starting pressure in the balloon such that the balloon may not maintain its volume for the 3-month period. The gauge is not zeroed by holding the zero button while pressure is being transferred, to avoid the need to then remove the balloon endoscopically.

The catheter is retrieved by pushing the 1.5 $cm^3$ filled Syringe plunger in one rapid and deliberate motion, so as to detach the catheter from the balloon valve in the stomach. If the catheter does not detach after the first attempt, the second 1.5 $cm^3$ water filled syringe can be used to again attempt to remove the catheter. On the second attempt, it is ensured that the catheter is straight (there are no kinks) and that the plunger is pressed in a rapid and deliberate motion. Force is used when pushing the Syringe, and the step is not performed slowly to avoid the catheter not ejecting properly. If catheter remains attached to the balloon, a second 3-ml syringe can be half way filled with water, and detachment can again be attempted. To facilitate detachment, the patient lifts his/her chin up to help reduce any gag reflex, then the catheter is slowly pulled out of the patient's mouth. The catheter and the needle inside the needle sleeve are visualized (white protective hub that came attached to the capsule device) to ensure the needle is intact. If the needle is not inside the needle sleeve, then the balloon is removed. The catheter is separated from the Stopcock with a 3-way valve by unscrewing the luer lock. The location of the balloon can be reverified using X-ray or fluoroscopy.

The disposable canister can be removed from the Dispenser and discarded. To remove, the Dispenser lever is moved to the 'open' position, and the canister is pushed up from the opposite side of the Dispenser, or the Dispenser is flipped upside down and the disposable canister naturally falls out. The Dispenser is reused for the next balloon placement.

The patient can be advised to drink liquids for the first 24 hours and then transition to soft solids for the next 24 hours (in the first 48-hours after placement). Patients are instructed not drink alcohol, sodas or other "fizzy" or carbonated drinks. After 3 days, patients are able to return to solid foods and follow the diet and behavior modification program provided to them by their physician.

While placement of the balloon does not require endoscopy; it can be desirable that a trained endoscopist be readily available should there be a problem with swallow of the balloon or an undiscovered swallowing disorder is detected during the procedure. The following should be considered if a patient is unsuccessful at his/her first placement attempt. If the device does not pass the pharynx in the patient's mouth after 30 seconds of attempting swallow, the capsule is removed from the mouth. A new wetted balloon capsule/catheter assembly is used. If the patient fails two attempts, this issue is discussed with the patient and it is determined if the patient remains a good candidate for the therapy. If the failure to swallow is due to anxiety, standard methods to reduce the patient's anxiety can be used. Esophageal transit of the device can be facilitated by use of clear carbonated beverages.

Patients are advised to report a change in satiety (i.e. increased hunger), and/or weight gain as this may be a sign that an additional balloon for therapy might be warranted. If multiple balloons have been placed and the patient reports a change in satiety levels (i.e. reduced early satiety), this may be a sign of balloon deflation. Balloon deflation can be evaluated using radiography (film x-ray, digital x-ray, or fluoroscopy) and gastroscopy as appropriate. Patients are advised to contact their physician if the frequency of adverse events experienced is more than anticipated or becomes intolerable. Concurrent use of Proton Pump Inhibitors can be desirable for the duration of use, e.g., 40 mg/day of pantoprazol or an equivalent dosage of similar medications, in that it is likely an effective treatment for undiagnosed pre-existing esophagitis and gastritis which may enhance tolerability of the devices in residence. Antiemetic and spasmolytic agents can be given immediately following balloon placement and given as needed while the balloon(s) are in the stomach.

After 12 weeks of use the balloon or balloons are removed from the patient. The procedure is conducted using a working length endoscope less than 1200 mm and the inner diameter is compatible with the accessory tools suggested for puncture and retrieval of the balloon. Suggested tools include a needle instrument, e.g., an injector needle in a Teflon Sleeve 23G×6 mm or similar having a lumen for suction, a Rat Tooth Grasper with Alligator Jaws or Two Jaw Grasping Forceps (with a minimum opening width of 15 mm); or a two-prong grasper with same minimum opening. Other retrieval tools may be acceptable for retrieving the balloons. Retrieval procedures in general are conducted per the gastroscope manufacturer's instructions for retrieving foreign objects. The endoscopy procedure performed is similar to that of an interventional or therapeutic procedure, however tailoring the endoscopic approach according to the unique product features is recommended, e.g., balloons should only be punctured once, so that the maximum amount of gas can be aspirated (via vacuum) from them, and a lesser degree of stomach inflation (less air insufflation) allows for easier puncture of the balloon. A typical capsule may include as ingredients porcine gelatin, water, methylparaben, propylparaben, and sodium lauryl sulfate. A typical balloon may be constructed from nylon and polyethylene (as wall materials), silicone (in the valve), and titanium (as a radioopaque component). The Dispenser is typically constructed of Stainless Steel, 6061 AL, Brass, Acetal, and Silicone. The canister contains 150 $cm^3$ of Nitrogen at 18 barr.

Preferably, patients are fasted at least 24 hours or per hospital protocol for gastroscope procedures to ensure the stomach 20 is empty and the balloon(s) are therefore easily visible. The patient is anesthetized per hospital and physician recommendations for gastroscope procedures. The gastroscope is inserted into the patient's stomach, and a clear view of the filled balloons is obtained through the gastroscope. The needle instrument is inserted down the working channel of the gastroscope. The valve of the balloon is located and the balloon is punctured with the needle only once (at the opposite end of the valve if possible for easier removal). Suction is applied and balloon gas is aspirated using a large syringe (60 cc) or aspiration tube. The needle is removed from the working channel, and the graspers are inserted through the working channel. The balloon is grabbed with the graspers at the opposite end of the valve. With a firm grasp on the balloon, the balloon is slowly extracted up through the esophagus, removing the balloon through the mouth. The removal procedure is repeated for the remainder of the balloons, if any.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

All references cited herein are incorporated herein by reference in their entirety. To the extent publications and patents or patent applications incorporated by reference contradict the disclosure contained in the specification, the specification is intended to supersede and/or take precedence over any such contradictory material.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for performing an inflation procedure to inflate an inflatable intragastric device, the system comprising:
   a) an inflation fluid container comprising an inflation fluid;
   b) an inflatable intragastric balloon;
   c) a fluid pathway fluidly connecting the inflation fluid container and the balloon;
   d) at lease one valve disposed along the fluid pathway and configured to control a volume of gas flowing through the fluid pathway into the balloon;
   e) a pressure gauge positioned along the fluid pathway so as to measure a balloon pressure within the balloon; and
   f) a computing device configured to:
      i) provide instructions to the at least one valve to dispense a volume of inflation fluid into the fluid pathway;
      ii) provide instructions to the at least one valve to block the flow of the inflation fluid into the fluid pathway;
      iii) receive balloon pressure measurements from the pressure gauge;
      iv) determine if the balloon is located within a constrained space, based upon the balloon pressure measurements, wherein the balloon is determined to be located within the constrained space when a pressure of between 17.2 kPa and 60 kPa is measured and a rate of pressure decrease less than 0.2 kPa/s is measured, and wherein the location is determined to be in an unconstrained space when a pressure of less than 17.2 kPa is measured in an absence of a rate of change of less than 0.2 kPa/s in 3 seconds.

2. The system of claim 1, wherein the constrained space is a first constrained space and the computing device is further configured to determine if the balloon is located within a second constrained space, based upon the balloon pressure measurements.

3. The system of claim 2, wherein the computing device is configured to distinguish between the first and second constrained spaces.

4. The system of claim 1, wherein the computing device is further configured to:
   a) compare the balloon pressure measurements to a target balloon pressure; and
   b) select instructions, wherein the instructions are selected from the group consisting of
      i) instructions to vent inflation fluid from the balloon, when the balloon pressure measurements are above the target balloon pressure;
      ii) instructions to continue the inflation procedure; and
      iii) instructions to terminate the inflation procedure.

5. The system of claim 4, wherein the computing device is further configured to provide fail-safe procedure instructions to a user.

6. The system of claim 1, wherein the volume of inflation fluid dispensed into the fluid pathway is a first volume of inflation fluid, and the computing device is further configured to
   a) compare the balloon pressure measurements to a target balloon pressure; and
   b) provide instructions to the at least one valve to dispense a second volume of inflation fluid into the fluid pathway, when the balloon pressure measurements are below the target balloon pressure.

7. The system of claim 1, wherein the computing device is further configured to
   a) compare the balloon pressure measurements to a target balloon pressure; and
   b) provide an indicium that the balloon is filled.

8. The system of claim 1, wherein the pressure gauge is positioned between the at least one valve and the balloon.

9. The system of claim 1, wherein the computing device is configured to compare received balloon pressure measurements to safety criteria.

10. The system of claim 1, wherein the computing device is configured to determine if the balloon pressure measurements are within a safety threshold.

11. The system of claim 1, wherein the constrained space has a volume less than or equal to 180 cm$^3$.

12. The system of claim 1, wherein the inflation fluid comprises $SF_6$ and nitrogen.

13. A system for inflating an inflatable intragastric device, comprising:
   a) a canister comprising an inflation fluid;
   b) an inflatable intragastric balloon;
   c) a fluid pathway fluidly joining the canister and the balloon, the fluid pathway comprising:
      i) a pressure sensor;
      ii) a first pressure regulator configured to reduce the pressure of inflation fluid received from the canister to a pressure less than a constrained space-damaging pressure;
      iii) a first valve configured to control flow of the inflation fluid through the fluid pathway; and
      v) an exhaust configured to vent inflation fluid from the balloon; and
   f) a processing unit configured to:
      i) receive pressure measurements from the pressure sensor;
      ii) determine a location of the balloon, based on the received pressure measurements, wherein the location is determined to be in a constrained space when a pressure of between 17.2 kPa and 60 kPa is measured and a rate of pressure decrease less than 0.2 kPa/s is measured, and wherein the location is determined to be in an unconstrained space when a pressure of less than 17.2 kPa is measured in an absence of a rate of change of less than 0.2 kPa/s in 3 seconds;
      iii) when the balloon location is determined to be the unconstrained space, determine an amount of inflation fluid to dispense from the canister to achieve a target pressure within the balloon based on the pressure measurements, and provide instructions to dispense inflation fluid into the fluid pathway based on the determined amount of inflation fluid to dispense from the canister;
      v) when the balloon location is determined to be the constrained space, provide instructions to perform a fail-safe procedure.

14. The system of claim 13, wherein the processing unit is configured to vent inflation fluid from the balloon when balloon pressure is greater than about 17.2 kPa.

15. The system of claim 13, wherein the processing unit is configured to provide an alert when the balloon is located in the constrained space.

16. The system of claim 13, wherein the constrained space has a volume of less than or equal to about 180 cm$^3$.

17. The system of claim 13, wherein the target pressure is between about 9.5 kPa to about 13 kPa.

18. The system of claim 13, wherein the target pressure is between about 8.3 kPa to about 17.2 kPa.

19. The system of claim 13, wherein the inflation fluid comprises $SF_6$ and nitrogen.

* * * * *

UNITED STATES PATENT AND TRADEMARK OFFICE
CERTIFICATE OF CORRECTION

PATENT NO. : 11,819,433 B2
APPLICATION NO. : 16/993110
DATED : November 21, 2023
INVENTOR(S) : Brister et al.

It is certified that error appears in the above-identified patent and that said Letters Patent is hereby corrected as shown below:

In the Specification

In Columns 25-26, Line 61, TABLE 2, delete "AL$_2$O$_3$" and insert --Al$_2$O$_3$--.

In Column 32, Line 19, delete "Intragastic" and insert --Intragastric--.

In Column 36, Line 23, delete "Dispeners" and insert --Dispensers--.

In Column 48, Line 49, delete "A," and insert --$\Delta$,--.

In Column 61, Line 58, delete "cm3." and insert --cm$^3$--.

In Column 62, Line 7, delete "KPA" and insert --kPa--.

In Column 62, Line 60, delete "KPa" and insert --kPa--.

In Column 65, Line 58, delete "lure" and insert --luer--.

In Column 68, Line 17, delete "barr." and insert --bar.--.

In the Claims

In Column 70, Line 1, Claim 1 delete "lease" and insert --least--.

In Column 71, Line 21, Claim 13 delete "v)" and insert --iv)--.

In Column 72, Line 13, Claim 13 delete "v)" and insert --iv)--.

Signed and Sealed this
Twentieth Day of February, 2024

*Katherine Kelly Vidal*
*Director of the United States Patent and Trademark Office*